US012703693B2

(12) United States Patent
Schestopol et al.

(10) Patent No.: US 12,703,693 B2
(45) Date of Patent: Aug. 11, 2026

(54) CRYSTALLINE FORMS OF N-{3-[(1S)-1-{[6-(3,4-DIMETHOXYPHENYL) PYRAZIN-2-YL]AMINO}ETHYL]PHENYL}-5-METHYLPYRIDINE-3-CARBOXAMIDE AND RELATED PRODUCTS AND METHODS

(71) Applicant: GB002, INC., San Diego, CA (US)

(72) Inventors: Marcus Schestopol, San Diego, CA (US); Beili Zhang, San Diego, CA (US); David Paisner, San Diego, CA (US); Nicole White, San Diego, CA (US); Esmir Gunic, San Diego, CA (US)

(73) Assignee: GB002, Inc., San Diego, CA (US)

( * ) Notice: Subject to any disclaimer, the term of this patent is extended or adjusted under 35 U.S.C. 154(b) by 393 days.

(21) Appl. No.: 18/558,355

(22) PCT Filed: May 6, 2022

(86) PCT No.: PCT/US2022/028197
§ 371 (c)(1),
(2) Date: Oct. 31, 2023

(87) PCT Pub. No.: WO2022/236139
PCT Pub. Date: Nov. 10, 2022

(65) Prior Publication Data

US 2024/0228462 A1 Jul. 11, 2024

Related U.S. Application Data

(60) Provisional application No. 63/185,996, filed on May 7, 2021.

(51) Int. Cl.

| | |
|---|---|
| ***C07D 401/12*** | (2006.01) |
| ***A61K 9/00*** | (2006.01) |
| ***A61K 9/48*** | (2006.01) |
| ***A61K 9/50*** | (2006.01) |
| ***A61K 31/496*** | (2006.01) |

(52) U.S. Cl.
CPC .......... *C07D 401/12* (2013.01); *A61K 9/0075* (2013.01); *A61K 9/4816* (2013.01); *A61K 9/4858* (2013.01); *A61K 9/5015* (2013.01); *A61K 31/496* (2013.01)

(58) Field of Classification Search
CPC .. C07D 401/12; A61K 9/0075; A61K 9/4816; A61K 9/4858; A61K 9/5015; A61K 31/496
USPC .................................................... 514/255.05
See application file for complete search history.

(56) References Cited

U.S. PATENT DOCUMENTS

| | | | |
|---|---|---|---|
| 9,815,815 B2 * | 11/2017 | Zisman | .................. A61P 21/00 |
| 10,231,966 B2 | 3/2019 | Zisman | |
| 2021/0038510 A1 | 2/2021 | Zisman | |

FOREIGN PATENT DOCUMENTS

| | | |
|---|---|---|
| CN | 105142624 A | 12/2015 |
| CN | 106132403 A | 11/2016 |
| CN | 108473529 A | 8/2018 |
| CN | 110087653 A | 8/2019 |
| JP | 2016506418 A | 3/2016 |
| WO | 2019157337 A1 | 8/2019 |

OTHER PUBLICATIONS

Balbach et al., "Pharmaceutical evaluation of early development candidates "the 100 mg-approach"," International Journal of Pharmaceutics 275:1-12, May 4, 2004. (12 pages).
Byrn et al., "Pharmaceutical Solids: A Strategic Approach to Regulatory Considerations," Pharmaceutical Research 12 (7):943-1114, Jul. 1995. (11 pages).
Mino R. Caira, "Crystalline Polymorphism of Organic Compounds," Topics in Current Chemistry 198, Sep. 10, 1998. (26 pages).
Mino R. Caira, "Crystalline Polymorphism of Organic Compounds," Topics in Current Chemistry 198, Sep. 10, 1998. (46 pages).
Savjani et al., "Drug Solubility: Importance and Enhancement Techniques," ISRN Pharmaceutics, 2012(195727), Jul. 5, 2012. (10 pages).
Singhal et al., "Drug polymorphism and dosage form design: a practical perspective," Advanced Drug Delivery Reviews 56:335-347, Feb. 23, 2004. (13 pages).

* cited by examiner

*Primary Examiner* — Kahsay Habte
(74) *Attorney, Agent, or Firm* — Seed Intellectual Property Law Group LLP

(57) ABSTRACT

Crystalline forms of N-{3-[(1S)-1-{[6-(3,4-dimethoxyphenyl)pyrazin-2-yl]amino}ethyl]-phenyl}-5-methylpyridine-3-carboxamide are provided. Pharmaceutical compositions and dosage forms containing the crystal forms are also provided, including related methods for modulating kinases generally, and specifically to treatment of PAH.

57 Claims, 38 Drawing Sheets

CRYSTALLINE FORMS OF N-{3-[(1S)-1-{[6-(3,4-DIMETHOXYPHENYL) PYRAZIN-2-YL]AMINO}ETHYL]PHENYL}-5-METHYLPYRIDINE-3-CARBOXAMIDE AND RELATED PRODUCTS AND METHODS

This application claims the benefit of priority to U.S. Provisional Application No. 63/185,996, filed May 7, 2021, which application is hereby incorporated by reference in its entirety.

FIELD OF THE INVENTION

The present invention relates to crystalline forms of N-{3-[(1S)-1-{[6-(3,4-dimethoxyphenyl)pyrazin-2-yl] amino}ethyl]phenyl}-5-methylpyridine-3-carboxamide, as well as to products comprising such crystalline forms, and related methods of their use and preparation.

BACKGROUND

Receptor tyrosine kinases are transmembrane polypeptides that regulate the regeneration, remodeling, development, and differentiation of cells. Among the receptor tyrosine kinases is the platelet derived growth factor receptor (PDGFR), which is associated with pulmonary diseases, tissue fibrosis, and solid tumors.

Among the pulmonary diseases, pulmonary hypertension (PH) is a rare disorder of the pulmonary vasculature that is associated with high morbidity and mortality. The pathology of the disease includes plexiform lesions of disorganized angiogenesis and abnormal neointimal cellular proliferation, which obstruct blood flow through the pulmonary arterioles. Known kinase receptor inhibitors, and in particular known PDGFR inhibitors, are not orally available, are associated with off-target effects that can contribute to PH development, and/or are associated with dose limiting side effects. Accordingly, there is a need for agents that can inhibit PDGFRα and/or PDGFRβ with improved potency and selectivity over other kinases known to be involved with dose-limiting side effects (e.g., cKit, FLT3 and VEGFR2).

N-{3-[(1S)-1-{[6-(3,4-dimethoxyphenyl)pyrazin-2-yl] amino}ethyl]phenyl}-5-methylpyridine-3-carboxamide, also known as GB002 or Seralutinib (and hereinafter referred to as "Compound 1"), is a highly potent and selective inhibitor of PDGFRα and PDGFRβ signaling. Compound 1 is under clinical development as an inhaled treatment for pulmonary arterial hypertension (PAH). An amorphous form of Compound 1 has been described in U.S. Pat. Nos. 9,815,815 and 10,231,966, and in a spray-dried powder formulation in U.S. Pat. No. 9,925,184. Compound 1 has the following structure:

Compound 1

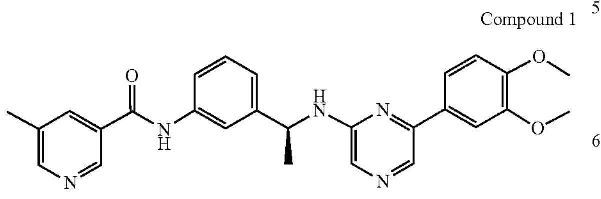

Given the clinical promise of Compound 1, there is a need for new, improved and/or enhanced forms of Compound 1, particularly in the context of pharmaceutical drug products suitable for delivery by inhalation, as well as for compositions comprising Compound 1 and methods related to the manufacture and use of the same. The present invention fulfils these and related needs, as evidenced by the following detailed description and attached drawings.

BRIEF SUMMARY

Solids drug forms may exist in either amorphous or crystalline states. In the case of crystalline forms, molecules are positioned in 3-dimensional lattice sites. When a compound recrystallizes from a solution or slurry, it may crystallize with different spatial lattice arrangements, a property referred to as "polymorphism," with the different crystal forms being referred to as "polymorphs" or individually as a "polymorph". Different polymorphs of a given substance may differ from each other with respect to one or more physical properties, such as solubility and dissociation, true density, crystal shape, compaction behavior, flow properties, and/or solid state stability. In the case of a chemical substance that exists in two (or more) polymorphic forms, unstable form(s) generally convert to the more thermodynamically stable form(s) at a given temperature after a sufficient period of time. When this transformation is not rapid, the thermodynamically unstable form is referred to as the "metastable" form. In general, the stable form exhibits the highest melting point, the lowest solubility, and the maximum chemical stability. However, the metastable form may exhibit sufficient chemical and physical stability under normal storage conditions to permit its use in a commercial form. In this case, the metastable form, although less stable, may exhibit properties desirable over those of the stable form, such as enhanced solubility or better oral bioavailability.

Accordingly in one embodiment, a novel solid crystalline forms of Compound 1 are provided. In more specific embodiments, the novel solid crystalline forms are two different polymorphs of Compound 1, which are referred to herein as "Form A" and "Form B".

In an embodiment, a crystalline form of Compound 1 is provided wherein the crystalline form is Form A, and in a further embodiment is substantially pure From A. Form A may be characterized by the various analytical techniques disclosed herein, including (for example) by X-ray powder diffraction (XRPD) and the characteristic diffractograms generated by the same.

In an embodiment, a crystalline form of Compound 1 is provided wherein the crystalline form is Form B, and in a further embodiment is substantially pure From B. Form B may be characterized by the various analytical techniques disclosed herein, including (for example) by X-ray powder diffraction (XRPD) and the characteristic diffractograms generated by the same.

In an embodiment, a crystalline form of Compound 1 is provided wherein the crystalline form is a mixture of Form A and Form B. As defined below, a mixture is provided when one crystalline form is present at a ratio ranging from of 5-95% by weight of the other crystalline form (ratios of Form A and Form B above or below this range are characteristic of substantially pure crystalline forms).

In another embodiment, a pharmaceutical composition is provided comprising a solid crystalline form of Compound 1 in combination with one or more pharmaceutically acceptable carriers. Such compositions may be formulated in a variety for different forms. For example, the composition may be formulated for administration to the respiratory track, such as in the form of an inhalable powder, or as a dry powder. Such powder forms may be further characterized, such as by their size (e.g., by volume distribution in which half are above and half below a particular diameter, abbreviated "Dv50").

In an embodiment, the pharmaceutical composition may comprise an additional therapeutically active agent (i.e., in addition to the crystalline form of Compound 1).

In an embodiment, the pharmaceutical composition may comprise leucine, and in a more specific embodiment, the leucine coats the solid crystalline form of Compound 1. In a related embodiment, the leucine-coated form is obtained by wet polishing.

In another embodiment, a solid unit dosage form is provided comprising a solid crystalline form of Compound 1. Such dosage forms refer to the drug product in the form in which it is marketed for use. For example, unit dosage forms may be in a form suitable for administration to the respiratory track, such as in the form of an inhalable powder or as a dry powder, including capsule or blisters containing the same used in conjunction with, for example, a dry powder inhaler.

In another embodiment, a method is provided for treating a disease or condition modulated by kinase inhibition, comprising administering to a subject in need thereof an effective amount of a crystalline form of Compound 1, a pharmaceutical composition comprising the same, or a solid unit dosage form comprising the same. In a more specific embodiment, the kinase is a tyrosine kinase such as (but not limited to) the platelet derived growth factor PDGFR and, more specifically, PDGFRα and/or PDGFRβ.

In an embodiment, the disease or condition is PAH, primary PAH, idiopathic PAH, heritable PAH, refractory PAH, drug-induced PAH, toxin-induced PAH, or PAH with secondary diseases, and in a more specific embodiment is PAH.

In yet another embodiment, a process is provided for preparing a solid crystalline form of Compound 1 by crystallization from a solvent comprising ethyl acetate. In one embodiment, the solvent may further comprise water and either n-heptane or ethanol.

In one embodiment, Applicants have surprisingly found processes for preparing crystalline Form B from crystalline Form A by slurrying Form A of Compound 1 in ethyl acetate and holding its temperature from about 10° C. to about 45° C. for a period of time from 1 minute to 90 hours.

DETAILED DESCRIPTION

According to the present disclosure, novel solid crystalline forms of Compound 1 are provided. In more specific embodiments, the novel solid crystalline forms are two different polymorphs of Compound 1; namely, Form A and Form B. Form A and Form B differ from the amorphous form of Compound 1 in the structure of the crystal lattice, with each form giving distinctive x-ray powder diffraction (XRPD) patterns and differential scanning calorimeter (DSC) thermograms.

As used herein "amorphous" refers to a lack of well-ordered diffraction lines resulting from the absence of a repeated crystal lattice. As used herein the amorphous form of N-{3-[(1S)-1-{[6-(3,4-dimethoxyphenyl)pyrazin-2-yl] amino}ethyl]phenyl}-5-methylpyridine-3-carboxamide can be prepared according the procedure set forth in U.S. Pat. No. 9,815,815 (see Columns 29, line 25 through Col. 31, line 11), the disclosure of which is hereby incorporated by reference in its entirety.

Accordingly, in one embodiment the present disclosure provides Form A, characterized by a XRPD pattern having peaks at 5.5, 7.8, 11.0, 12.3 and 15.6±0.2 degrees 2-theta.

Figure 3:
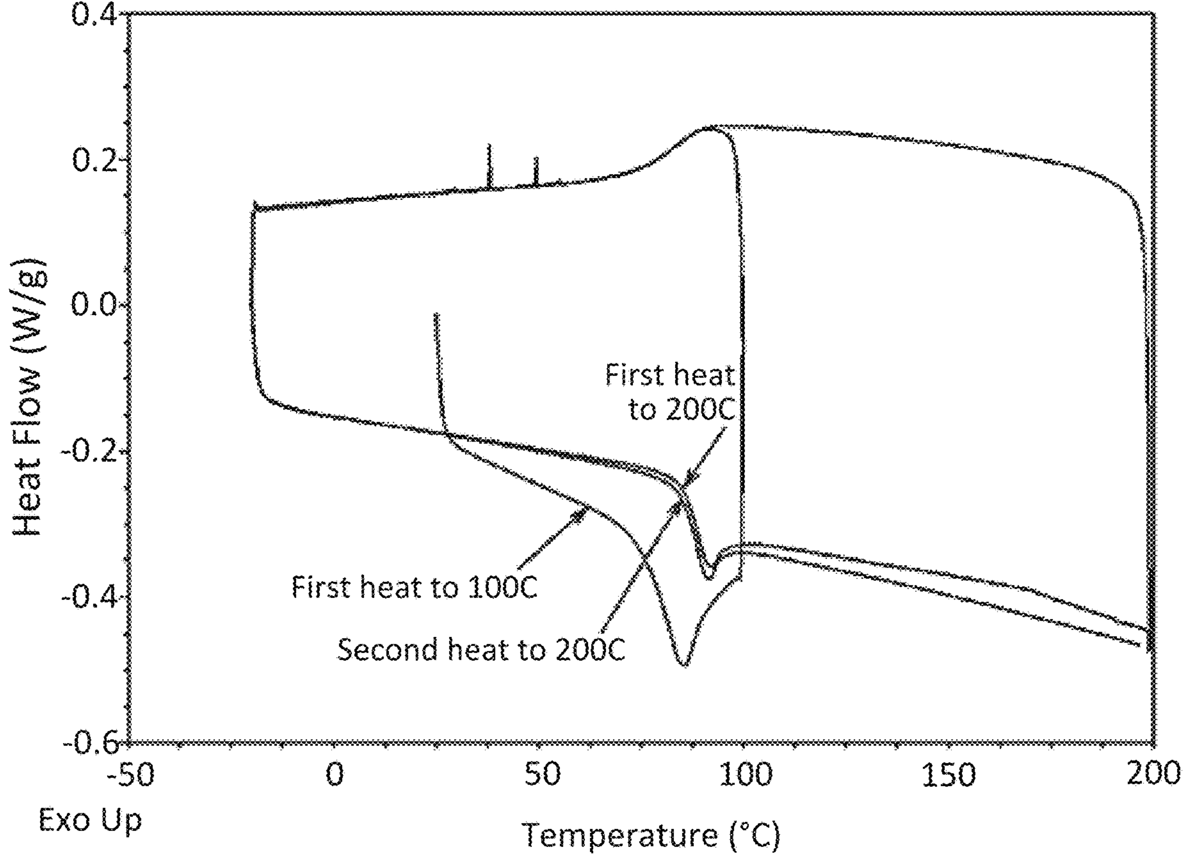
FIG. 3: DSC of amorphous Compound 1, (heating to 200° C.

In another embodiment Form A is provided further characterized by an XRPD pattern substantially as shown in FIG. 3.

In the practice of this invention, a single polymorph (i.e., Form A or Form B) may be utilized in a substantially pure form, or may be utilized as a mixture of polymorphs (i.e., a mixture of Form A and From B).

In one embodiment, one crystalline form (i.e., Form A or Form B) is present in an amount in excess of 95% by weight compared to the other crystalline form. Thus, substantially pure Form A contains less than 5% by weight of Form B. Conversely, substantially pure Form B contains less than 5% by weight Form A. In further embodiments, one crystalline form (i.e., Form A or Form B) is present in an amount in excess of 96%, 97%, 98% or 99% by weight compared to the other crystalline form (i.e., the other crystalline form is present in an amount less than 4%, 3%, 2% or 1% by weight of the other form). In another embodiment, one crystalline form (i.e., Form A or Form B) is present in an amount in excess of 99.2%, 99.4%, 99.6% or 99.8% by weight compared to the other crystalline form.

In another embodiment, the crystalline form of Compound 1 contains a mixture of Form A and Form B. As used herein, a mixture of Form A and Form B means that Form A is present at a ratio ranging from 5-95% by weight of Form A compared to Form B or, conversely, from 5-95% by weight of Form B compared to Form A. As defined above, when either Form A or Form B is present in an amount that exceeds 95% by weight compared to the other form, then Form A or Form B is considered to be substantially pure relative to the other form.

In one embodiment, Form A comprises at least 80% Form A.

In another embodiment, Form A comprises at least 90% Form A.

In one embodiment, Form B is provided characterized by a XRPD pattern having peaks at 5.2, 6.1, 7.6, 11.5 and 12.3±0.2 degrees 2-theta.

Figure 4:
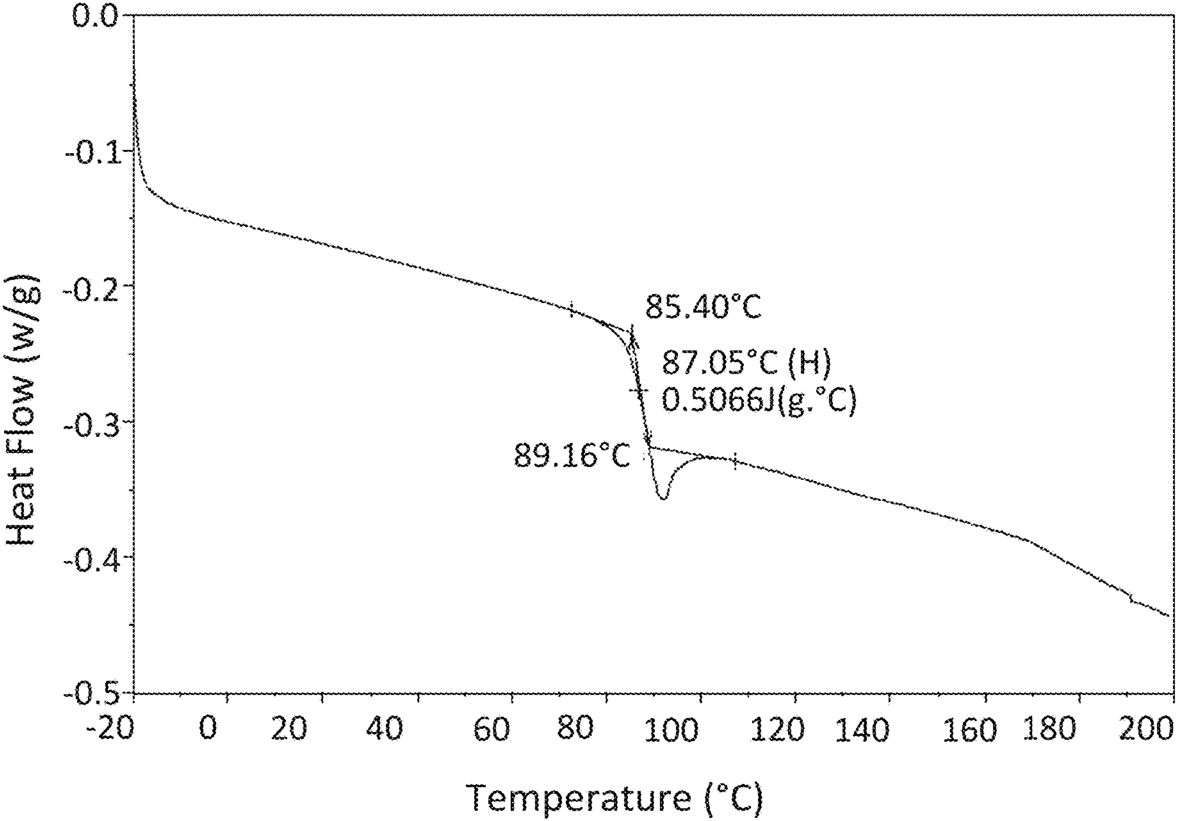
FIG. 4: DSC of amorphous Compound 1, first scan to 200° C. for Tg and ΔCp.

In another embodiment, Form B is provided further characterized by an XRPD pattern substantially as shown in FIG. 4.

In another embodiment, Form B comprises 80% Form B.

In another embodiment, Form B comprises 90% Form B.

In one embodiment, the crystalline form of Compound 1 contains substantially pure Form A or substantially pure Form B.

It has surprisingly been found that the crystal forms of Compound 1 are particularly advantageous with regard to their use as a pharmaceutical agent, particularly in the context of administration via inhalation.

In one embodiment, micronization of the crystal forms to a respirable fraction size is provided by the present disclosure.

In another embodiment, the respirable fraction size is measured in median particle size.

In yet another embodiment, the median particle size is less than 5 μM, in some instances between 2-4 μM, and in yet other instances between 3 and 3.5 μM.

In one embodiment, the crystal Form A is micronized.

In another embodiment, crystal Form A is micronized without reverting back to the amorphous form of Compound 1.

In yet another embodiment, the micronization occurs using wet polishing.

In still another embodiment, micronization of crystal forms is undertaken with a mixture of Forms A and B of Compound 1.

In one embodiment, Form A of Compound 1 is characterized as having high solubility in mixtures of ethanol/water ranging from about 2 mg/mL to about 350 mg/mL and does not show a decline in solubility over 24 h.

In another embodiment, Form A of Compound 1 is also characterized as having moderate solubility in phosphate buffer, pH 7.4 and does not show a decline in solubility over 24 h in contrast to the amorphous form of Compound 1 which shows a progressive decline in solubility.

Applicants have found that when they attempted the scale up of amorphous Compound 1 in the context of manufacture of pharmaceutical drug products for clinical trials, their attempts were not successful. Applicants discovered surprisingly that crystalline Compound I could be scaled up with an improved purity profile.

In a further embodiment, the crystalline form of Compound 1 contains less than 2% by weight total impurities, less than about 1% by weight water, and/or less than about 0.5% by weight residual organic solvent.

In one embodiment, solution phase NMR spectroscopy can be used to verify the purity and chemical structure of crystal forms, Form A and Form B.

In another embodiment, Thermogravimetric (TGA) analysis can be utilized to verify that a polymorph is anhydrous. In reference to FIG. 7-8, TGA indicates that the crystal forms are anhydrous. In one embodiment, Form B of Compound 1 has a slightly higher melting point compared to Form A, as measured by Differential Scanning calorimeter.

Applicants have discovered methods for converting one particular crystal polymorph of Compound 1 to another. Accordingly, in another embodiment, as addressed in greater detail in the examples below, it is believed that Form B is an anhydrous/non-solvated solid, and From A slowly converts to Form B, indicating the Form A and Form B are enantiotropically related. Accordingly, Form A may also be referred to as the metastable form, since conversion of Form A to Form B has been observed (but not conversion of Form B to Form A), and Form A has a lower melting point compared to that of Form B. Crystalline Form A and Form B of Compound 1 differ in their crystal structure as determined by, for example, X-Ray Powder Diffraction (XRPD). The XRPD pattern of Form A and Form B are provided in Table 7 below.

In one embodiment, crystalline Form A of Compound 1 is slurried in ethyl acetate and its temperature held from about 10° C. to about 45° C. for a period of time from 1 minute to 90 hours, sufficient for the conversion of Form A to Form B. Samples were withdrawn at regular time intervals and their XRPD patterns determined.

The present disclosure also provides processes for the preparation of the crystalline forms of Compound 1 comprising crystallization.

In one embodiment, crystallization comprises dissolving the amorphous Compound 1 in 1,4-dioxane, lyophilizing the solution, and adding a test solvent to allow post-thermal cycling and/or evaporation.

In one embodiment, the test solvent is ethyl acetate.

In another embodiment, the test solvent is acetonitrile.

In yet another embodiment, the test solvent is ethyl acetate/tBME in equal amounts.

In another embodiment, crystallization is induced with the addition of an anti-solvent.

In yet another embodiment, the anti-solvent is heptane.

In one embodiment, processes are provided to prepare Form B directly from amorphous Compound 1 using a first solvent and a second solvent or anti-solvent.

In yet another embodiment, the first solvent is ethanol and the second solvent or anti-solvent is water.

Also as mentioned above, Compound 1 has only previously been obtained in an amorphous form. By the techniques disclosed in the Examples below, substantially pure Form A and substantially pure Form B, as well as mixtures of Form A and Form B, may be obtained. Once obtained, such crystalline forms may be employed in the preparation of pharmaceutical compositions comprising the same in combination with one or more pharmaceutically acceptable carriers. The compositions of the present invention may also contain other therapeutic agents as described below, and may be formulated, for example, by employing conventional solid or liquid vehicles or diluents, as well as pharmaceutical additives of a type appropriate to the mode of desired administration, for example, excipients, binders, preservatives, stabilizers, flavors, etc., according to techniques such as those well known in the art of pharmaceutical formulation.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment for a treatment course.

The crystalline forms of Compound 1 of the present disclosure are administered by any suitable means, for example, orally, such as in the form of tablets, capsules, granules or powders; sublingually; buccally; parenterally, such as by subcutaneous, intravenous, intramuscular, intra (trans)dermal, or intracisternal injection or infusion techniques, e.g., as sterile injectable aqueous or non-aqueous solutions or suspensions, nasally such as by inhalation spray or insufflation, topically, such as in the form of a cream or ointment ocularly in the form of a solution or suspension, vaginally in the form of pessaries, tampons or creams, or rectally such as in the form of suppositories, in unit dosage formulations containing nontoxic, pharmaceutically acceptable vehicles or diluents. The crystalline forms of Compound 1 may, for example, be administered in a form suitable for immediate release or extended release. Immediate release or extended release may be achieved by the use of suitable pharmaceutical compositions comprising the crystalline forms of Compound 1 or, for extended release, by the use of devices such as subcutaneous implants or osmotic pumps.

For administration to the respiratory tract, e.g., inhalation, including intranasal administration, the active compound may be administered by any of the methods and formulations employed in the art for administration to the respiratory tract. Thus, the active compound may be administered in the form of, e.g., a solution, suspension, or as a dry powder, with the dry powder form being a preferred embodiment. The agents according to this aspect of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In one embodiment for the purposes of administration to the respiratory tract, the crystalline forms of Compound 1 are micronized. In more specific embodiments, micronization is accomplished by wet polishing or by jet milling.

In one embodiment, the micronized form is filled into capsules for administration as a dosage form for use in a dry powder inhaler. In another embodiment, the micronized form is filled into blisters for administration as a dosage form for use in a dry powder inhaler. In another embodiment, the micronized form is filled directly into a dry powder inhaler for administration.

In one embodiment for the purposes of administration to the respiratory tract, the pharmaceutical composition may comprise leucine as a force control agent. In a more specific embodiment, leucine is micronized along with the crystalline form of Compound 1 (e.g., co-milled).

In another embodiment, the leucine coats the solid crystalline form of Compound 1, and in a more specific embodiment coats the micronized crystalline form of Compound 1.

In yet another embodiment, the leucine-coated form is obtained by micronization, and in a more specific embodiment by spray drying an aqueous suspension following micronization of the solid crystalline form of Compound 1.

In another embodiment, the micronization step for obtaining the leucine coated crystalline form of Compound 1 is accomplished by jet milling.

In another embodiment, the micronization step for obtaining the leucine coated crystalline form of Compound 1 is accomplished by wet polishing.

In one embodiment, the leucine coated micronized crystalline form of Compound 1 is filled into capsules for administration as a dosage form.

In another embodiment, the leucine coated micronized crystalline form of Compound 1 is filled into blisters for administration as a dosage form for use in a dry powder inhaler.

In another embodiment, the leucine coated micronized crystalline form of Compound 1 is filled directly into a dry powder inhaler for administration.

In another embodiment, the leucine coated micronized crystalline dosage form of Compound 1 has a higher drug loading than the amorphous dosage form.

The propellant-driven inhalation aerosols which may be used according to the invention may also contain other ingredients such as co-solvents, stabilizers, surfactants, antioxidants, lubricants and pH adjusters. The propellant-driven inhalation aerosols according to the invention which may be used according to the invention may be administered using inhalers known in the art, e.g., metered dose inhalers. As another alternative, the agents of the present invention may be administered to the airways in the form of a lung surfactant formulation. The lung surfactant formulation can include exogenous lung surfactant formulations (e.g., Infasurf® (Forest Laboratories), Survanta® (Ross Products), and Curosurf® (DEY, California, USA) or synthetic lung surfactant formulations (e.g., Exosurf® (GlaxoWellcome Inc.) and ALEC). These surfactant formulations are administered via airway instillation (i.e., after intubation) or intratracheally.

As a further alternative, the crystalline forms of Compound 1 of the present invention may be administered to the airways in the form of an inhalable powder. The powder formulation may include physiologically acceptable excipients such as amino acids (e.g., leucine), monosaccharides (e.g. glucose or arabinose), disaccharides (e.g. lactose, saccharose and maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in hydrate form.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipients mentioned above. These finer excipients are also selected from the group of possible excipients listed hereinbefore. Finally, in order to prepare the inhalable powders according to the invention, micronised formulations, preferably with an average particle size of 0.5 to 10 μm is added to the excipient mixture. Processes for producing the inhalable powders according to the invention by grinding and micronizing and by finally mixing the ingredients together are known from the prior art.

In formulations intended for administration to the respiratory tract, including intranasal formulations, the active compound is typically configured to have a small particle size, e.g., approximately 5 microns or less, via micronisation techniques and the like. Sustained release formulations of the active compound are employed in some embodiments. The active compound, in some embodiments, is administered by oral inhalation as a free-flow powder via inhaler.

The pharmaceutical composition and method of the present disclosure further include additional therapeutically active compounds (second agents), as noted herein and/or known in the art, which are typically employed for treating one or more pathological conditions in concert with the compositions comprising Compound 1 of the present disclosure. The combination of therapeutic agents acts synergistically to effect the treatment or prevention of the various diseases, disorders, and/or conditions described herein. Such second agents, include, but are not limited to, of prostanoids, endothelin antagonists, cytoplasmic kinase inhibitors, receptor kinase inhibitors, endothelin receptor antagonists, e.g., ambrisentan, bosentan, and sitaxsentan, PDE5 (PDE-V) inhibitors, e.g., sildenafil, tadalafil, and vardenafil, calcium channel blockers, e.g., amlodipine, felodipine, varepamil, diltiazem, and menthol, prostacyclin, treprostinil, iloprost, beraprost, nitric oxide, oxygen, heparin, warfarin, diuretics, digoxin, cyclosporins, e.g., cyclosporin A, CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39, i.e., CD 154, fusion proteins constructed from CD40 and gp39 (CD40 1 g and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen, aspirin, acetaminophen, leflunomide, deoxyspergualin, cyclooxygenase inhibitors such as celecoxib, steroids such as prednisolone or dexamethasone, gold compounds, beta-agonists such as salbutamol, LABAs such as salmeterol, leukotriene antagonists such as montelukast, antiproliferative agents such as methotrexate, FK506 (tacrolimus, Prograf), mycophenolate mofetil, cytotoxic drugs such as azathioprine, VP-16, etoposide, fludarabine, doxorubin, adriamycin, amsacrine, camptothecin, cytarabine, gemcitabine, fluorodeoxyuridine, melphalan and cyclophosphamide, antimetabolites such as methotrexate, topoisomerase inhibitors such as camptothecin, DNA alkylators such as cisplatin, kinase inhibitors such as sorafenib, microtubule poisons such as paclitaxel, TNF-α inhibitors such as tenidap, anti-TNF antibodies or soluble TNF receptor, hydroxy urea and rapamycin (sirolimus or Rapamune) or derivatives thereof. Accordingly, in another embodiment, methods are provided for treating a disease of condition in subject in need thereof, by administering an effective amount the solid crystalline form of Compound 1, or a pharmaceutical composition comprising the same, to a subject. As used herein, "administration" to a subject includes any route of introducing or delivering to a subject the solid crystalline form of Compound 1 to perform its intended function. Administration can be carried out by any suitable route, including orally, intranasally, by inhalation, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and where some biologically or medically relevant result is achieved.

Similarly, the terms "effective amount" or "pharmaceutically effective amount" is a quantity sufficient to achieve a desired therapeutic and/or prophylactic effect, e.g., an amount which results in the prevention of, or a decrease in, the symptoms associated with a disease that is being treated. The amount of the solid crystalline form of Compound 1 administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

Such an administration the crystalline form of Compound 1 will elicit a response associated with, e.g., cells, tissues, fluids, of a subject being sought by the clinician. In the treatment or prevention of conditions mediated by, or associated with, kinase inhibition, e.g., RTK inhibition, an appropriate dosage level is administered. In some embodiments, from about 0.01 to 500 mg/kg of subject body weight per day is administered in single or multiple doses. In accord, dosage levels are from about 0.1 to about 250 mg/kg per day in some embodiments, while in other embodiments from about 0.5 to about 100 mg/kg per day is administered to the subject. Suitable dosage levels include, for example, from about 0.01 to 250 mg/kg per day, from about 0.05 to 100 mg/kg per day, or from about 0.1 to 50 mg/kg per day. Within this range, in some embodiments, the dosage is from about 0.05 to 0.5, 0.5 to 5 or 5 to 50 mg/kg per day. For oral administration, the compositions are provided in the form of tablets containing 1.0 to 1000 mg of the active ingredient, including, but not limited to, 1, 5, 10, 15, 20, 25, 50, 75, 100, 150, 200, 250, 300, 400, 500, 600, 750, 800, 900, and 1000 mg of the active ingredient. The dosage may be selected, for example, to any dose within any of these ranges, for therapeutic efficacy and/or symptomatic adjustment of the dosage to the subject being treated. In some embodiments, the compounds of the present disclosure are administered by inhalation as described in, e.g., U.S. Pat. Nos. 8,257,741, 8,263,128, WO 2010/132827, WO 2010/102066, WO 2012/040502, WO 2012/031129, and/or WO 2010/102065, from 1 to 20, 1 to 15, 1 to 10, 1 to 5, 1 to 4, or 1 to 3 times daily, or once or twice per day. In some embodiments, the compounds of the present disclosure are administered from 1 to 5 times daily.

In some embodiments, the unit dose is sufficient to provide one or more of: (a) a $C_{max}$ of about 1 to 5000 ng/ml of the compound In a subject's plasma or a $C_{max}$ of about 1 to 5000 ng/ml of the compound In the subject's blood when it is administered to the subject; and (b) about 1 to 5000 ng/mL of the compound in a subject's plasma 24 h after administration or about 1 to 5000 ng/ml of the compound in the subject's blood 24 h after administration to the subject.

The crystalline forms of Compound 1, particularly in the form of a pharmaceutical composition, may be used to treat any of a variety of diseases or conditions that would benefit from kinase inhibition, including those mediated by or associated with kinases such as cell division cycle 2 kinase (Cdc2 kinase), c-Kit, c-ABL, p60src, AKT, VEGFR3, PDGFRα, PDGFRβ, PDGFR-αα, PDGFR-ββ, PDGFR-αβ, FGFR3, FLT-3, FYN oncogene kinase related to SRC, FGR, YES (Fyn), lymphocyte-specific protein tyrosine kinase (Lck), tyrosine kinase with Ig and EGF homology domains (Tie-2), FMS (CSF-IR), KDR, EphA2, EphA3, EphA8, FLT1, FLT4, HCK, PTK5, RET, SYK, DDR1, DDR2, glycogen synthase kinase 3 (GSK-3), cyclin dependent kinase 2 (Cdk2), cyclin dependent kinase 4 (Cdk4), MEK1, NEK-2, CHK2, CKIε, Raf, checkpoint kinase 1 (CHK1), ribosomal S6 kinase 2 (Rsk2), and PAR-1. In particular, compounds, compositions, and methods of inhibiting tyrosine kinases, such as, e.g., cell division cycle 2 kinase (Cdc2 kinase), ERK1/2, STAT3, AKT, c-Kit, c-ABL, p60src, VEGFR3, PDGFRα, PDGFRβ, PDGFR-αα, PDGFR-ββ, PDGFR-αβ, FGFR3, FLT-3, FYN oncogene kinase related to SRC, FGR, YES (Fyn), lymphocyte-specific protein tyrosine kinase (Lck), tyrosine kinase with Ig and EGF homology domains (Tie-2), FMS (CSF-IR), KDR, EphA2, EphA3, EphA8, FLT1, FLT4, HCK, PTK5, RET, SYK, DDR1, and DDR2. In some embodiments, the tyrosine kinase is a receptor tyrosine kinase (RTK), such as, e.g., PDGFR, PDGFR-αα, PDGFR-ββ, PDGFR-αβ, or c-Kit, or combinations thereof.

Representative diseases or conditions that may be treated with the crystalline form of Compound 1, or a pharmaceutical composition comprising the same, include, but are not limited to, PAH, primary PAH, idiopathic PAH, heritable PAH, refractory PAH, BMPR2, ALK1, endoglin associated with hereditary hemorrhagic telangiectasia, endoglin not associated with hereditary hemorrhagic telangiectasia, drug-induced PAH, and toxin-induced PAH, PAH associated with or secondary to one or more of systemic sclerosis, mixed connective tissue disease, cancer, refractory cancer, metastatic cancer, neoplasia, hypoplasia, hyperplasia, dysplasia, metaplasia, prosoplasia, desmoplasia, angiogenic disease, pulmonary function disorders, cardiovascular function disorders, HIV infection, hepatitis, portal hypertension, pulmonary hypertension, congenital heart disease, hypoxia, chronic hemolytic anemia, newborn persistent pulmonary hypertension, pulmonary veno-occlusive disease (PVOD), pulmonary capillary hemangiomatosis (PCH), left heart disease pulmonary hypertension, systolic dysfunction, diastolic dysfunction, valvular disease, lung disease, interstitial lung disease, pulmonary fibrosis, schistosomiasis, chronic obstructive pulmonary disease (COPD), sleep-disordered breathing, alveolar hypoventilation disorders, chronic exposure to high altitude, developmental abnormalities, chronic thromboembolic pulmonary hypertension (CTEPH), pulmonary hypertension with unclear multifactorial mechanisms, hematologic disorders, myeloproliferative disorders, splenectomy, systemic disorders, sarcoidosis, pulmonary Langerhans cell histiocytosis, lymphangioleimoyomatosis, neurofibromatosis, vasculitis, metabolic disorders, glycogen storage disease, Gaucher disease, thyroid disorders, tumoral obstruction, fibrosing mediastinitis, and chronic renal failure on dialysis; and diseases such as pulmonary hypertension, congenital heart disease, hypoxia, chronic hemolytic anemia, newborn persistent pulmonary hypertension, pulmonary veno-occlusive disease (PVOD), pulmonary capillary hemangiomatosis (PCH), left heart disease pulmonary hypertension, systolic dysfunction, diastolic dysfunction, valvular disease, lung disease, interstitial lung disease, pulmonary fibrosis, schistosomiasis, chronic obstructive pulmonary disease (COPD), sleep-disordered breathing, alveolar hypoventilation disorders, chronic exposure to high altitude, developmental abnormalities, chronic thromboembolic pulmonary hypertension (CTEPH), pulmonary hypertension with unclear multifactorial mechanisms, hematologic disorders, myeloproliferative disorders, splenectomy, systemic disorders, sarcoidosis, pulmonary Langerhans cell histiocytosis, lymphangioleimoyomatosis, neurofibromatosis, vasculitis, metabolic disorders, glycogen storage disease, Gaucher disease, thyroid disorders, tumoral obstruction, fibrosing mediastinitis, immunological and inflammatory diseases, hyperproliferative diseases, renal and kidney diseases, bone remodeling diseases, metabolic diseases, vascular diseases, and chronic renal failure on dialysis.

In one aspect, the disease or condition is pulmonary arterial hypertension (PAH), and a therapeutically effective amount of the crystalline form of Compound 1 is administered to subject in need thereof. In specific embodiments, the disease or condition is PAH, primary PAH, idiopathic PAH, heritable PAH, refractory PAH, drug-induced PAH, toxin-induced PAH, or PAH with secondary diseases.

The present invention is further illustrated by the following examples, which should not be construed as limiting in any way.

EXAMPLES

Example 1

Preparation of Amorphous Compound 1 (Prior Art)

The synthesis of Compound 1 is disclosed in U.S. Pat. No. 9,815,815 (see Columns 29, line 25 through Col. 31, line 11)

in reference to known synthetic procedures, including those disclosed in WO2008/058341 (corresponding to U.S. Pat. No. 8,461,161). Accordingly, and for purpose of comparison, Compound 1 was prepared by known techniques as follows.

The synthesis of intermediate (S)—N-(3-(1-((6-chloropyrazin-2-yl)amino)ethyl)phenyl)-6-methylnicotinamide is described in Example 1 of U.S. Pat. No. 8,461,161 (see Col. 107, line 64 through Col. 109, line 9). Synthesis of intermediate (S)—N-(3-(1-((6-chloropyrazin-2-yl)amino)ethyl)phenyl)-5-methylnicotinamide (i.e., methyl group of nicotinamide at the 5-position rather than the 6-position) was accomplished by the same procedure, as illustrated in by the following reaction scheme:

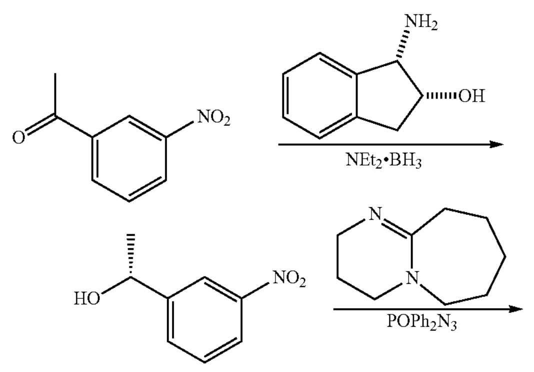

-continued

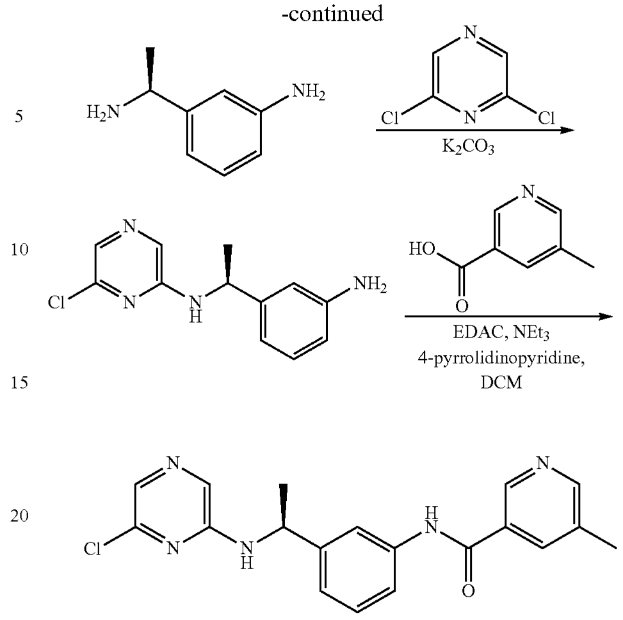

Compound 1 was then prepared via a Suzuki cross-coupling reaction of intermediate (S)—N-(3-(1-((6-chloropyrazin-2-yl)amino)ethyl)phenyl)-5-methylnicotinamide with 3,4-dimethoxyphenyl boronic acid pinacol and purified by column chromatography, as shown by the following reaction scheme:

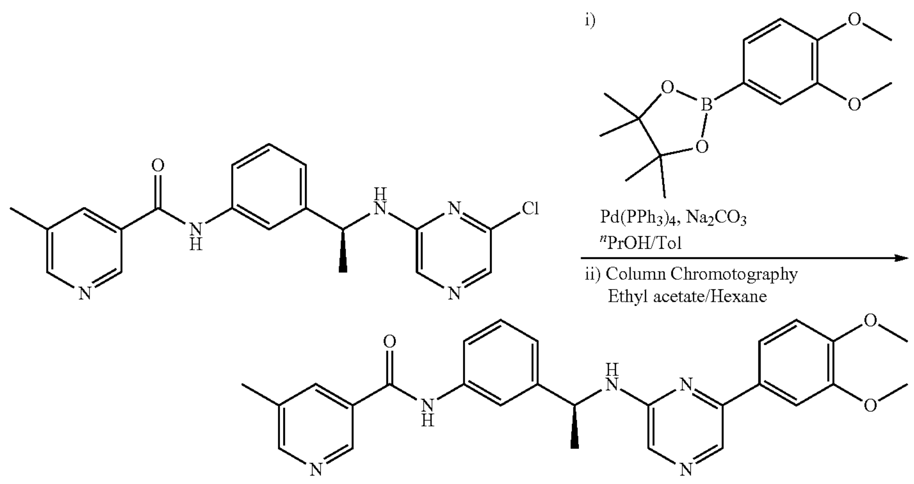

-continued

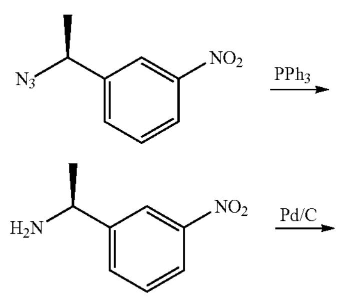

In particular, intermediate (S)—N-(3-(1-((6-chloropyrazin-2-yl)amino)ethyl)-phenyl)-5-methylnicotinamide (crude from previous step; 1.10 kg), 3,4-dimethoxyphenylboronic acid, pinacol ester (0.82 kg) and sodium carbonate solution (0.48 kg in 1.76 L water) were added to a mixture of toluene (8.8 L) and 1-propanol (4.4 L) under nitrogen and agitated for at least 30 minutes. $Pd(PPh_3)_4$ (0.14 kg) was added. The mixture was agitated for at least 10 minutes and then heated to 80±5° C. with agitation, under nitrogen for ≥12 hours. A sample was analyzed by HPLC to confirm the reaction was complete (≤0.50% starting material). Once the reaction was deemed complete, it was cooled to 25±5° C. and filtered. The reaction flask and filter were washed with ethyl acetate and the combined filtrates allowed to separate.

The (upper) organic layer was isolated, washed with water (1×2.75 L) and brine (25% aq Na Cl, 1×2.75 L), dried over anhydrous sodium sulfate (2 kg) and concentrated to dryness (max temp 50° C.) using a rotary evaporator. The resulting solid was re-dissolved in ethyl acetate (2.2 L), Silica MetThiol (Pd scavenger, 0.44 kg) added and the resulting slurry agitated at 20±5° C. for ≥12 hours. Agitation continued until ≤20 ppm Pd was detected (if necessary, additional Silica MetThiol may be added). Once Pd removal was deemed complete, the slurry was filtered, and the filtrate concentrated to dryness (max temp 60° C.) using a rotary evaporator.

| Material | Amount | Molar Equiv |
|---|---|---|
| Compound 1 | 1.10 kg | 1.0 |
| 3,4-Dimethoxyphenylboronic Acid, Pinacol Ester | 0.82 kg | 1.04 |
| Toluene | 8.80 L | — |
| 1-Propanol | 4.40 L | — |
| Sodium Carbonate, Anhydrous | 0.48 kg | — |
| Water for Injection | 4.51 L | — |
| Tetrakis(triphenylphosphine)palladium | 0.139 kg | — |

The crude product was purified by column chromatography: Glass columns packed with silica gel (7 kg/column; 2 columns; 14 kg total) in a slurry with 5:95 (v/v) ethyl acetate, 99%:hexanes (30 L total). Crude product was dissolved in DCM (2 L), and charged to the columns (half to each column). Each column was eluted with 5:95 ethyl acetate, 99%:hexane (10 L/column, 20 L total), followed by 25:75 ethyl acetate, 99%:hexane (30 L/column, 60 L total), followed by 50:50 ethyl acetate, 99%:hexane (30 L/column, 60 L total), followed by 75:25 ethyl acetate, 99%:hexane (30 L/column, 60 L total), and finally with ethyl acetate, 99% (370 L/column, 740 L total). Eluate was collected in 10 L fractions until product elution which was collected in 20 L fractions until product elution was complete. Product containing fraction were combined and concentrated to dryness (max temp 60° C.) using a rotary evaporator. The resulting solid (1.10 kg) was dissolved in dilute hydrochloric acid (0.5N, 7.98 L) maintaining the temperature below 30° C. The product-HCl aqueous solution was slowly added to an aqueous sodium bicarbonate solution (9%, 12.1 L) maintaining the temperature below 30° C. The resulting slurry was agitated for at least 2 hours and the resulting solids collected by filtration through a GMP filter and the filter cake dried in a vacuum oven at ≤50° C., to provide Compound 1 in amorphous form.

Example 2

Characterization of Amorphous Compound 1

Solid state characterization of amorphous Compound 1 (Example 1) was performed via X-Ray Powder Diffraction (XRPD), Differential Scanning calorimetry (DSC) and Fragility and Relaxation Time analyses. The results indicate amorphous Compound 1 forms only a glass and exhibits no crystallization tendency.

I X-Ray Powder Diffraction (XRPD)

Two samples of amorphous Compound 1 were examined by XRPD performed on a Bruker D8-Advance XRPD S/N: 202298, using the following parameters:

| | |
|---|---|
| Configuration: | Theta/theta Bragg Brentano |
| Incident Beam Optics: | Soller slit = 2°; Divergence slit = 0.2 mm; Antiscatter screen = 21 mm |
| Detector Beam Optics: | Soller slit = 2.5° Ni filter; Antiscatter slit = 3 mm |
| Detector: | PSD: Lynx Eye with 1° window |
| Tube: | CuKα λ = 1.5418 Å; Voltage = 40 kV, Current = 40 mA |
| Scan Parameters: | 2-50°2θ. Step size 0.049°2θ. Time per step 1 s |
| Total Scan Time: | 16.5 minutes |

Figure 1:
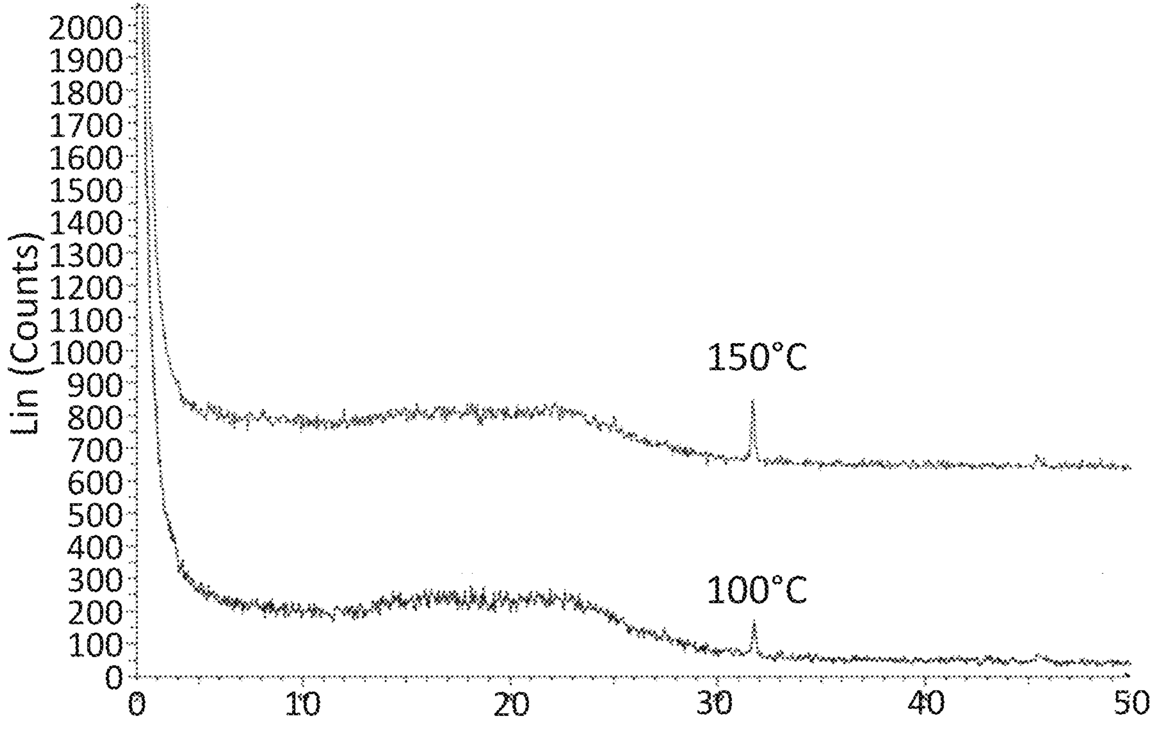
FIG. 1: XRPD of amorphous Compound 1 after heating at 100° C. (lower trace) and 150° C. (upper trace).

The first sample was heated to 100° C. in a DSC pan. It remained a powder with discoloration from white to pale yellow. The sample was covered and placed at −20° C. for ~24 hr, after which it was spread on a Si zero-background plate. Since this sample did not liquefy, a second sample was prepared by sprinkling onto a Si zero-background plate and placing it in an oven at 150° C. for approximately 1 hr until a liquid was observed. The plate was then covered and transferred to a −20° C. freezer for ~24 hr. The XRPD results for the two above samples (100° C. and 150° C.) are provided in FIG. 1, showing them both to be amorphous. The small peaks at ~31.8° 2θ and 45.5° 2θ are believed to be from NaCl, which has its two strongest peaks at these locations.

II Differential Scanning Calorimetry (DSC) and Glass Transition Temperature (Tg)

Samples of amorphous Compound 1 were prepared in Al Tzero pans with standard crimp sealing. An initial DSC assessment to determine Tg and possible crystallization and melting events, was made by:

(1) heating at 10° C./min to 100° C.;
(2) isothermal hold for 5 min;
(3) cooling at 10° C./min to −20° C.;
(4) isothermal hold for 5 min;
(5) heating at 10° C./min to 320° C.;
(6) cooling at 10° C./min to −20° C.; and
(7) heating at 10° C./min to 320° C.

Figure 2:
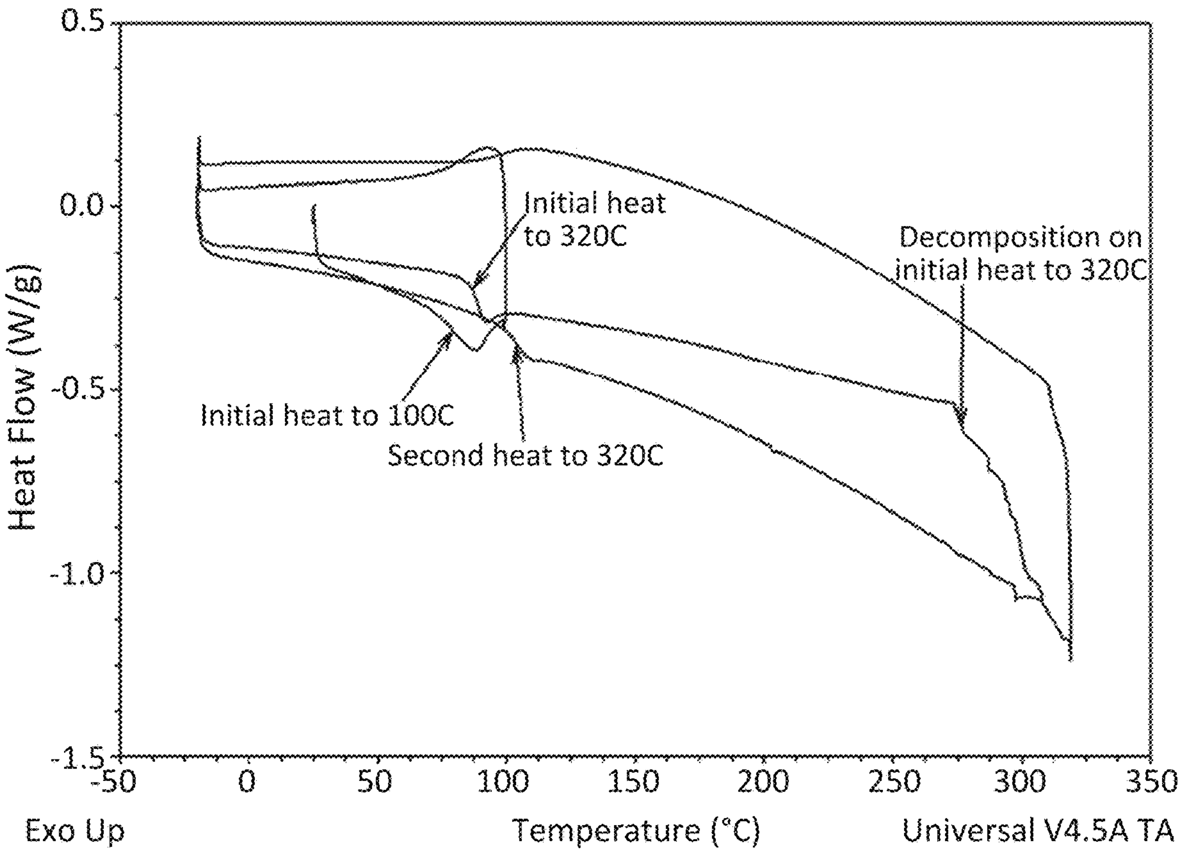
FIG. 2: DSC of amorphous Compound 1, heating to 320° C.

The initial DSC scan is shown in FIG. 2. Decomposition occurred at ~270° C. with no melting peak. Inspection of the DSC pan post-experiment revealed a charred/darkened material. Given a Tg=89° C. (midpoint), the Tm was estimated to be 210° C. (applying a 4/3 factor on a Kelvin scale). The initial DSC test was repeated with a new sample (lowering the upper temperature to 200° C. in steps (5) and (7) to avoid decomposition) and is shown in FIG. 3. Heating to 320° C. and 200° C. with cooling and reheating showed no evidence of crystallization. The first scan to 200° C. is shown in FIG. 4 from which Tg and ΔCp (heat capacity) were obtained: Tg (midpoint)=87.05° C. From ΔCp=0.5066 J/g-K, the configurational heat capacity is estimated to be ΔCp, config=ΔCp/0.9=0.5629 J/g-K.

III $^1H$ and $^1H$-$^{13}C$ Nuclear Magnetic Resonance (NMR)

Figure 5:
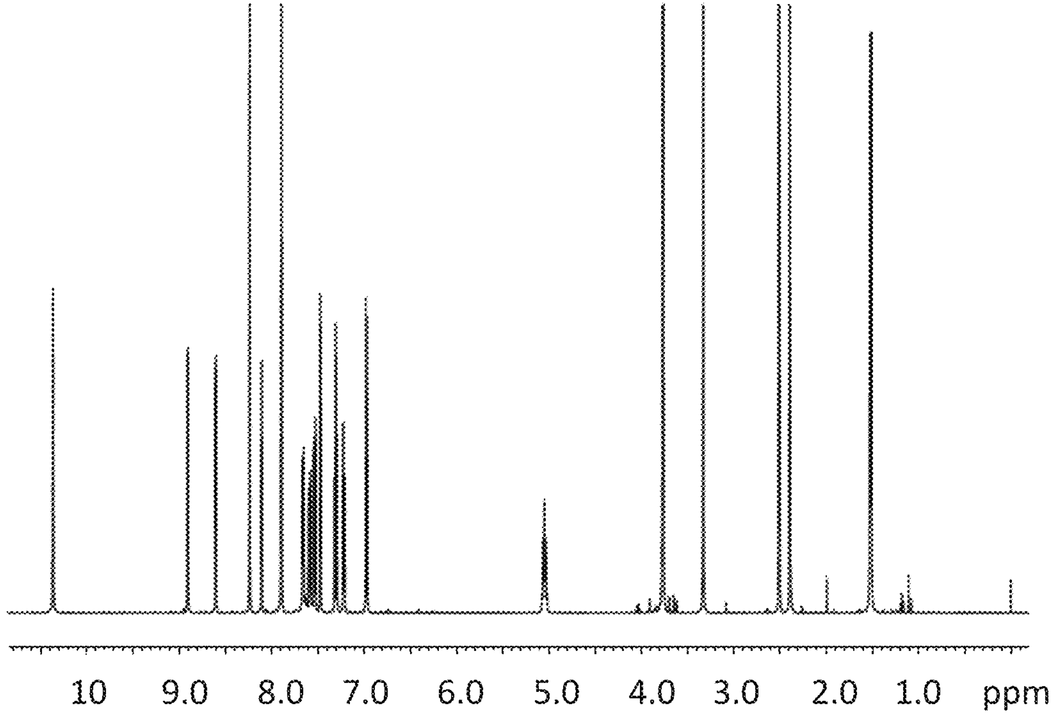
FIG. 5: $^1$H NMR spectrum of amorphous Compound 1.
Figure 6:
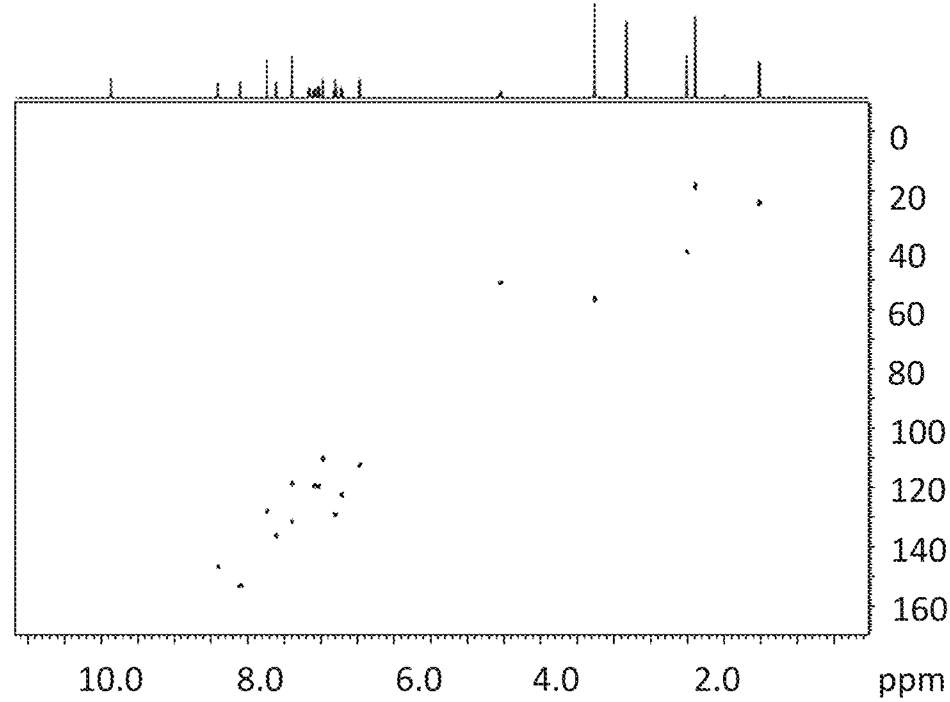
FIG. 6: $^1$H-$^{13}$C Heteronuclear Single Quantum Coherence (HSQC) NMR spectrum of amorphous Compound 1.

NMR experiments were performed on a Bruker A VIIIHD spectrometer equipped with a DCH cryoprobe operating at 500.12 MHz for protons. Experiments were performed in deuterated DMSO and each sample was prepared to ca. 10 mM concentration. The 1H NMR spectrum of Compound 1 is shown in FIG. 5 and is consistent with the chemical structure. Residual (<0.01 equiv.) ethyl acetate peaks (4.04, 1.99 and 1.17 ppm) were present in the sample. The $^1H$-$^{13}C$ Heteronuclear Single Quantum Coherence (HSQC) NMR spectrum is shown in FIG. 6, and is consistent with the chemical structure. Two amine peaks (10.36 and 7.66 ppm, not coupled to C) were observed in the aromatic region. All other peaks correspond to $CH/CH_3$ groups.

IV Solubility

Amorphous Compound 1 (180 mg) was dissolved in 1,4-dioxane (18 mL) and split equally into 18 vials. Test solvent/solvent system (50 μL) was added to the vial and the mixture assessed for dissolution. If no dissolution was apparent, the mixture was heated to ca. 40° C. and reassessed; if dissolution was still incomplete, the cycle was repeated and an additional 50 μL of solvent added. After 300 μL of solvent had been added, 100 μL aliquots were added. This procedure was continued until complete dissolution was observed or until 1 mL of solvent had been added. The solvent solubilities are presented in Table 1; complete dissolution was observed for 13 of 17 solvent systems.

TABLE 1

| Amorphous Compound 1 Solubility | | |
|---|---|---|
| Solvent | Solubility (mg/mL) | ICH Class |
| 2-Propanol | ≥200 | 3 |
| Acetone | ≥200 | 3 |
| Acetonitrile | ≥200 | 2 |
| Chloroform | ≥200 | 2 |
| Ethanol | ≥200 | 3 |
| Ethanol/water (95:5% v/v) | ≥200 | n/a |
| Ethyl acetate | ≥200 | 3 |
| Methanol | ≥200 | 2 |
| Methyl ethyl ketone | ≥200 | 3 |
| Tetrahydrofuran | ≥200 | 2 |
| EtOAc/tBME (75:25% v/v) | ≥200 | n/a |
| EtOAc/tBME (50:50% v/v) | ~100* | n/a |
| EtOAc/tBME (25:75% v/v) | ~12.5* | n/a |
| Heptane | <10 | 3 |
| tert-Butyl methyl ether | <10 | 3 |
| Toluene | <10 | 2 |
| Water | <10 | n/a |

*sample heated to 40° C.

V Fragility and Relaxation Time

Samples of amorphous Compound 1 were prepared in Al Tzero pans with standard crimp sealing. Fragility and relaxation time parameters were determined by measuring Tg as a function of heating rate. Four heating rates were used: 1, 5, 10 and 20° C./min. DSC measurements were made by:

(1) heating at 10° C./min to 100° C.;

(2) isothermal hold for 5 min;

(3) cooling at 10° C./min to −20° C.;

(4) isothermal hold for 5 min; and (5) heating at 10° C./min to 130° C.

The results of the Tg vs. scan rate are provided in Table 2.

TABLE 2

| Amorphous Compound 1 - Fragility and Relaxation Time | | |
|---|---|---|
| Heating rate | Tg (° C.) | Average Tg (° C.) |
| 1° C./min | 84.56 | 84.57 |
| | 84.51 | |
| | 84.64 | |
| 5° C./min | 87.99 | 88.18 |
| | 88.41 | |
| | 88.14 | |
| 10° C./min | 89.01 | 88.87 |
| | 88.82 | |
| | 88.79 | |
| 20° C./min | 91.33 | 91.10 |
| | 91.28 | |
| | 90.68 | |

TABLE 2-continued

| Amorphous Compound 1 - Fragility and Relaxation Time | | |
|---|---|---|
| Scanning rate (q) | ln(q) | Tg (K) |
| 1 | 0 | 357.72 |
| 5 | 1.609438 | 361.33 |
| 10 | 2.302585 | 362.02 |
| 20 | 2.995732 | 364.25 |

Figure 7:
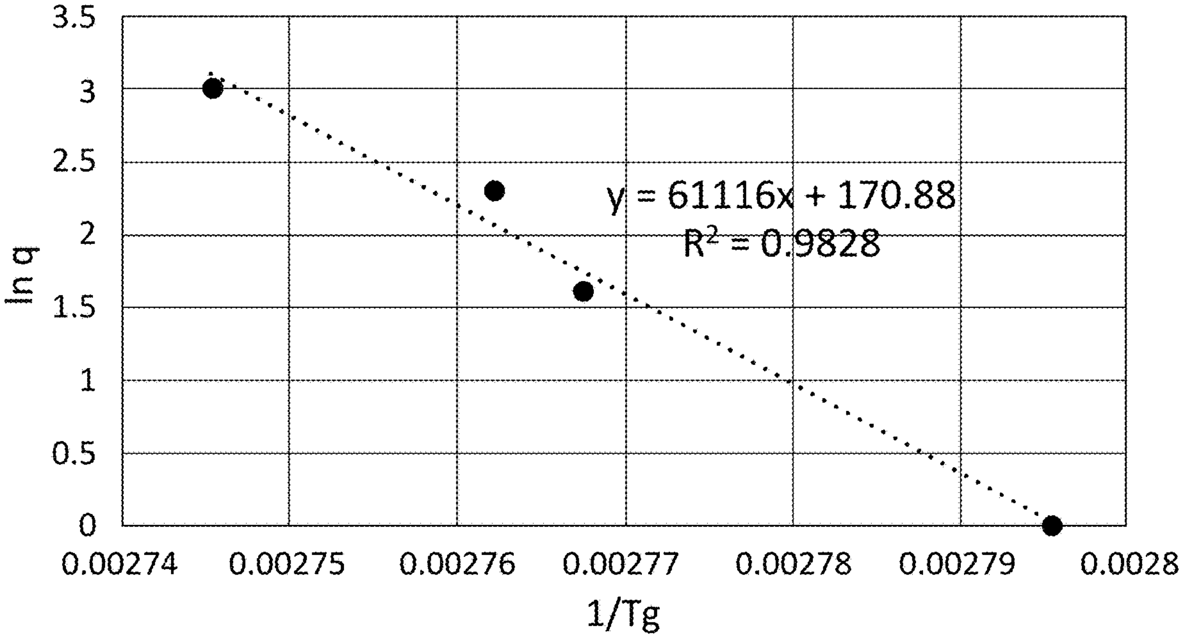
FIG. 7: Plot of heating rate (q) vs. 1/Tg for amorphous Compound 1.

A plot of heating rate (q) vs. 1/Tg of amorphous Compound 1 is shown in FIG. 7. The slope was used to calculate the activation enthalpy (ΔH*), from which the fragility parameters m, D and $T_0$ were calculated, according to the following equations:

$$\Delta H^* = -8.314 \times \text{slope}$$

$$m = \Delta H^* / (2.303 \times 8.314 \times T_g)$$

$$D = 2.303 \times m_{min}^2 / (m - m_{min})$$

$$T_0 = T_g \times (1 - m_{min} / m)$$

$$m_{min} = 16$$

The calculated Fragility parameters are:

$Tg = 362\text{K}$ or $89°$ C. (10° C./min); $\Delta H^* = 508118$ J/mol; $m = 73.3$;

$T_0 = 283\text{K}$ or 10° C.; and $D =$ 10.3 (within the commonly observed range of 7-15 for organic glasses).

Using the fragility parameters, the initial structural relaxation time was calculated according to the following formula, (using γ=0.9 and $\tau_0 = 10^{-14}$ s) and determined to be 3 months at 25° C.

$$\tau = \tau_0 \exp\left(\frac{DT_0}{T - T_0(T/T_g)^\gamma}\right)$$

Example 3

Identification of Crystalline Forms of Compound 1

Experiments were conducted to identify and isolate crystalline forms of Compound 1, including the polymorph screens described below.

Example 3A: Polymorph Screen #1

Amorphous Compound 1 (450 mg) was dissolved in 1,4-dioxane (72 mL) and split equally into 9 vials which were frozen at −50° C., and then freeze dried overnight. Test solvent/solvents (see Table 3 for amounts) was added to the lyophilized material in a vial in an attempt to form a slurry. Slurries/solutions were then thermally cycled (with agitation) for ~72 h, between ambient temperature for 4 h then 40° C. for 4 h, with no specified heat/cool rate. Any solid material remaining post-temperature cycle was isolated by centrifuge filtration and the isolated material analyzed by XRPD. The remaining mother liquors, either post-filtration or if no solid material was present, were split evenly into 3 and subjected to the following:

(a) Evaporation—the cap was removed from the vial to allow solvent evaporation to occur under ambient conditions;

(b) Anti-solvent addition—1 mL of anti-solvent was added (heptane for all samples except acetonitrile and water, where water and THF were used, respectively) and the samples left overnight; and (c) Crash cooling to 5° C. o −18° C. by placing the vial in a freezer.

Any solids isolated were analyzed by XRPD and the results presented in Table 4, which shows most solids isolated from post thermal cycling or drying were crystalline in nature and uniquely crystalline Form A, while any solids recovered from evaporation were amorphous. The cooling or evaporation of mother liquors yielded little solid material, and no solids were isolated via crash-cooling at 5° C. or −18° C.

TABLE 3

Solvents Used in Polymorph Screen

| | Solvent | Vol Added (μL) | Antisolvent | ICH Class |
|---|---|---|---|---|
| 1 | Acetone | 50 | | 3 |
| 2 | Acetonitrile | 50 | | 2 |
| 3 | Chloroform | 50 | | 2 |
| 4 | Ethanol | 50 | | 3 |
| 5 | Ethyl acetate | 200 | | 3 |
| 6 | EtOAc/tBME (50:50% v/v) | 450 | | n/a |
| 7 | Methyl ethyl ketone | 50 | | 3 |
| 8 | tert-Butyl methyl ether | 3000 | | 3 |
| 9 | Water | 3000 | | n/a |
| 10 | 1-Butanol | 200 | Heptane | 3 |
| 11 | Isopropyl Alcohol | 200 | Heptane | 2 |
| 12 | Isopropyl Acetate | 200 | Heptane | 2 |
| 13 | MeOH | 200 | THF | 3 |
| 14 | MIBK | 200 | Heptane | 3 |
| 15 | MeOH/water (40:60% v/v) | 450 | THF | n/a |
| 16 | MeOH/water (80:20% v/v) | 200 | THF | 3 |
| 17 | MeOH/water (95:5% v/v) | 3000 | THF | 3 |
| 18 | EtOH/tBME (25:75% v/v) | 3000 | THF | n/a |

TABLE 4

XRPD Analysis of Isolated Solids

| | Solvent | Solubility Screen | Post-Thermal Cycle | Post-Drying | (a) Evap | (b) Anti-solvent | (c) Cooling (5° C.) | (c) Cooling (-18° C.) |
|---|---|---|---|---|---|---|---|---|
| 1 | Acetone | — | A | A | — | Am | — | — |
| 2 | Acetonitrile | — | A | A | — | — | — | — |
| 3 | Chloroform | — | — | — | — | Am | — | — |
| 4 | Ethanol | — | A | A | Am* | A | — | — |
| 5 | Ethyl Acetate | A | A | A | — | — | — | — |
| 6 | EtOAc:tBME (50:50% v/v) | A | A | A | Am | — | — | — |
| 7 | Methyl Ethyl Ketone | — | A | A | Am* | A | — | — |
| 8 | tert-Butyl Methyl Ether | Am | A | A | — | — | — | — |
| 9 | Water | Am | Am | Am | — | — | — | — |
| 10 | 1-Butanol | NM | A | A | Am | A | — | — |
| 11 | 2-Propanol | — | A | A | Am | — | — | — |
| 12 | Isopropyl acetate | NM | A | A | — | Am | — | — |
| 13 | Methanol | A | — | — | Am | — | — | — |
| 14 | Methyl iso-butyl ketone | NM | A | A | Am | A | — | — |
| 15 | MeOH:water (40:60% v/v) | NM | Am | Am | — | — | — | — |
| 16 | MeOH:water (80:20% v/v) | NM | — | — | Am | — | — | — |
| 17 | MeOH:water (95:5% v/v) | NM | — | — | Am | — | — | — |
| 18 | EtOH:tBME (25:75% v/v) | Am | — | — | — | — | — | — |

A = Form A

Am = Amorphous solid

NM = Not measured

— = No solid

*Dried in a vacuum oven (40° C., 3 h) post-evaporation

Evaporation:

Evaporation of ethyl acetate, methanol and EtOAc/BME (50:50) produced crystalline Form A. Amorphous solids were isolated from BME, water and 75:25 EtOAc/BME. Weak Form A peaks were observed in the diffractogram of the solid isolated from EtOAc/BME (25:75).

Post-Thermal Cycling:

Crystalline Form A was produced from acetonitrile, ethyl acetate, ethyl acetate/BME (50:50% v/v), BME, 1-butanol, 2-propanol, isopropyl acetate and MIBK. Amorphous solid was isolated from water and MeOH/water (40:60% v/v). All other solvent systems (acetone, chloroform, ethanol and MEK) provided only solutions (no solid material) after thermal cycling. Therefore, new samples were prepared using a lower solvent volume, which after thermal cycling provided solids from acetone, ethanol and MEK which were confirmed to be crystalline Form A.

Post-Drying:

All crystalline solids were unchanged after drying. The amorphous solid isolated from water appeared to produce some weak peaks indicative of crystalline Form A on drying indicating partial re-crystallization.

Evaporation:

Amorphous solids were isolated upon evaporation of ethyl acetate, EtOAc/BME (50:50% v/v), 1-Butanol, IPA, MeOH, MIBK, MeOH/water (80:20% v/v) and MeOH/water (95:5% v/v). Evaporation of all other samples provided only viscous oils, which were dried in a vacuum oven (40° C., 3 h). Amorphous solid material was isolated from ethanol and MEK.

Antisolvent Addition:

When an antisolvent was added to the mother liquors, precipitation was noted in all solvent systems except water. After standing under ambient conditions for 24 h, solid material was isolated from acetone, chloroform, ethanol, MEK, IBME, 1-BuOH, isopropyl acetate and MIBK. Crystalline Form A was produced from ethanol, MEK, butanol and MIBK when heptane was added as an antisolvent. Amorphous solids were produced from acetone, chloroform, tBME and isopropyl acetate when heptane was added as an antisolvent.

Crash Cooling:

When mother liquors were cooled post-thermal cycling to 5° C. for 72 h, none of the samples provided solid material. Further cooling to −18° C. for 72 h also resulted in no solid material.

Example 3B: Polymorph Screen #2

Dissolution in Ethanol

Amorphous Compound 1 was dissolved in ethanol (6 mL/g) and stirred at room temperature. Aliquots were removed after 24 and 48 hours and analyzed by XRPD, showing them to be identical to starting material. Water (0.02 mL) was then added to the suspension. After 72 h the solid obtained was pure crystalline Form B. The XRPD traces are show in FIG. 2.

Example 3C: Polymorph Screen #3

Solvent Screen

Compound 1 (80 mg) was suspended in various solvents/water solvent mixtures, as show in Table 5. Dissolution was observed in methanol, acetone and THF. Water was added to the samples, which were then stirred for 24 h at room temperature, filtered under vacuum and the isolated solids analyzed by XRPD. The results are summarized in Table 5 and show pure crystalline Form B was isolated from ethanol, while all others showed no change in form from the starting material.

TABLE 5

Conditions and XRPD Results for Solvent Screen

| Solvent | Volume (mL/g) | Observation | Solid Form |
|---|---|---|---|
| Starting Material | — | — | A + Minor B |
| Ethanol | 7.5 | Suspension | B |
| Toluene | 10 | Suspension | A + Minor B |
| iPropanol | 10 | Suspension | A + Minor B |
| Acetonitrile | 7.5 | Suspension | A + Minor B |
| Ethyl acetate | 10 | Suspension | A + Minor B |
| THF | 4 | Solution | N/A |
| Acetone | 7.5 | Solution | N/A |
| Methanol | 2.5 | Solution | N/A |
| Methanol/water (1/1) | 5 | Oil | N/A |
| Acetone/water (1/2) | 22.5 | Oil | N/A |
| THF/water (1 1) | 8 | Suspension | A + Minor B |
| Ethanol/water (1/1) | 7.5 | Suspension | A + Minor B |
| iPropanol/water (1/1) | 7.5 | Suspension | A + Minor B |
| Acetonitrile/water (1/2) | 15 | Suspension | A + Minor B |

A = Form A
B = Form B

Example 3D: Polymorph Screen #4

Solid Compound 1 (200 mg) was suspended in each of the following:

- a mixture of ethyl acetate/n-heptane 1/1 (5 mL/g)+1% water at room temp;
- a mixture of ethyl acetate/n-heptane 1/1 (5 mL/g)+1% water at 60° C.;
- ethyl acetate (2.5 L/Kg)+2% water at 60° C.; and
- a mixture of ethanol-water 3/7 (5 mL/g) at 60° C.

The suspensions were stirred for 24 h and then filtered under vacuum. The resulting solids were analyzed by XRPD. Table 6 summarizes the conditions and results. Mixtures of ethyl acetate with n-heptane resulted in non-homogeneous suspensions. No changes were observed after 24 hours and the solids obtained were the same as the original mixture of polymorphs. Ethyl acetate only (+2% water) resulted in dissolution of solids. More solid was added until a suspension was achieved. After 24 h at 60° C. a thick suspension was obtained. The resulting solid was Form B with traces of Form A. Using ethanol, partial solution was observed. Addition of water (0.5 Kg/L) resulted in the formation of a precipitate, which was isolated and found to be pure Form B.

TABLE 6

Conditions and XRPD Results for Secondary Solvent Screen

| Solvent | Volume (mL/g) | Observation | Solid Form |
|---|---|---|---|
| — | — | — | A + Minor B |
| EtOAc/n-heptane (1% $H_2O$) | 5 | Non-homogenous | A + Minor B |
| EtOAc/n-heptane (1% $H_2O$) | 5 | Non-homogenous | A + Minor B |
| EtOAc (2% $H_2O$) | 2.5 | Dissolution/suspension | B + Trace A |
| EtOH/$H_2O$ | 5 | Partial solution/Suspension | B |

Example 4

Comparative Properties of Crystalline Forms a and B

I XRPD

X-Ray Powder Diffractograms (XRPD) were obtained on a PANalytical X'Pert Pro, using Datacollector Software, with a 3152/63 Focusing X-ray mirror and a Pixcel Detector. The instrument conditions are provided below:

| Instrument | Description |
|---|---|
| Radiation Source | Cu K Alpha |
| Configuration | Transmission |
| Tube Power | 45 kV 40 mA |
| Incident beam divergence slit | 0.5° |
| Incident beam antiscatter slit | 0.5° |
| Diffracted beam antiscatter slit | 2.0 mm |
| Soller slits | 0.02 rad |
| Step size | 0.013° |
| Time/step | 77.5 s |
| Scan range | 2-40° 2θ for 7910;<br>2-50° 2θ for 8500 |

Figure 10:
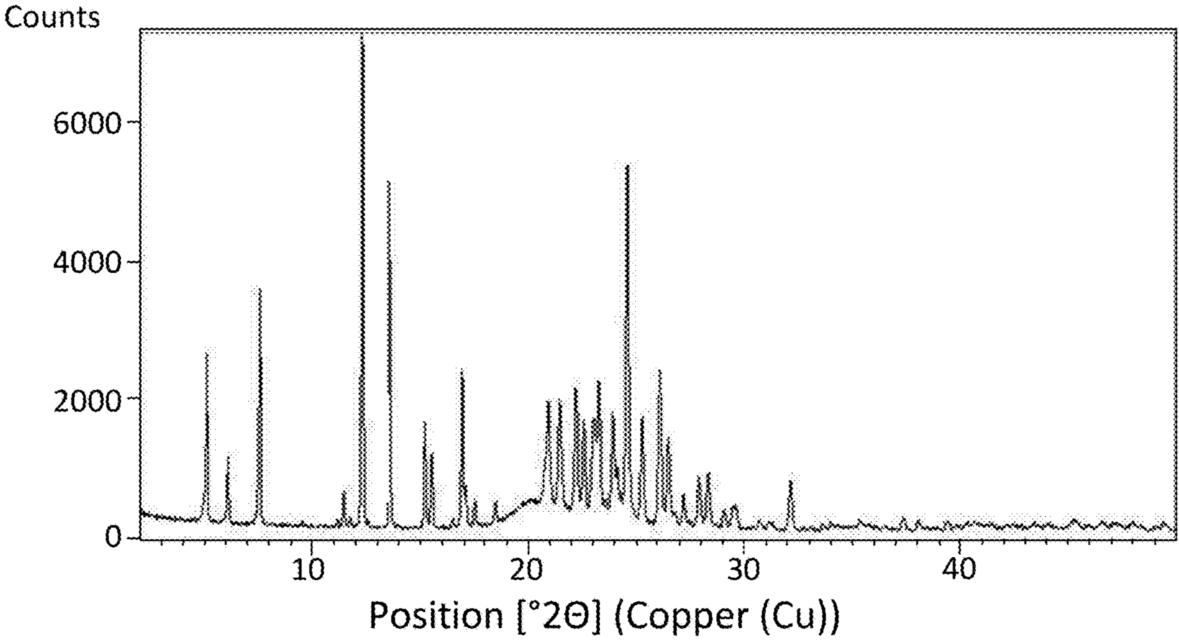
FIG. 10: XRPD of Compound 1, Form B.

The XRPD of crystalline Form A of Compound I as obtained in is shown in FIG. 3. The XRPD of crystalline Form B of Compound I as obtained in is shown in FIG. 10. Table 7 lists the diffractogram peaks for Form A (left columns) and Form B (right columns).

TABLE 7

Listing of XRPD Peaks - Form A (left columns) and Form B (right columns)

| Peak Position [°2θ] | Height [cts] Form A | Relative intensity [%] | Peak Position [°2θ] | Height [cts] Form B | Relative intensity [%] |
|---|---|---|---|---|---|
| 5.5 | 4572 | 24.1 | 5.2 | 2405 | 33.4 |
| 7.8 | 6751 | 35.6 | 6.1 | 966 | 13.4 |
| 11.0 | 5150 | 27.2 | 7.6 | 3378 | 46.9 |
| 12.3 | 18949 | 100.0 | 11.5 | 539 | 7.5 |
| 15.6 | 569 | 3.0 | 12.3 | 7207 | 100.0 |
| 16.6 | 1947 | 10.3 | 13.6 | 4971 | 69.0 |
| 17.5 | 2382 | 12.6 | 15.2 | 1530 | 21.2 |
| 19.4 | 1729 | 9.1 | 15.6 | 1076 | 14.9 |
| 20.0 | 2564 | 13.5 | 17.0 | 2283 | 31.7 |
| 20.4 | 844 | 4.5 | 17.6 | 379 | 5.3 |
| 21.1 | 601 | 3.2 | 18.5 | 300 | 4.2 |
| 21.7 | 2022 | 10.7 | 21.0 | 1682 | 23.4 |
| 22.1 | 1357 | 7.2 | 21.5 | 1686 | 23.4 |
| 22.9 | 1043 | 5.5 | 22.2 | 1870 | 26.0 |
| 23.4 | 6148 | 32.5 | 22.6 | 1378 | 19.1 |
| 24.0 | 2399 | 12.7 | 23.0 | 1344 | 18.7 |
| 24.8 | 530 | 2.8 | 23.3 | 1927 | 26.7 |
| 25.4 | 964 | 5.1 | 23.9 | 1443 | 20.0 |
| 25.9 | 1266 | 6.7 | 24.6 | 5142 | 71.3 |
| 26.4 | 1428 | 7.5 | 25.3 | 1512 | 21.0 |
| 27.1 | 1142 | 6.0 | 26.1 | 2190 | 30.4 |
| 27.8 | 910 | 4.8 | 26.5 | 1183 | 16.4 |
| 28.3 | 593 | 3.1 | 27.2 | 435 | 6.0 |
| 28.8 | 2073 | 10.9 | 27.9 | 695 | 9.7 |
| 30.0 | 374 | 2.0 | 28.3 | 767 | 10.6 |
| 32.0 | 289 | 1.5 | 29.5 | 305 | 4.2 |
| 37.5 | 78 | 0.4 | 32.2 | 512 | 7.1 |

II Differential Scanning calorimetry

Figure 11:
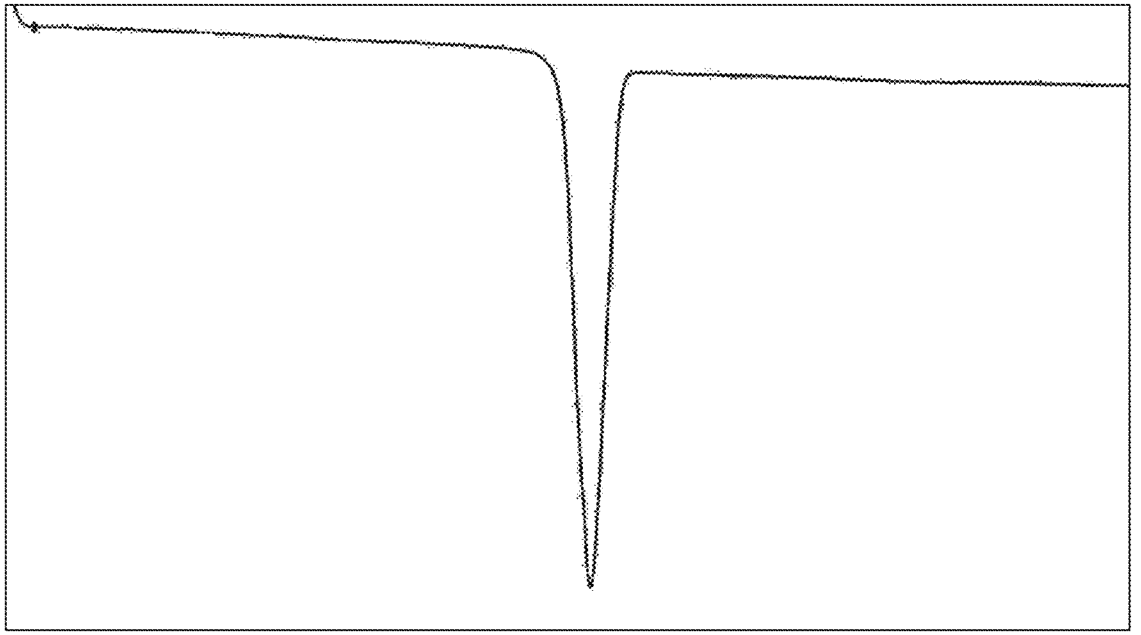
FIG. 11: DSC curve Compound 1, Form A.

Differential Scanning calorimetry (DSC) was performed on a Mettler Toledo 823E instrument, using STARe V15.00 Software, with an Aluminium (40 μL) pan and cover, at a temperature range of 35-250° C. (10° C./min) and using Nitrogen (60 ml/min) as the purge gas. The DSC curves are shown in FIG. 11 (crystalline Form A) and 12 (crystalline Form B).

III TGA

Figure 8:
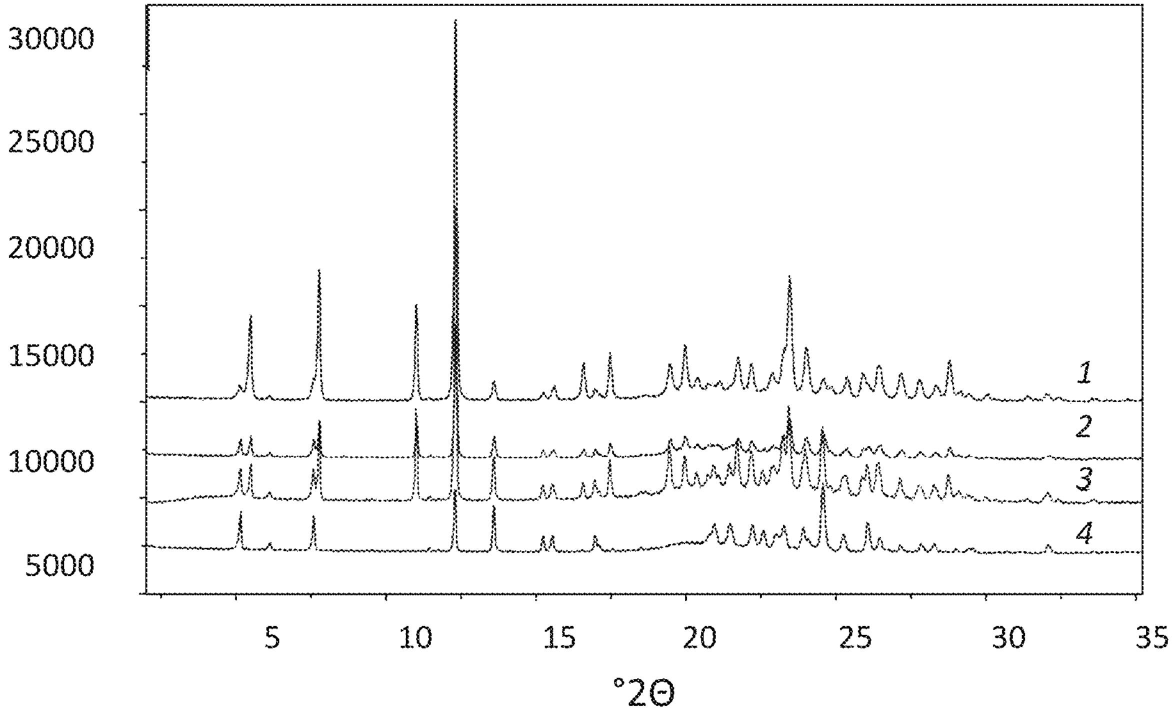
FIG. 8: X-Ray Powder Diffractogram (XRPD) comparison for the ethanol slurry described in Example 3B (crystalline Form B): Starting material (upper trace 1), after 24 hours (2), after 24 hours (3) and after addition of water and 72 hours (lower trace 4).

TGA thermograms of crystalline Forms A and B of Compound 1 were obtained using a Mettler Toledo TGA/DSC 3+(Software: STARe V16.00), using an Aluminium (100 μL) pan, at a temperature range of 35-250° C. (10° C./min) and using Nitrogen (50 ml/min) as the purge gas. The TGA thermogram of crystalline Form A of Compound 1 is shown in FIG. 7, while the TGA thermogram of crystalline Form B of Compound 1 is shown in FIG. 8.

IV Infra Red

Figure 9:
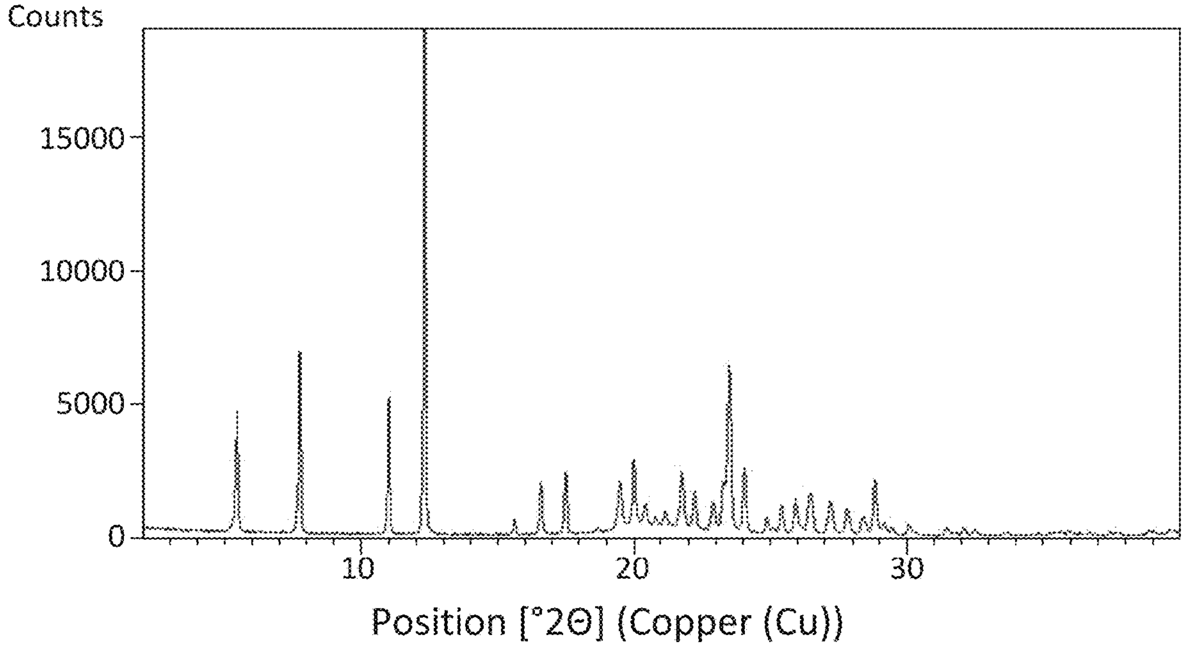
FIG. 9: XRPD of Compound 1, Form A.

The infra-red spectrum of crystalline Form A of Compound 1 was recorded on a Perkin Elmer Spectrum 2, using a MIR source, LiTa03 detector and OptKBr beam splitter, with a Universal ATR Diamond accessory. The infra-red spectrum of crystalline Form B of Compound 1 was recorded on a Perkin Elmer Spectrum 100, using a MIR source, LiTa03 detector and OptKBr beam splitter, with a Universal ATR Diamond/ZnSe Accessory. In both cases, 4 scans were collected at a 0.2 scan rate and resolution of 4, with a 4000-650 $cm^{-1}$ spectrum range. The infra-red spectrum of crystalline Form A of Compound 1 is shown in FIG. 9. The infra-red spectrum of crystalline Form B of Compound 1 is shown in FIG. 10. Table 8 lists the major IR peaks for Form A (left columns) and Form B (right columns).

TABLE 8

Major IR Peak (ranked by intensity) for Crystalline Forms A and B

| | Form A | | Form B | |
|---|---|---|---|---|
| Peak # | X ($cm^{-1}$) | Y (% T) | X ($cm^{-1}$) | Y (% T) |
| 1 | 1028.81 | 71.19 | 1537.94 | 41.28 |
| 2 | 808.11 | 69.72 | 1223.67 | 40.70 |
| 3 | 1165.17 | 67.97 | 847.14 | 37.44 |
| 4 | 1203.49 | 67.92 | 1203.51 | 36.42 |
| 5 | 1434.61 | 67.49 | 803.19 | 36.06 |
| 6 | 1419.00 | 66.76 | 1432.23 | 34.71 |
| 7 | 1271.02 | 66.60 | 1030.05 | 32.11 |
| 8 | 1227.21 | 64.14 | 1135.88 | 27.28 |
| 9 | 1178.07 | 59.81 | 1499.39 | 26.06 |
| 10 | 1504.82 | 54.91 | 1264.98 | 25.69 |

V Slurries in Ethyl Acetate at Various Temperatures

Figure 12:
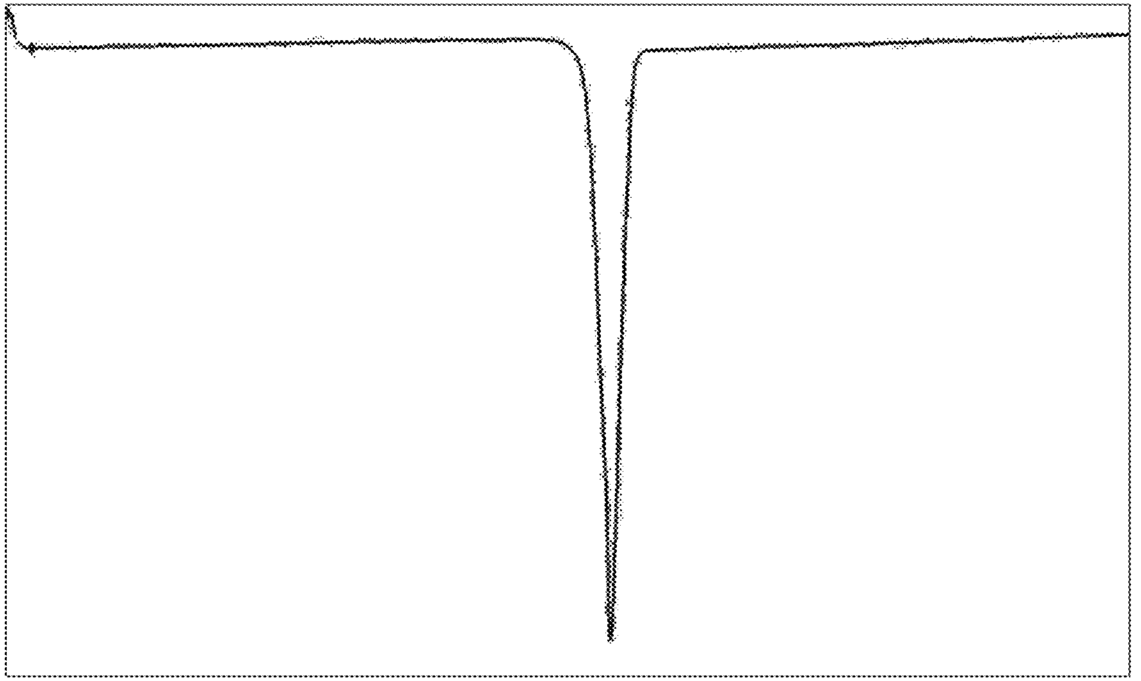
FIG. 12: DSC curve Compound 1, Form B.
Figure 13:
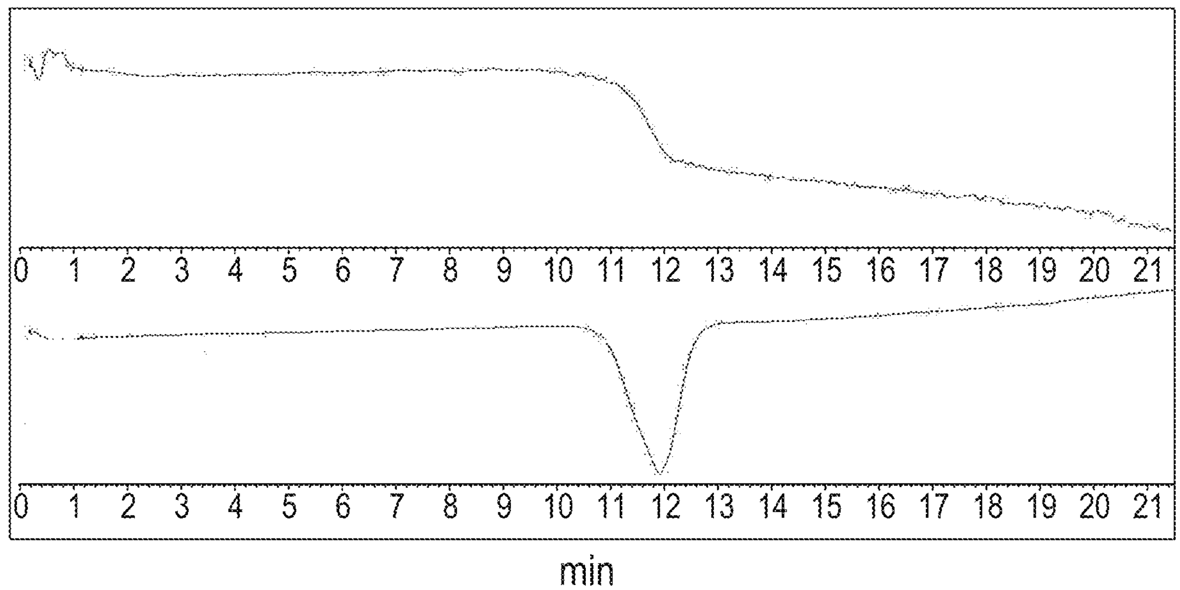
FIG. 13: TGA thermogram Compound 1, Form A.

Starting material was crystalline Form A of Compound 1, containing very small amounts of crystalline Form B. This material was slurried in ethyl acetate and stirred under the conditions of time, volume and temperature as shown in Table 9 (note—the experiment conducted at 60° C. resulted in complete dissolution and is not listed in Table 9). The mixtures at lower temperatures (10° C. and room temperature) showed very slow conversion of crystalline Form A to Form B. At higher temperature (45° C.) after 89 h pure form B was obtained. FIGS. 11, 12 and 13 show the XRPD for each slurry (at 10° C., RT and 45° C. respectively) compared with the starting material and the pure polymorphs; the results are summarized in Table 9.

TABLE 9

| Ethyl Acetate Slurries of Crystalline Compound 1 | | | |
|---|---|---|---|
| Temp | Volume | Time | Form |
| 10° C. | 15 mL/g | 52 h | A + B |
| | | 73 h | A (minor) + B (major) |
| | | 145 h | A (minor) + B (major) |
| RT | 10 mL/g | 24 h | A + B |
| | | 96 h | A (minor) + B (major) |
| | | 117 h | A (minor) + B (major) |
| | | 189 h | A (minor) + B (major) |
| 45° C. | 5 mL/g | 16 h | A + B |
| | | 66 h | B + A (minor) |
| | | 87 h | B |

VI Solubility Study

Figure 14:
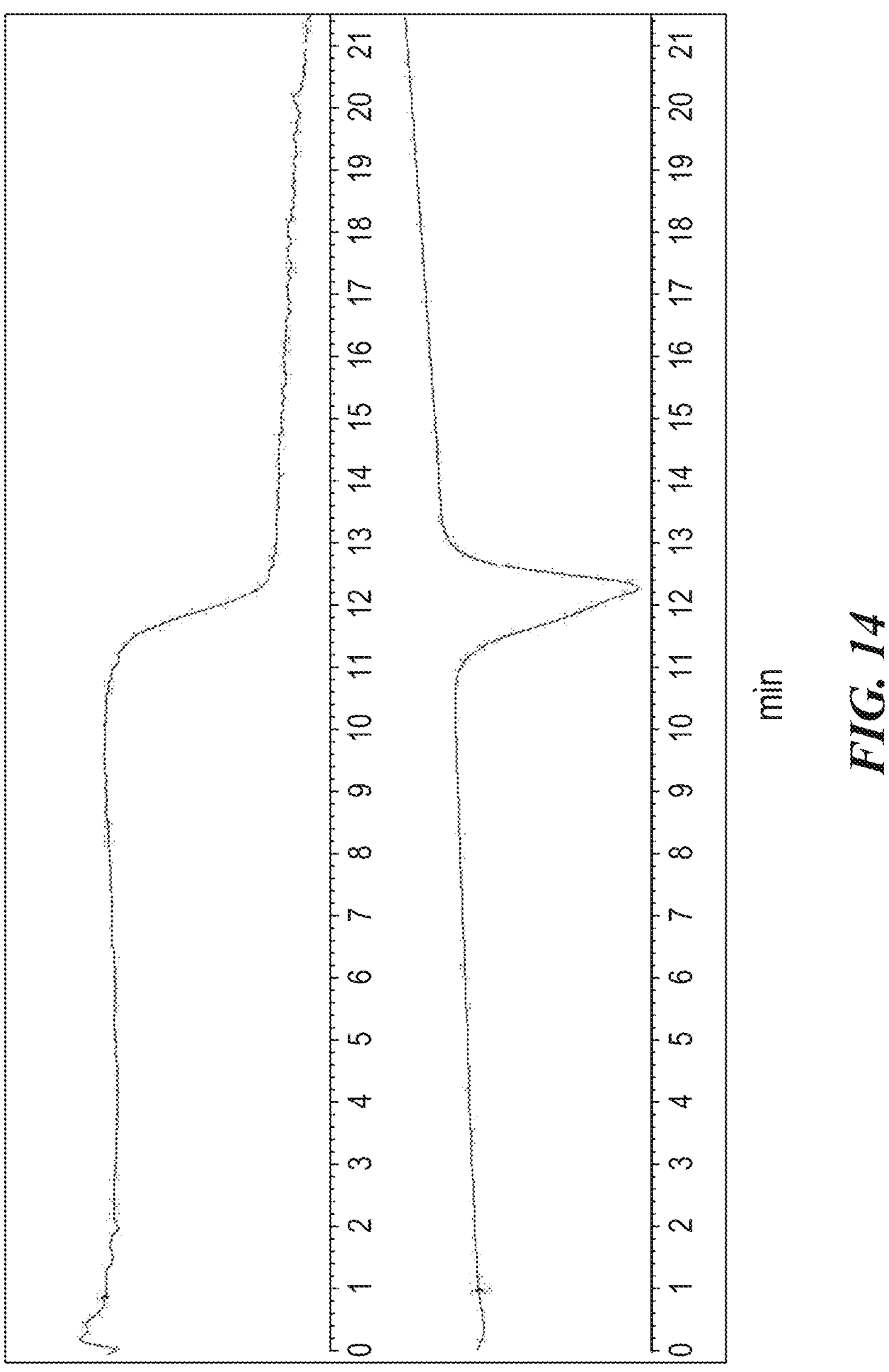
FIG. 14: TGA thermogram Compound 1, Form B.
Figure 15:
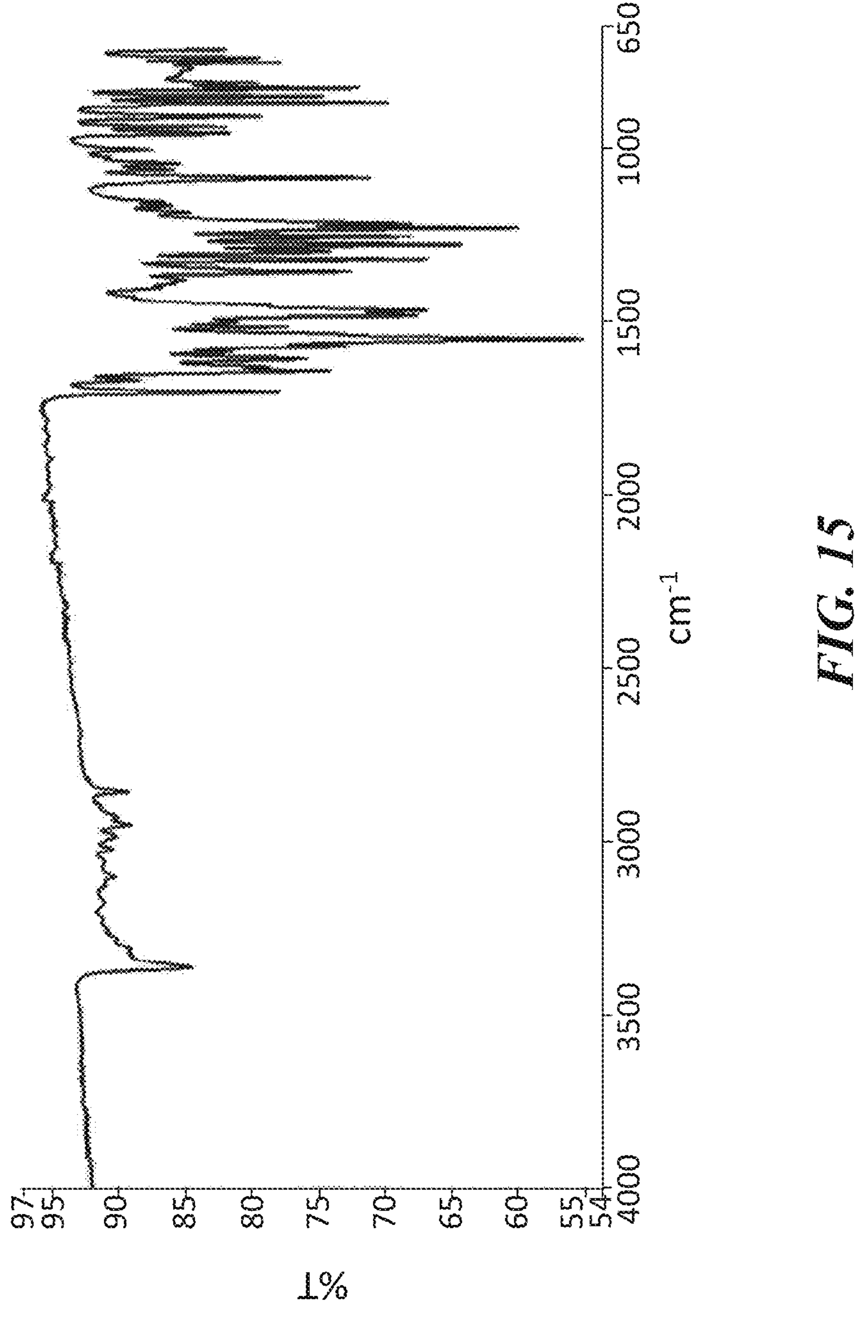
FIG. 15: Infra-red Spectrum of Compound 1, Form A
Figure 16:
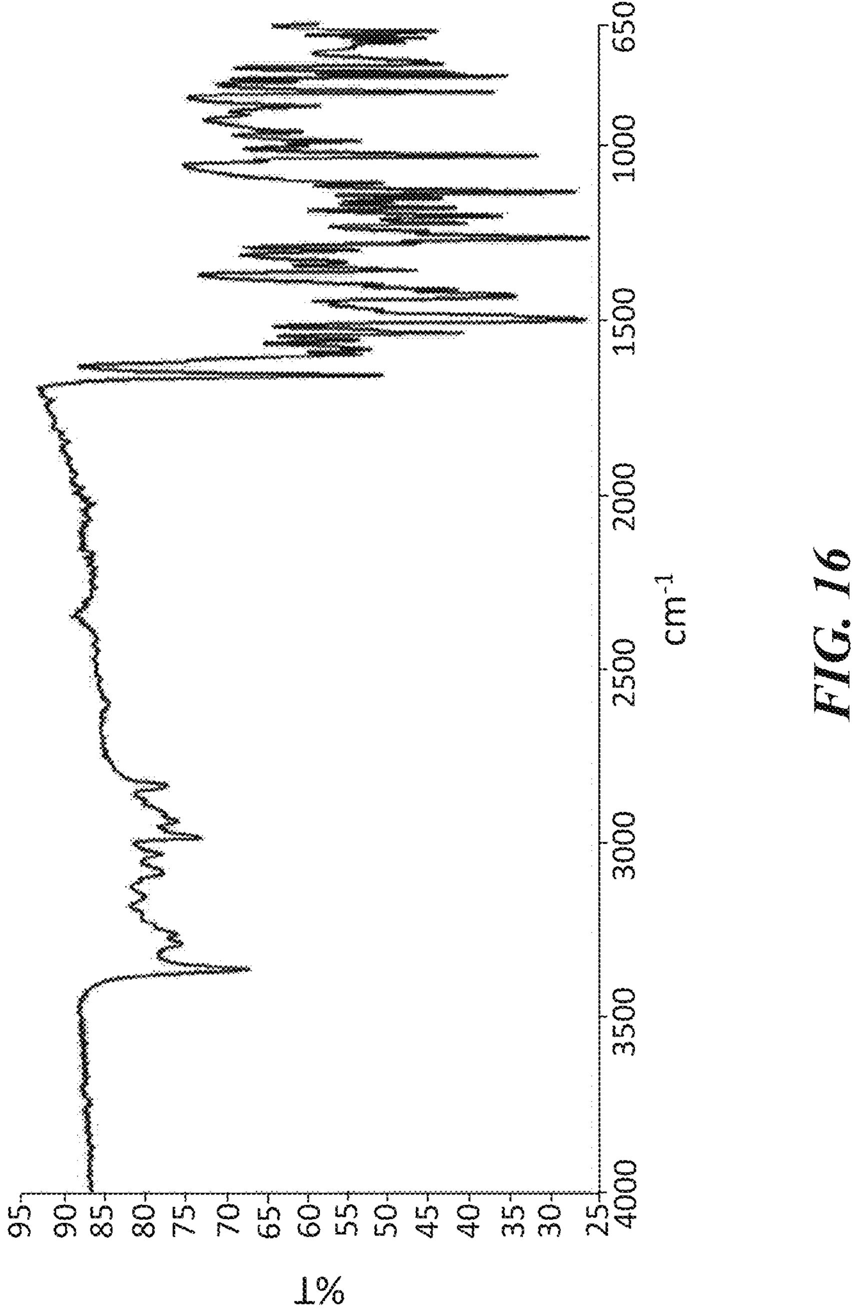
FIG. 16: Infra-red Spectrum of Compound 1, Form B
Figure 17:
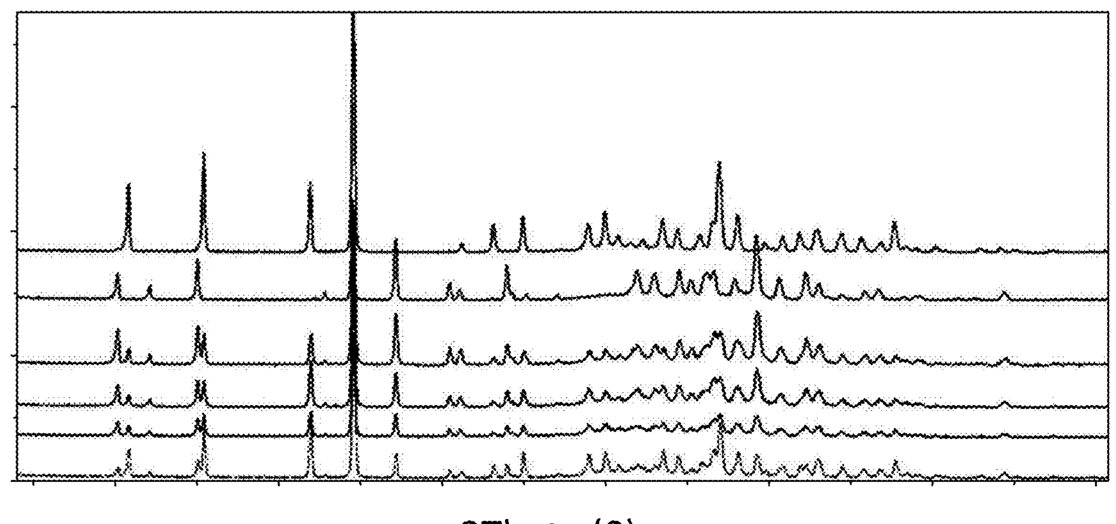
FIG. 17: XRPDs of slurries of crystalline form A of Compound 1 in ethanol at 10° C.
Figure 18:
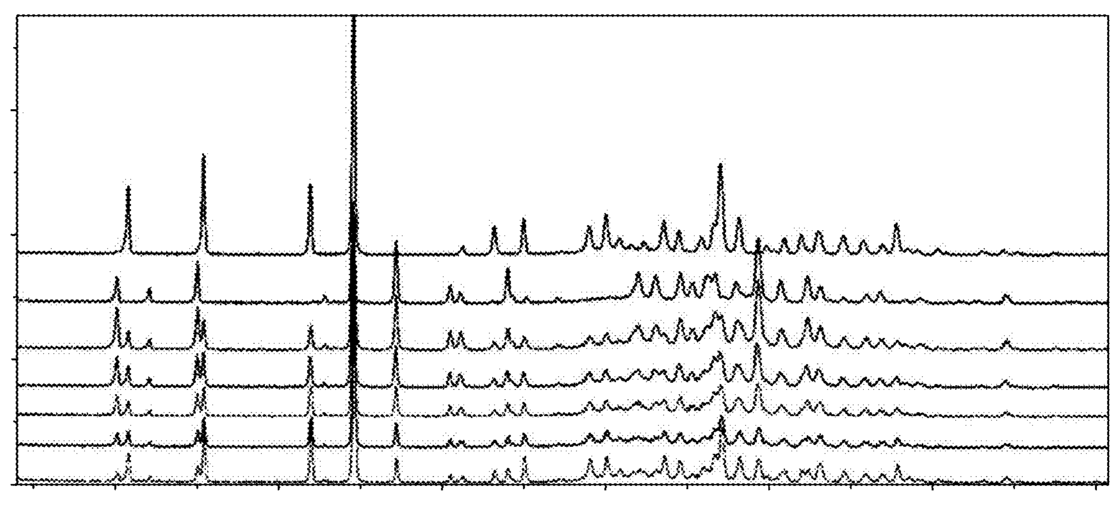
FIG. 18: XRPDs of slurries of crystalline form A of Compound 1 in ethanol at RT.
Figure 19:
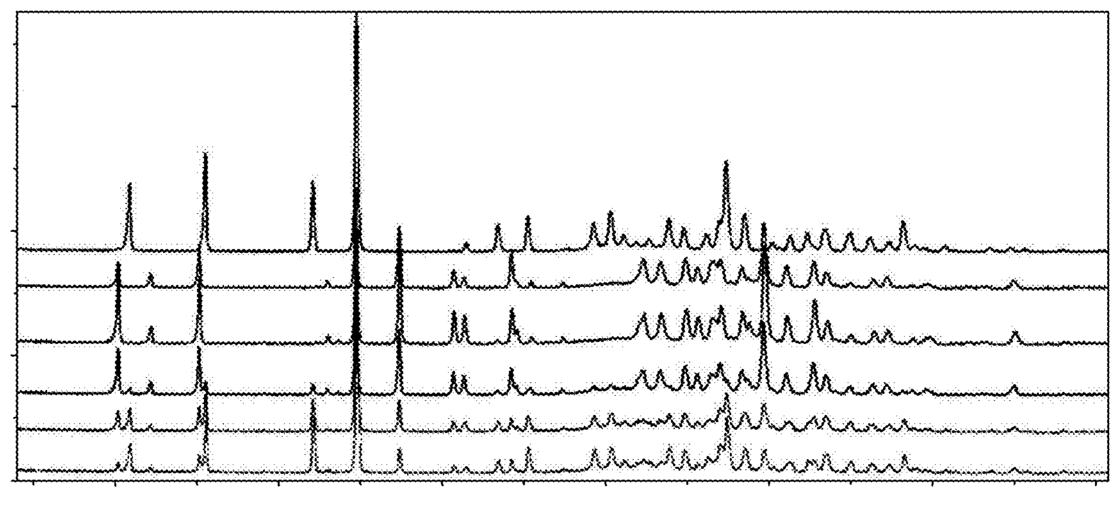
FIG. 19: XRPDs of slurries of crystalline form A of Compound in ethanol at 45° C.
Figure 20:
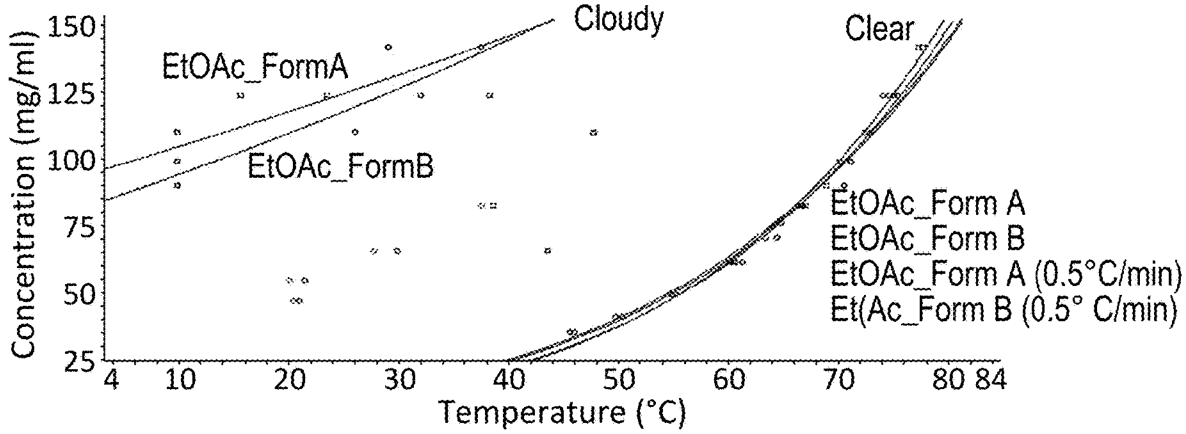
FIG. 20: Solubility curves (mg/mL vs temp) in ethyl acetate±water for crystalline Forms A and B of Compound 1.
Figure 21:
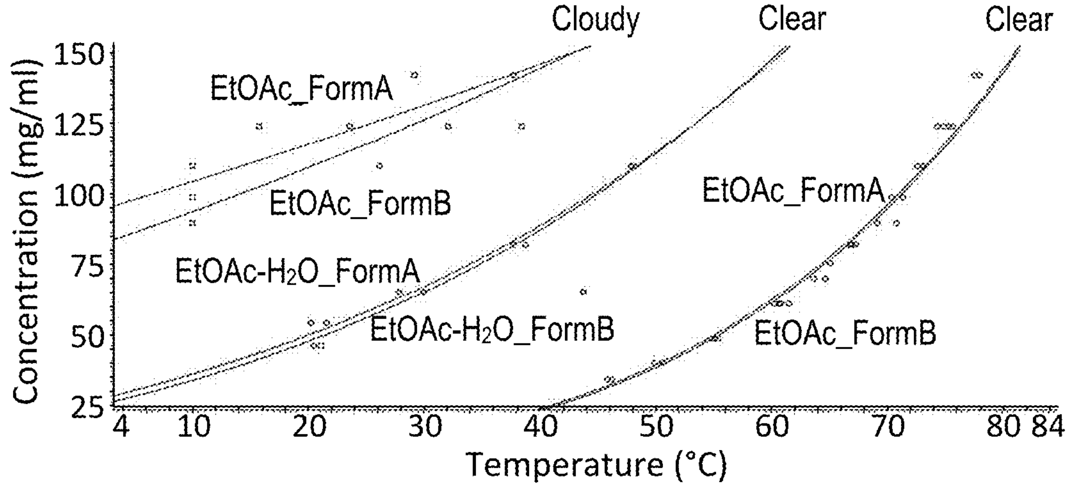
FIG. 21: Comparison of solubility curves of crystalline Forms A and B of Compound 1.

The solubility of crystalline Forms A and B of Compound 1 in ethyl acetate was determined using a Crystal16® parallel crystallizer. Two heating rates were used, 1° C./min and 0.5° C./min. The suspensions were heated to 78° C. and cooled to 10° C. at 0.2° C./min and maintained for 2 h at 10° C. FIG. 14 shows the solubility curves obtained (concentration in mg/mL vs Temperature) demonstrating the solubility is similar for both crystallines Form A and B. The solubility was also determined in ethyl acetate+2% water. The suspensions were heated to 78° C. at 1° C./min, cooled to 10° C. at 0.2° C./min and maintained for 2 h at 10° C. FIG. 15 compares the resulting solubility curve with the pure ethyl acetate. The results demonstrate that crystalline Forms A and B have similar solubilities in ethyl acetate+2% water and are significantly more soluble in the presence of water (2%), as compared to pure ethyl acetate. In both systems, crystalline Form B is slightly less soluble.

VII DSC and TGA of Form A and Form B

Crystalline Forms A and B of Compound 1 were analyzed by DSC and TGA; Table 10 shows the results. DSC and TGA analyses indicate crystalline Form B is an anhydrous polymorph. Crystalline Form B has a slightly higher melting point and slightly lower fusion enthalpy, suggesting the two polymorphs are entropically related.

TABLE 10

| DSC and TGA Analysis of Crystalline Forms A and B | | | | | |
|---|---|---|---|---|---|
| Form | Onset (° C.) | DSC Peak (° C.) | Fusion Enthalpy (J/g) | 1st loss | TGA 2nd loss |
| A Dried | 142.47 | 147.24 | 86.05 | no loss | 0.18% under melting |
| B Dried | 146.35 | 150.29 | 82.98 | no loss | 0.27% under melting |

VII TGA of a Mixture of Crystalline Forms A & B

Figure 22:
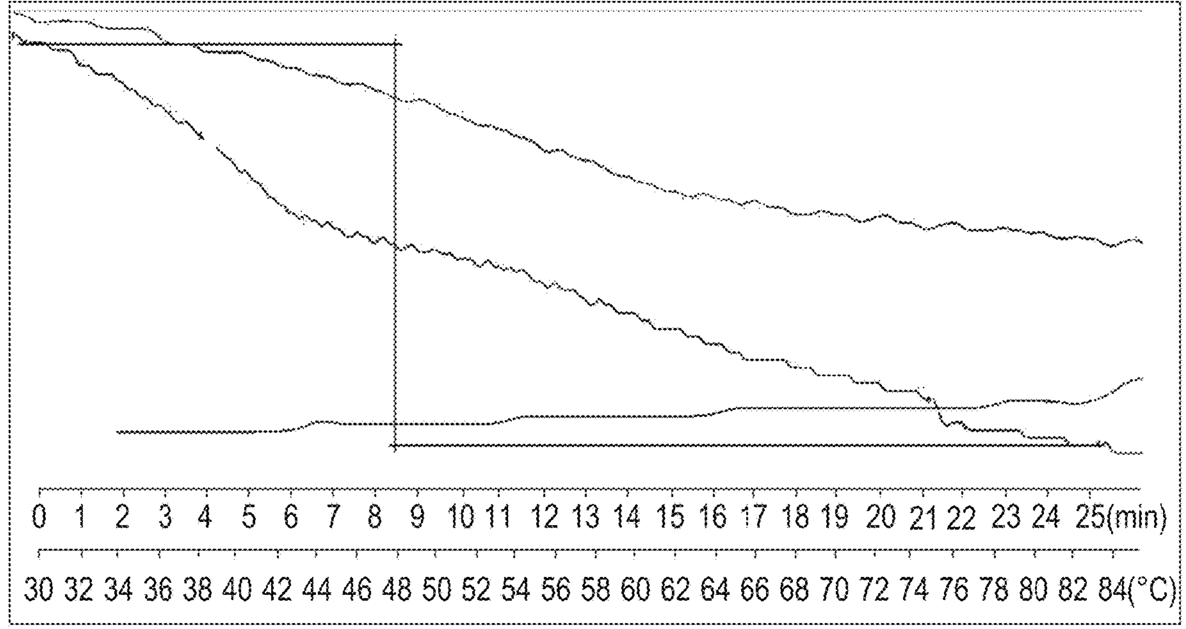
FIG. 22: TGA for sample containing a mixture of crystalline Forms A and B of Compound 1.
Figure 23:
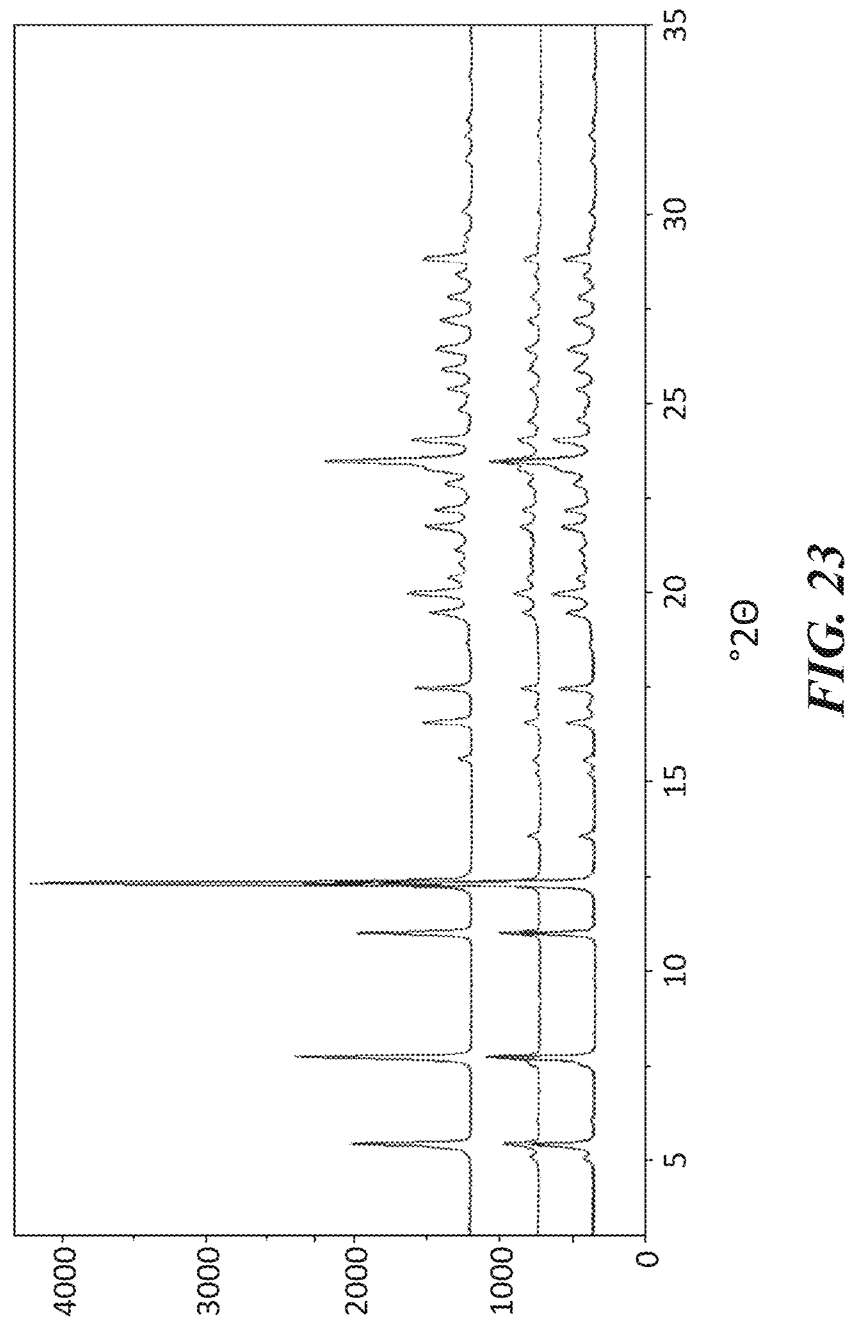
FIG. 23: Diffractogram comparison: Reference (top), sample after TGA (middle), and initial sample (bottom).

Compound 1 (20 mg) containing a mixture of crystalline Forms A and B was heated to 85° C. at 5° C./min, maintained at 85° C. for 10 minutes and cooled to RT. The TGA thermogram is presented in FIG. 22 and shows a total weight loss of 0.25%. The resulting solid was analyzed by XRPD, presented in FIG. 23, showing crystalline Form B was still present after the TGA experiment (reference (top); sample after TGA (middle); and initial sample (bottom)).

IX Sample Stress

Two samples, one containing pure crystalline Form A of Compound 1 and a second containing a mixture of crystalline Forms A and B of Compound 1 were placed in an open vial at 40° C. and 75% relative humidity for 6 days and then analyzed by XRPD. The results are presented in Table 11; no changes by XRPD were observed.

TABLE 11

| XRPD Observations After Stress Conditions | | |
|---|---|---|
| Sample | Initial | XRPD |
| 1 | Form A | No change - all Form A |
| 2 | Form A + form B (minor) | No change - Form A + form B (minor) |

X Lyophilization

Crystalline Form A of Compound 1 (10 mg) dissolved in 1,4-dioxane (1 mL) was frozen at −50° C., and then freeze-dried overnight. The starting material and lyophilized product were analyzed by XRPD and the resulting diffractograms demonstrate that lyophilization converts crystalline Form A to an amorphous form. More specifically, this analyses showed that Form B is an anhydrous/non-solvated solid, that Form A slowly converts to Form B, and that Forms A and B could be enantiotropically related, though they have similar stability.

Example 5

Single Crystal X-Ray Structure of Crystalline Form a of Compound 1

Single crystals of crystalline Form A of Compound 1 were obtained from dichloromethane/pentane.

A 0.15×0.08×0.04 mm colorless crystal was mounted on a Cryoloop with Paratone oil. The single crystal X-ray diffraction studies were carried out on a Bruker Microstar APEX II CCD diffractometer equipped with Cu $K_\alpha$ radiation ($\lambda$=1.54178 Å). Data were collected in a nitrogen gas stream at 100K using $\phi$ and $\overline{\omega}$ scans. Crystal-to-detector distance was 40 mm and exposure time was 5, 10, 15, 25, and 40 seconds depending on the 2θ range per frame using a scan width of 1.00°. Data collection was 99% complete to 66.569° in θ. A total of 13233 reflections were collected covering the indices, −5<=h<=3, −18<=k<=17, −19<=1<=18. 4186 reflections were found to be symmetry independent, with a $R_{int}$ of 0.0405. Indexing and unit cell refinement indicated a Primitive, Monoclinic lattice. The space group was found to be$P2_1$. The data were integrated using the Bruker SAINT Software program and scaled using the SADABS software program. Solution by direct methods (SHELXT) produced a complete phasing model consistent with the proposed structure. All nonhydrogen atoms were refined anisotropically by full-matrix least-squares (SHELXL-2014). All carbon bonded hydrogen atoms were placed using a riding model. Their positions were constrained relative to their parent atom using the appropriate HFIX command in SHELXL-2014. SQUEEZE analysis did not find any solvent accessible voids in the structure.

Figure 24:
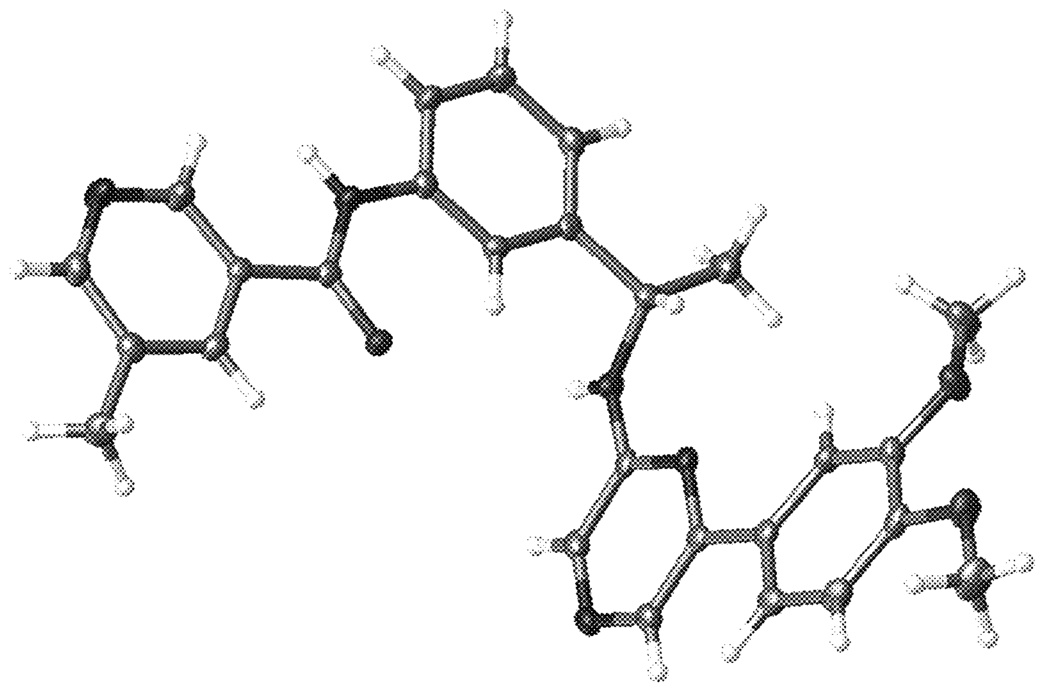
FIG. 24: ORTEP plot representation of the Compound 1, From A crystal structure.

FIG. 24 shows an ORTEP plot representation of the crystal structure of crystalline Form A of Compound 1. In addition, the tables below provided the following structural characteristics of crystalline Form A of Compound 1: Table 12 summarizes the crystallographic data; Table 13 shows the bond lengths [Å]; Table 14 shows the bond angles [° ]; Table 15 shows atomic coordinates ($\times 10^4$) and equivalent isotropic displacement parameters (Å2$\times 10^3$); Table 16 shows hydrogen coordinates ($\times 10^4$) and isotropic displacement parameters (Å2$\times 10^3$); and Table 17 shows the anisotropic displacement parameters (Å2$\times 10^3$).

TABLE 12

| Crystal Data and Structure Refinement | | |
|---|---|---|
| Parameter | Value | |
| Temperature | 100.0 K | |
| Wavelength | 1.54178 Å | |
| Crystal system | Monoclinic | |
| Space group | P 1 21 1 | |
| Unit cell dimensions | a = 4.75520(10) Å | $\alpha$ = 90° |
| | b = 15.9057(4) Å | $\beta$ = 96.954(2)° |
| | c = 15.9986(4) Å | $\gamma$ = 90° |
| Volume | 1201.15(5) $Å^3$ | |
| Z | 2 | |
| Density (calculated) | 1.298 $Mg/m^3$ | |
| Absorption coefficient | 0.703 $mm^{-1}$ | |
| F(000) | 496 | |
| Crystal size | 0.15 × 0.08 × 0.04 $mm^3$ | |
| Theta range for data collection | 2.782 to 66.569°. | |
| Index ranges | −5 <= h <= 3, −18 <= k <= 17, −19 <= l <= 18 | |
| Reflections collected | 13233 | |
| Independent reflections | 4186 [R(int) = 0.0405] | |
| Completeness to theta = 66.569° | 99.0% | |
| Absorption correction | Semi-empirical from equivalents | |
| Max. and min. transmission | 0.7528 and 0.6654 | |
| Refinement method | Full-matrix least-squares on $F^2$ | |
| Data/restraints/parameters | 4186/1/320 | |
| Goodness-of-fit on $F^2$ | 1.025 | |
| Final R indices [I > 2sigma(I)] | R1 = 0.0311, wR2 = 0.0705 | |
| R indices (all data) | R1 = 0.0375, wR2 = 0.0735 | |
| Absolute structure parameter | 0.03(13) | |
| Extinction coefficient | n/a | |
| Largest diff. peak and hole | 0.203 and −0.182 e · $Å^{-3}$ | |

TABLE 13

| Bond lengths [Å] | | | |
|---|---|---|---|
| Bond | Length (Å) | Bond | Length (Å) |
| O(1)—C(7) | 1.232(3) | C(8)—C(27) | 1.395(4) |
| O(2)—C(19) | 1.367(3) | C(9)—H(9) | 0.9500 |
| O(2)—C(20) | 1.431(4) | C(9)—C(10) | 1.374(4) |
| O(3)—C(21) | 1.368(3) | C(10)—H(10) | 0.9500 |
| O(3)—C(22) | 1.423(3) | C(10)—C(11) | 1.395(4) |
| N(1)—C(4) | 1.333(4) | C(11)—H(11) | 0.9500 |
| N(1)—C(5) | 1.337(4) | C(11)—C(12) | 1.378(4) |
| N(2)—H(2) | 0.8800 | C(12)—C(13) | 1.527(3) |
| N(2)—C(7) | 1.361(3) | C(12)—C(27) | 1.400(4) |
| N(2)—C(8) | 1.414(3) | C(13)—H(13) | 1.0000 |
| N(3)—H(3) | 0.8800 | C(13)—C(14) | 1.522(4) |
| N(3)—C(13) | 1.457(3) | C(14)—H(14A) | 0.9800 |
| N(3)—C(15) | 1.363(3) | C(14)—H(14B) | 0.9800 |
| N(4)—C(15) | 1.333(3) | C(14)—H(14C) | 0.9800 |
| N(4)—C(16) | 1.351(3) | C(15)—C(26) | 1.410(4) |
| N(5)—C(25) | 1.342(4) | C(16)—C(17) | 1.472(4) |
| N(5)—C(26) | 1.320(4) | C(16)—C(25) | 1.392(4) |

TABLE 13-continued

| Bond lengths [Å] | | | |
|---|---|---|---|
| Bond | Length (Å) | Bond | Length (Å) |
| C(1)—H(1) | 0.9500 | C(17)—C(18) | 1.403(4) |
| C(1)—C(2) | 1.392(4) | C(17)—C(24) | 1.386(4) |
| C(1)—C(6) | 1.389(4) | C(18)—H(18) | 0.9500 |
| C(2)—C(3) | 1.505(4) | C(18)—C(19) | 1.378(4) |
| C(2)—C(4) | 1.383(4) | C(19)—C(21) | 1.413(4) |
| C(3)—H(3A) | 0.9800 | C(20)—H(20A) | 0.9800 |
| C(3)—H(3B) | 0.9800 | C(20)—H(20B) | 0.9800 |
| C(3)—H(3C) | 0.9800 | C(20)—H(20C) | 0.9800 |
| C(4)—H(4) | 0.9500 | C(21)—C(23) | 1.375(4) |
| C(5)—H(5) | 0.9500 | C(22)—H(22A) | 0.9800 |
| C(5)—C(6) | 1.387(4) | C(22)—H(22B) | 0.9800 |
| C(6)—C(7) | 1.503(4) | C(22)—H(22C) | 0.9800 |
| C(8)—C(9) | 1.397(4) | C(23)—H(23) | 0.9500 |
| C(23)—C(24) | 1.393(4) | C(26)—H(26) | 0.9500 |
| C(24)—H(24) | 0.9500 | C(27)—H(27) | 0.9500 |
| C(25)—H(25) | 0.9500 | | |

TABLE 14

| Bond angles [°] | | | |
|---|---|---|---|
| Bond | Angle [°] | Bond | Angle [°] |
| C(19)—O(2)—C(20) | 117.0(2) | C(8)—C(9)—H(9) | 119.8 |
| C(21)—O(3)—C(22) | 116.2(2) | C(10)—C(9)—C(8) | 120.4(2) |
| C(4)—N(1)—C(5) | 117.1(2) | C(10)—C(9)—H(9) | 119.8 |
| C(7)—N(2)—H(2) | 115.8 | C(9)—C(10)—H(10) | 119.7 |
| C(7)—N(2)—C(8) | 128.4(2) | C(9)—C(10)—C(11) | 120.6(3) |
| C(8)—N(2)—H(2) | 115.8 | C(11)—C(10)—H(10) | 119.7 |
| C(13)—N(3)—H(3) | 119.1 | C(10)—C(11)—H(11) | 120.1 |
| C(15)—N(3)—H(3) | 119.1 | C(12)—C(11)—C(10) | 119.8(2) |
| C(15)—N(3)—C(13) | 121.8(2) | C(12)—C(11)—H(11) | 120.1 |
| C(15)—N(4)—C(16) | 117.9(2) | C(11)—C(12)—C(13) | 122.8(2) |
| C(26)—N(5)—C(25) | 117.6(2) | C(11)—C(12)—C(27) | 119.8(2) |
| C(2)—C(1)—H(1) | 120.0 | C(27)—C(12)—C(13) | 117.4(2) |
| C(6)—C(1)—H(1) | 120.0 | N(3)—C(13)—C(12) | 109.7(2) |

TABLE 14-continued

| Bond angles [°] | | | |
|---|---|---|---|
| Bond | Angle [°] | Bond | Angle [°] |
| C(6)—C(1)—C(2) | 120.1(2) | N(3)—C(13)—H(13) | 106.9 |
| C(1)—C(2)—C(3) | 122.2(2) | N(3)—C(13)—C(14) | 111.3(2) |
| C(4)—C(2)—C(1) | 117.3(2) | C(12)—C(13)—H(13) | 106.9 |
| C(4)—C(2)—C(3) | 120.5(2) | C(14)—C(13)—C(12) | 114.7(2) |
| C(2)—C(3)—H(3A) | 109.5 | C(14)—C(13)—H(13) | 106.9 |
| C(2)—C(3)—H(3B) | 109.5 | C(13)—C(14)—H(14A) | 109.5 |
| C(2)—C(3)—H(3C) | 109.5 | C(13)—C(14)—H(14B) | 109.5 |
| H(3A)—C(3)—H(3B) | 109.5 | C(13)—C(14)—H(14C) | 109.5 |
| H(3A)—C(3)—H(3C) | 109.5 | H(14A)—C(14)—H(14B) | 109.5 |
| H(3B)—C(3)—H(3C) | 109.5 | H(14A)—C(14)—H(14C) | 109.5 |
| N(1)—C(4)—C(2) | 124.2(3) | H(14B)—C(14)—H(14C) | 109.5 |
| N(1)—C(4)—H(4) | 117.9 | N(3)—C(15)—C(26) | 119.9(2) |
| C(2)—C(4)—H(4) | 117.9 | N(4)—C(15)—N(3) | 119.2(2) |
| N(1)—C(5)—H(5) | 117.9 | N(4)—C(15)—C(26) | 120.8(2) |
| N(1)—C(5)—C(6) | 124.1(3) | N(4)—C(16)—C(17) | 117.0(2) |
| C(6)—C(5)—H(5) | 117.9 | N(4)—C(16)—C(25) | 120.3(2) |
| C(1)—C(6)—C(7) | 118.2(2) | C(25)—C(16)—C(17) | 122.6(2) |
| C(5)—C(6)—C(1) | 117.1(2) | C(18)—C(17)—C(16) | 119.1(2) |
| C(5)—C(6)—C(7) | 124.7(2) | C(24)—C(17)—C(16) | 122.5(2) |
| O(1)—C(7)—N(2) | 123.7(2) | C(24)—C(17)—C(18) | 118.4(2) |
| O(1)—C(7)—C(6) | 120.4(2) | C(17)—C(18)—H(18) | 119.4 |
| N(2)—C(7)—C(6) | 115.9(2) | C(19)—C(18)—C(17) | 121.3(2) |
| C(9)—C(8)—N(2) | 116.3(2) | C(19)—C(18)—H(18) | 119.4 |
| C(27)—C(8)—N(2) | 124.7(2) | O(2)—C(19)—C(18) | 125.3(2) |
| C(27)—C(8)—C(9) | 118.9(2) | O(2)—C(19)—C(21) | 115.1(2) |
| C(18)—C(19)—C(21) | 119.6(2) | C(21)—C(23)—H(23) | 119.6 |
| O(2)—C(20)—H(20A) | 109.5 | C(21)—C(23)—C(24) | 120.8(2) |
| O(2)—C(20)—H(20B) | 109.5 | C(24)—C(23)—H(23) | 119.6 |
| O(2)—C(20)—H(20C) | 109.5 | C(17)—C(24)—C(23) | 120.7(2) |
| H(20A)—C(20)—H(20B) | 109.5 | C(17)—C(24)—H(24) | 119.6 |
| H(20A)—C(20)—H(20C) | 109.5 | C(23)—C(24)—H(24) | 119.6 |
| H(20B)—C(20)—H(20C) | 109.5 | N(5)—C(25)—C(16) | 121.8(2) |
| O(3)—C(21)—C(19) | 114.9(2) | N(5)—C(25)—H(25) | 119.1 |
| O(3)—C(21)—C(23) | 125.8(2) | C(16)—C(25)—H(25) | 119.1 |
| C(23)—C(21)—C(19) | 119.2(2) | N(5)—C(26)—C(15) | 121.5(2) |
| O(3)—C(22)—H(22A) | 109.5 | N(5)—C(26)—H(26) | 119.3 |
| O(3)—C(22)—H(22B) | 109.5 | C(15)—C(26)—H(26) | 119.3 |
| O(3)—C(22)—H(22C) | 109.5 | C(8)—C(27)—C(12) | 120.5(2) |
| H(22A)—C(22)—H(22B) | 109.5 | C(8)—C(27)—H(27) | 119.8 |
| H(22A)—C(22)—H(22C) | 109.5 | C(12)—C(27)—H(27) | 119.8 |
| H(22B)—C(22)—H(22C) | 109.5 | | |

TABLE 15

Atomic coordinates (×$10^4$) and Equivalent Isotropic Displacement Parameters (Å$^2$ × $10^3$) (U(eq) is defined as one third of the trace of the orthogonalized $U^{ij}$ tensor)

| | x | y | z | U(eq) |
|---|---|---|---|---|
| O(1) | 1659(4) | 4719(1) | 4874(1) | 20(1) |
| O(2) | 3310(4) | 4941(1) | 10223(1) | 29(1) |
| O(3) | 222(4) | 3710(1) | 10613(1) | 28(1) |
| N(1) | −3935(6) | 5656(2) | 2360(2) | 33(1) |
| N(2) | 2556(5) | 6027(1) | 4375(1) | 18(1) |
| N(3) | 10236(5) | 4790(1) | 6678(1) | 19(1) |
| N(4) | 7612(4) | 4101(1) | 7605(1) | 17(1) |
| N(5) | 8617(5) | 2582(1) | 6832(1) | 22(1) |
| C(1) | −2580(6) | 4405(2) | 3550(2) | 19(1) |
| C(2) | −4643(6) | 4262(2) | 2871(2) | 20(1) |
| C(3) | −6231(6) | 3443(2) | 2756(2) | 28(1) |
| C(4) | −5217(6) | 4909(2) | 2298(2) | 25(1) |
| C(5) | −1930(7) | 5770(2) | 3012(2) | 29(1) |
| C(6) | −1140(6) | 5166(2) | 3622(2) | 17(1) |
| C(7) | 1135(5) | 5283(2) | 4351(2) | 17(1) |
| C(8) | 4822(6) | 6299(2) | 4967(2) | 18(1) |
| C(9) | 5869(6) | 7105(2) | 4846(2) | 22(1) |
| C(10) | 8068(6) | 7423(2) | 5392(2) | 25(1) |
| C(11) | 9299(6) | 6945(2) | 6071(2) | 21(1) |
| C(12) | 8282(6) | 6151(2) | 6203(2) | 17(1) |
| C(13) | 9399(6) | 5613(2) | 6962(2) | 19(1) |
| C(14) | 11764(6) | 6017(2) | 7554(2) | 26(1) |
| C(15) | 9167(5) | 4066(2) | 6967(1) | 18(1) |

TABLE 15-continued

Atomic coordinates (×$10^4$) and Equivalent Isotropic Displacement Parameters (Å$^2$ × $10^3$) (U(eq) is defined as one third of the trace of the orthogonalized $U^{ij}$ tensor)

| | x | y | z | U(eq) |
|---|---|---|---|---|
| C(16) | 6518(5) | 3376(2) | 7863(2) | 18(1) |
| C(17) | 4809(6) | 3429(2) | 8570(2) | 18(1) |
| C(18) | 4893(6) | 4169(2) | 9049(2) | 19(1) |
| C(19) | 3337(6) | 4249(2) | 9718(2) | 22(1) |
| C(20) | 5355(7) | 5582(2) | 10124(2) | 34(1) |
| C(21) | 1624(6) | 3574(2) | 9928(2) | 23(1) |
| C(22) | −1455(7) | 3032(2) | 10856(2) | 34(1) |
| C(23) | 1546(6) | 2847(2) | 9461(2) | 23(1) |
| C(24) | 3115(6) | 2773(2) | 8783(2) | 22(1) |
| C(25) | 7032(6) | 2620(2) | 7471(2) | 21(1) |
| C(26) | 9690(6) | 3292(2) | 6585(2) | 22(1) |
| C(27) | 6057(5) | 5822(2) | 5646(2) | 17(1) |

TABLE 16

Hydrogen Coordinates (×$10^4$) and Isotropic Displacement Parameters (Å$^2$ × $10^3$)

| | x | y | z | U(eq) |
|---|---|---|---|---|
| H(2) | 1991 | 6384 | 3969 | 22 |
| H(3) | 11465 | 4760 | 6309 | 23 |

TABLE 16-continued

| Hydrogen Coordinates (×$10^4$) and Isotropic Displacement Parameters ($Å^2$ × $10^3$) | | | | |
|---|---|---|---|---|
| | x | y | z | U(eq) |
| H(1) | −2157 | 3982 | 3965 | 23 |
| H(3A) | −5004 | 2983 | 2987 | 41 |
| H(3B) | −6805 | 3345 | 2155 | 41 |
| H(3C) | −7917 | 3468 | 3052 | 41 |
| H(4) | −6612 | 4815 | 1830 | 30 |
| H(5) | −988 | 6297 | 3060 | 34 |
| H(9) | 5057 | 7435 | 4384 | 27 |
| H(10) | 8756 | 7973 | 5305 | 30 |
| H(11) | 10833 | 7167 | 6441 | 26 |
| H(13) | 7777 | 5520 | 7295 | 22 |
| H(14A) | 12423 | 5621 | 8005 | 39 |
| H(14B) | 11052 | 6528 | 7798 | 39 |
| H(14C) | 13341 | 6162 | 7239 | 39 |
| H(18) | 6046 | 4624 | 8911 | 23 |
| H(20A) | 4949 | 5836 | 9564 | 51 |
| H(20B) | 7256 | 5335 | 10184 | 51 |
| H(20C) | 5262 | 6015 | 10555 | 51 |
| H(22A) | −2900 | 2887 | 10388 | 50 |
| H(22B) | −2378 | 3198 | 11346 | 50 |
| H(22C) | −240 | 2542 | 11001 | 50 |
| H(23) | 408 | 2389 | 9602 | 28 |
| H(24) | 3022 | 2268 | 8464 | 26 |
| H(25) | 6238 | 2116 | 7660 | 26 |
| H(26) | 10841 | 3281 | 6139 | 26 |
| H(27) | 5383 | 5270 | 5731 | 21 |

TABLE 17

| Anisotropic Displacement Parameters ($Å^2$ × $10^3$ (anisotropic displacement factor exponent taking the form: $-2\pi^2[h^2 a^{*2}U^{11} + \ldots + 2 h k a^* b^* U^{12}]$) | | | | | | |
|---|---|---|---|---|---|---|
| | $U^{11}$ | $U^{22}$ | $U^{33}$ | $U^{23}$ | $U^{13}$ | $U^{12}$ |
| O(1) | 27(1) | 16(1) | 17(1) | 3(1) | 0(1) | 0(1) |
| O(2) | 39(1) | 28(1) | 22(1) | −6(1) | 10(1) | −7(1) |
| O(3) | 29(1) | 37(1) | 20(1) | 1(1) | 6(1) | −6(1) |
| N(1) | 46(2) | 24(1) | 24(1) | 6(1) | −11(1) | −6(1) |
| N(2) | 20(1) | 18(1) | 17(1) | 4(1) | 0(1) | −1(1) |
| N(3) | 24(1) | 18(1) | 17(1) | 1(1) | 5(1) | 4(1) |
| N(4) | 20(1) | 19(1) | 13(1) | 0(1) | −1(1) | 2(1) |
| N(5) | 29(1) | 19(1) | 18(1) | −4(1) | −3(1) | 3(1) |
| C(1) | 20(1) | 20(1) | 18(1) | 4(1) | 3(1) | 2(1) |
| C(2) | 21(1) | 22(1) | 20(1) | −3(1) | 4(1) | 0(1) |
| C(3) | 25(2) | 27(2) | 30(2) | 2(1) | −1(1) | −5(1) |
| C(4) | 30(2) | 27(2) | 17(1) | −2(1) | −3(1) | −2(1) |
| C(5) | 42(2) | 20(2) | 22(2) | 3(1) | −6(1) | −7(1) |
| C(6) | 20(1) | 17(1) | 15(1) | 0(1) | 3(1) | 3(1) |
| C(7) | 20(1) | 17(1) | 15(1) | 0(1) | 5(1) | 1(1) |
| C(8) | 21(1) | 19(1) | 14(1) | −2(1) | 4(1) | 1(1) |
| C(9) | 30(2) | 20(1) | 16(1) | 5(1) | 0(1) | 1(1) |
| C(10) | 34(2) | 18(1) | 21(1) | 2(1) | 1(1) | −8(1) |
| C(11) | 24(1) | 22(1) | 17(1) | −2(1) | 0(1) | −4(1) |
| C(12) | 22(1) | 18(1) | 13(1) | −1(1) | 7(1) | 4(1) |
| C(13) | 23(1) | 16(1) | 17(1) | 0(1) | 3(1) | 3(1) |
| C(14) | 34(2) | 24(1) | 19(1) | −1(1) | −3(1) | 4(1) |
| C(15) | 19(1) | 23(1) | 10(1) | 1(1) | −3(1) | 4(1) |
| C(16) | 21(1) | 18(1) | 14(1) | 0(1) | −6(1) | 2(1) |
| C(17) | 19(1) | 20(1) | 14(1) | 2(1) | −4(1) | 2(1) |
| C(18) | 24(1) | 18(1) | 16(1) | 3(1) | 2(1) | −1(1) |
| C(19) | 26(2) | 23(1) | 16(1) | −1(1) | 0(1) | −1(1) |
| C(20) | 52(2) | 26(2) | 26(2) | −6(1) | 10(1) | −11(1) |
| C(21) | 21(1) | 32(2) | 15(1) | 6(1) | −1(1) | 0(1) |
| C(22) | 30(2) | 43(2) | 29(2) | 8(1) | 5(1) | −9(1) |
| C(23) | 20(1) | 26(2) | 22(2) | 4(1) | −2(1) | −6(1) |
| C(24) | 22(2) | 19(1) | 21(1) | 0(1) | −5(1) | −1(1) |
| C(25) | 25(2) | 20(1) | 18(1) | −1(1) | −3(1) | 0(1) |
| C(26) | 25(1) | 23(2) | 16(1) | −2(1) | −1(1) | 6(1) |
| C(27) | 20(1) | 15(1) | 16(1) | 2(1) | 4(1) | 1(1) |

Example 6

Analysis of Crystalline Form a of Compound 1

I X-ray Powder Diffraction (XRPD)

Figure 25:
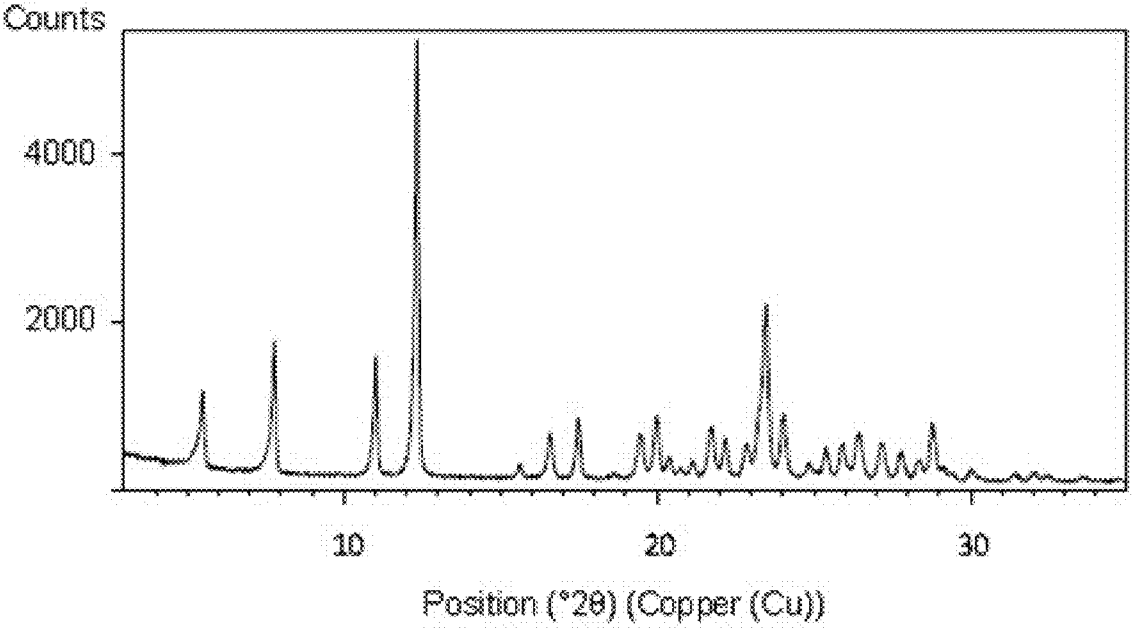
FIG. 25: XRPD 2θ Diffractogram of Compound 1 Crystalline Polymorph Form A.

XRPD analysis was carried out on a PANalytical X'pert pro with PIXcel detector (128 channels), scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation (α1)=1.54060 Å; α2=1.54443 Å; β=1.39225 Å; α1:α2 ratio=0.5) running in transmission mode (step size 0.0130° 2θ, step time 18.87 s) using 40 kV/40 mA generator settings. Data were visualized and images generated using the HighScore Plus 4.7 desktop application (PANalytical, 2017). The XRPD 2Θ diffractogram of crystalline Form A of Compound 1 is shown in FIG. 25 revealing the material to be highly crystalline.

II Polarized Light Microscopy

Figure 26:
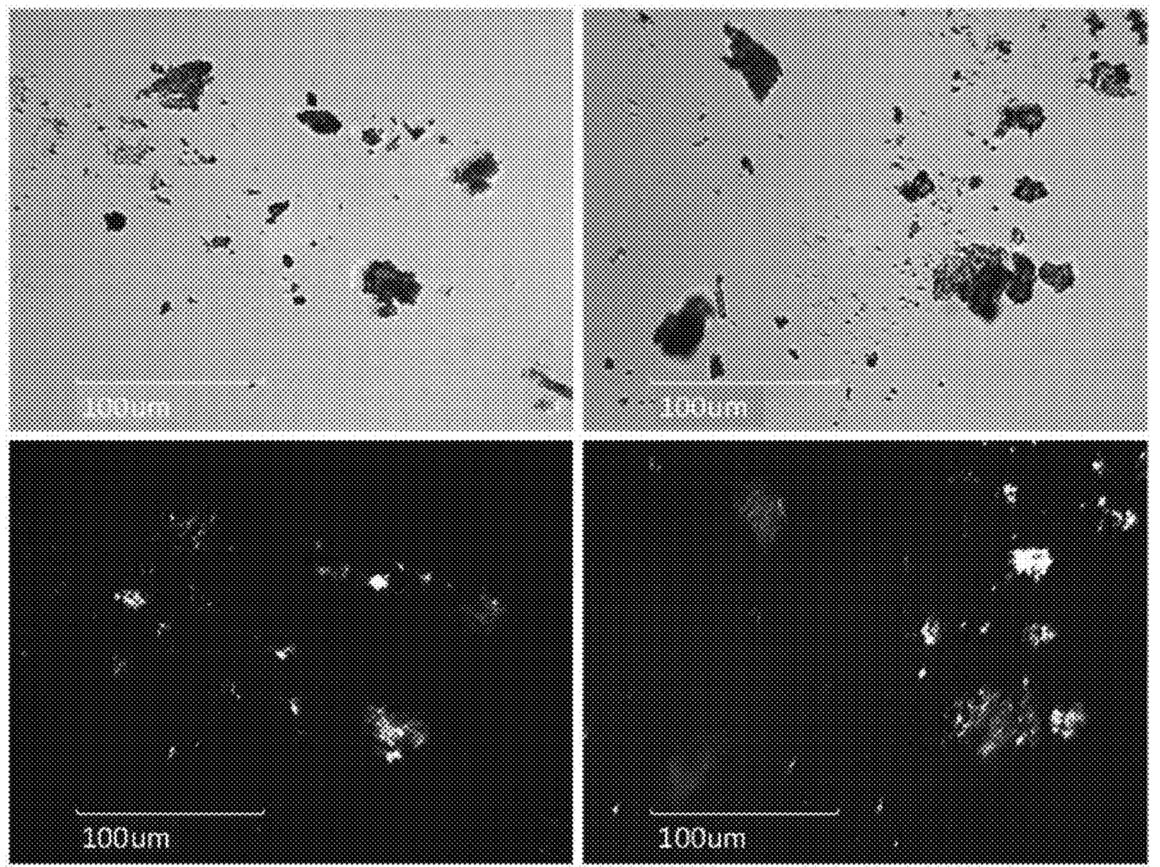
FIG. 26: Visible light non-polarized (top) and polarized (bottom) microscopic images of Compound 1.

The presence of crystallinity (birefringence) was determined using an Olympus BX50 polarizing microscope, equipped with a Motic camera and image capture software (Motic Images Plus 2.0). All images were recorded using at 200× magnification using a 20× objective, unless otherwise stated. Visible light non-polarized (top) and polarized (bottom) microscopic images of crystalline Form A of Compound 1 are shown in FIG. 26, showing aggregated particles with no clear morphology.

III Liquid Chromatography-Mass Spectrometry (LC-MS)

The LC-MS of crystalline Form A of Compound 1 was determined using the following parameters:

| | | |
|---|---|---|
| Column | ACE EXCEL3 super C18, 3.0 μm, 75 × 4.6 mm | |
| Mobile Phase A: | 0.1% Formic acid in H2O | |
| Mobile Phase B: | 0.1% Formic acid in MeCN | |
| Diluent: | 50:50 MeCN/H2O (% % v/v) | |
| Flow Rate | 15 mL/min | |
| Runtime: | 20 min | |
| Column Temperature: | 30° C. | |
| Injection Volume: | 10 μL | |
| PDA Range: | 190-400 nm | |
| | Time (minutes) | Solvent B [%] |
| Gradient Program: | 0 | 5 |
| | 12 | 5 |
| | 15 | 95 |
| | 15.1 | 95 |
| | 20 | 5 |

Figure 27:
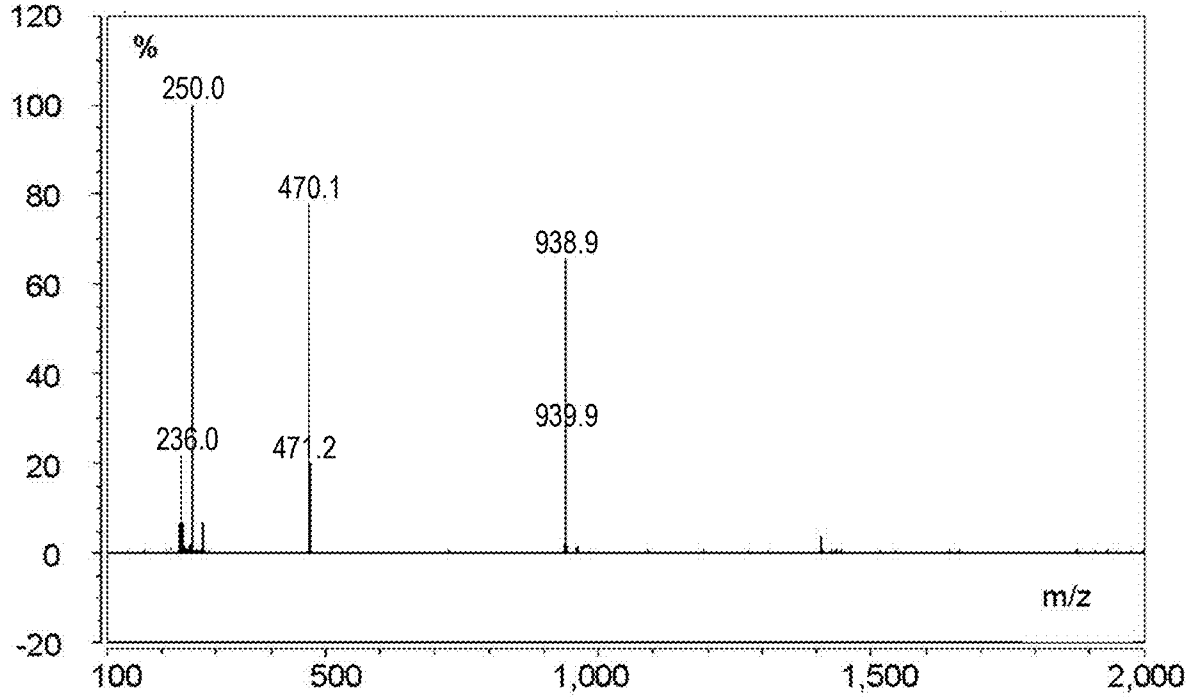
FIG. 27: LC-MS Spectrum of Compound 1.

The LC-MS spectrum of crystalline Form A of Compound 1 is shown in FIG. 27, with observed peaks at:

| | |
|---|---|
| m/z 470.1 | $[M + H]^+$ consistent with chemical structure; |
| m/z 236.0 | $[M + 2H]^{2+}$; |
| m/z 256.0 | $[M + H + Na]^{2+}$; and |
| m/z 938.9 | $[2M + H]^+$. |

IV High Performance Liquid Chromatography (HPLC)

Crystalline Form A of Compound 1 was run through PLC as follows:

| | |
|---|---|
| Column: | Accucore RP-MS 150 mm × 4.6 mm, 2.6 μm |
| Column Temperature: | 20° C. |

-continued

| | |
|---|---|
| Autosampler Temperature: | Ambient |
| UV wavelength: | 270 nm |
| Injection Volume: | 15 µL |
| Flow Rate: | 15 mL/min |
| Mobile Phase A: | 0.1% TFA in H2O:MeCN (75:25% % v/v) |
| Mobile Phase B: | 0.1% TFA in MeCN |

| | Time (minutes) | Solvent B [%] |
|---|---|---|
| Gradient program: | 0 | 0 |
| | 5 | 0 |
| | 35 | 53.3 |
| | 40 | 53.3 |
| | 45 | 0 |

Figure 28:
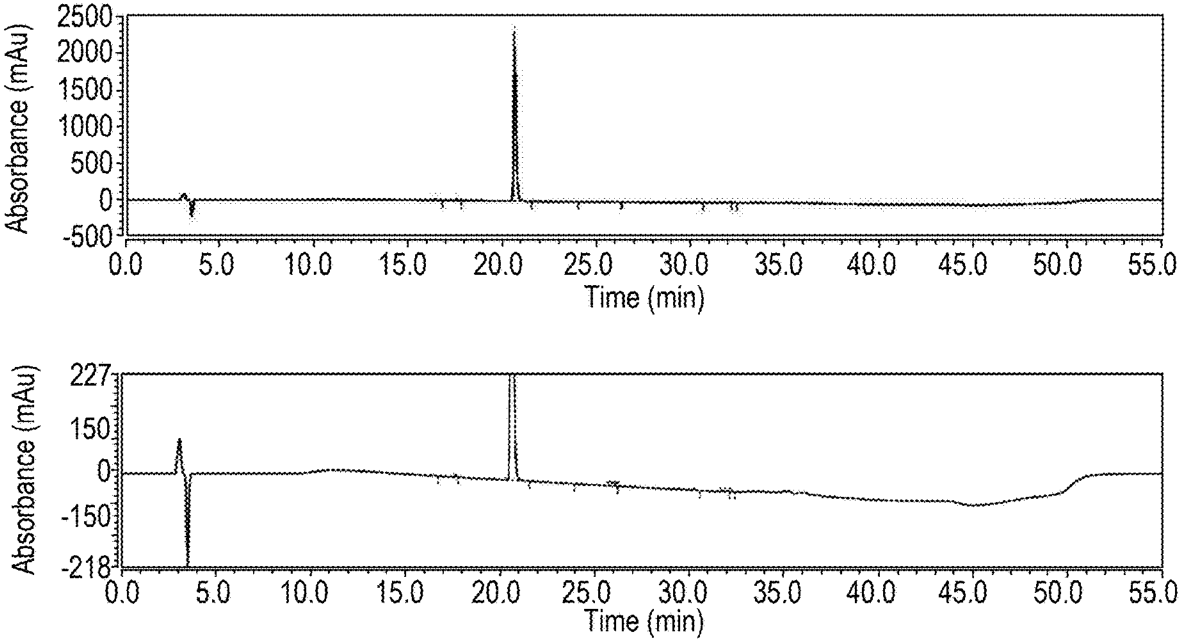
FIG. 28: HPLC Chromatogram of Compound 1.

The HPLC chromatogram of crystalline Form A of Compound 1 is shown in FIG. 28 confirming the sample was 99.3% pure. The integration results are presented in Table 18.

TABLE 18

HPLC Peak Integration

| No. | Peak Name | Ret. Time (min) | Rel RT Cmpd 1 | Area mAU*min | Height mAU | Relative Area % |
|---|---|---|---|---|---|---|
| 1 | | 16.453 | 0.80 | 0.278 | 2.279 | 0.09 |
| 2 | | 17.683 | 0.86 | 0.214 | 2.198 | 0.07 |
| 3 | Cmpd 1 | 20.607 | 1.00 | 317.107 | 2280.383 | 99.40 |
| 4 | | 23.457 | 1.14 | 0.267 | 1.691 | 0.08 |
| 5 | | 25.910 | 1.26 | 0.233 | 1.590 | 0.07 |
| 6 | | 26.137 | 1.27 | 0.005 | 0.063 | 0.00 |
| 7 | | 30.270 | 1.47 | 0.335 | 2.507 | 0.10 |
| 8 | | 31.917 | 1.55 | 0.343 | 2.264 | 0.11 |
| 9 | | 32.207 | 1.56 | 0.234 | 1.383 | 0.07 |
| | TOTAL | | | 319.017 | 2294.358 | 100.0 |

100.00

V Thermogravimetric/Differential Thermal Analyzer (TG/DTA)

Figure 29:
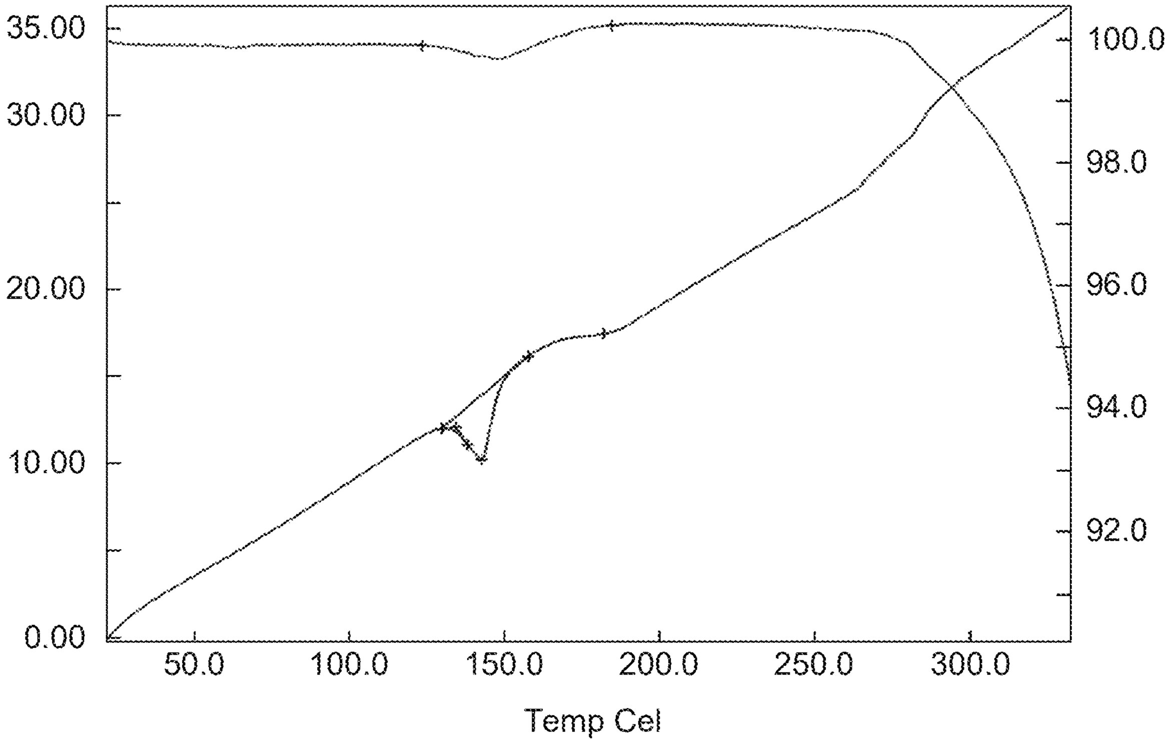
FIG. 29: TG/DTA thermogram of Compound 1, TG upper trace|DT lower trace.

Approximately, 5 mg of crystalline Form A of Compound 1 was weighed into an open aluminum pan and loaded into a simultaneous thermogravimetric/differential thermal analyzer (TG/DTA), and held at room temperature. The sample was then heated at a rate of 10° C./min from 20° C. to 350° C. during which time the change in sample weight was recorded along with any differential thermal events (DTA). Nitrogen was used as the purge gas, at a flow rate of 300 $cm^3$/min. The TG/DTA thermogram of crystalline Form A of Compound 1 is shown in FIG. 29. The thermal gravimetric (upper trace) showed no significant loss in mass prior to degradation. The differential thermogram (lower trace) showed an endothermic event (onset ~134° C.) due to melting. Thus, the melt onset of compound 1 was ca. 134° C. A small mass increase (~0.3%) was observed around the melting temperature VI Differential Scanning Calorimetry (DSC)

Figure 30:
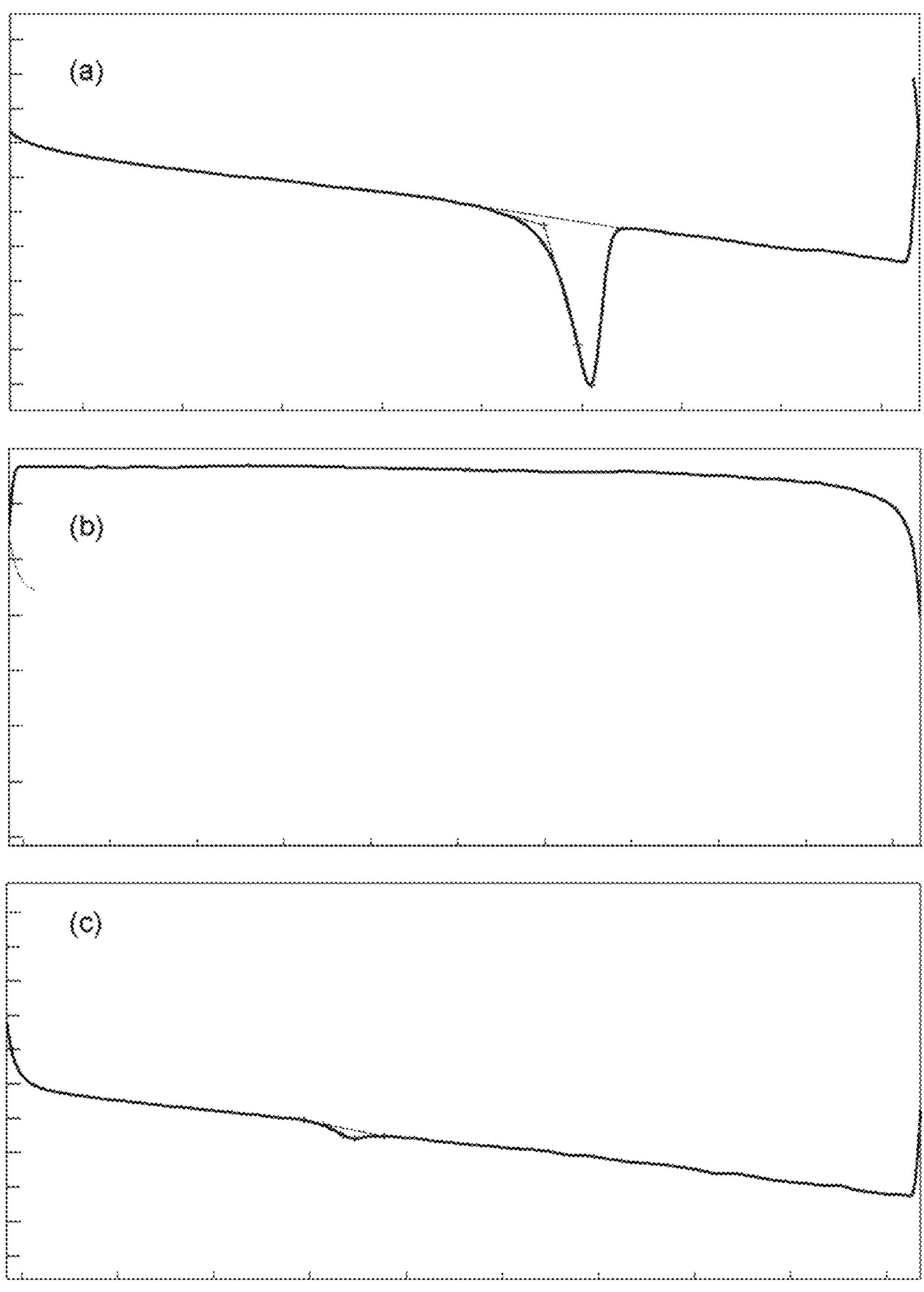
FIG. 30: DSC thermograms of Compound 1: (a) 1$^{st}$ heating step; (b) cooling step and (c) 2$^{nd}$ heat (20 to 200° C.).

Approximately, 5 mg of crystalline Form A of Compound 1 was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to melting at a scan rate of 10° C./min and the resulting heat flow response monitored. Nitrogen was used as the purge gas, at a flow rate of 50 $cm^3$/min. DSC thermograms are show in FIG. 30: (a) $1^{st}$ heating step; (b) cooling step and (c) $2^{nd}$ heat (20 to 200° C.). The sample was heated to melting)(~200° C. before being cooled to 20° C. and then re-heated to melting again. A sharp endothermic event due to melting was observed during the first heating step with onset at approximately 133° C., consistent with the melt onset observed by TG/DTA. No thermal events were observed upon cooling, indicating the material remained amorphous on cooling. A weak thermal event at ~83° C., possibly due to a glass transition, was observed in the second heating step VII Gravimetric Vapor Sorption (GVS)

Figure 31:
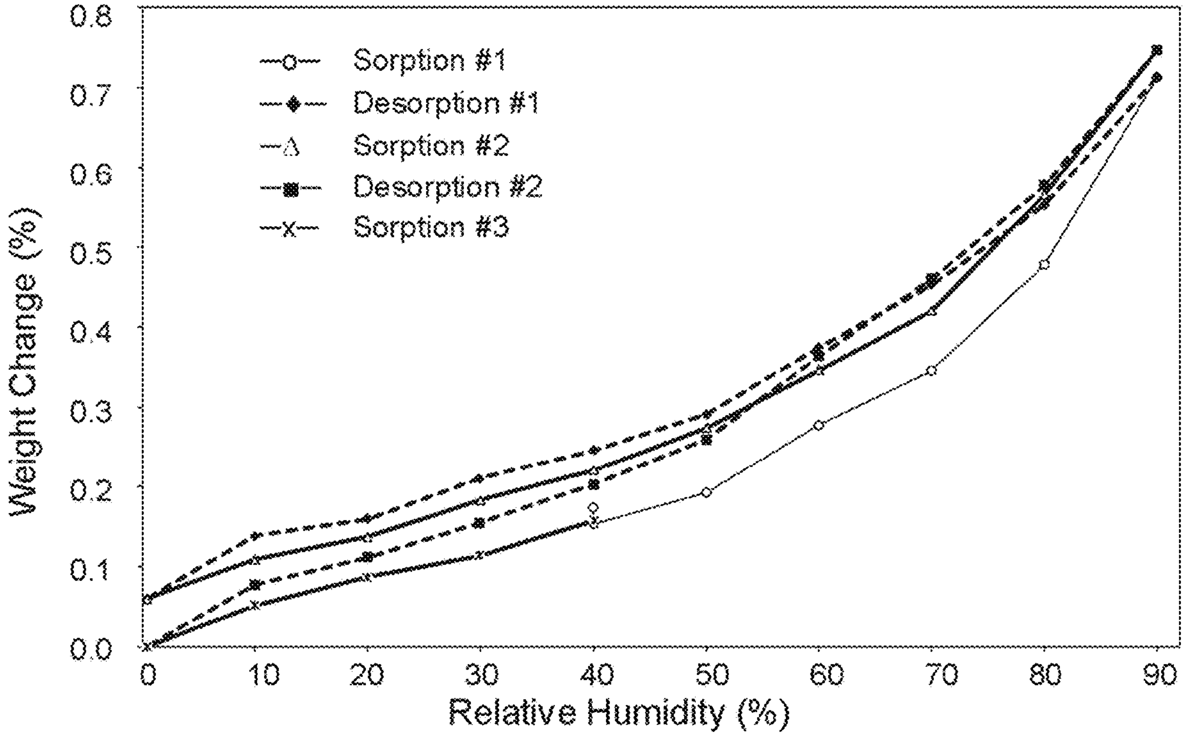
FIG. 31: GVS isotherm (double cycle) for Compound 1.
Figure 32:
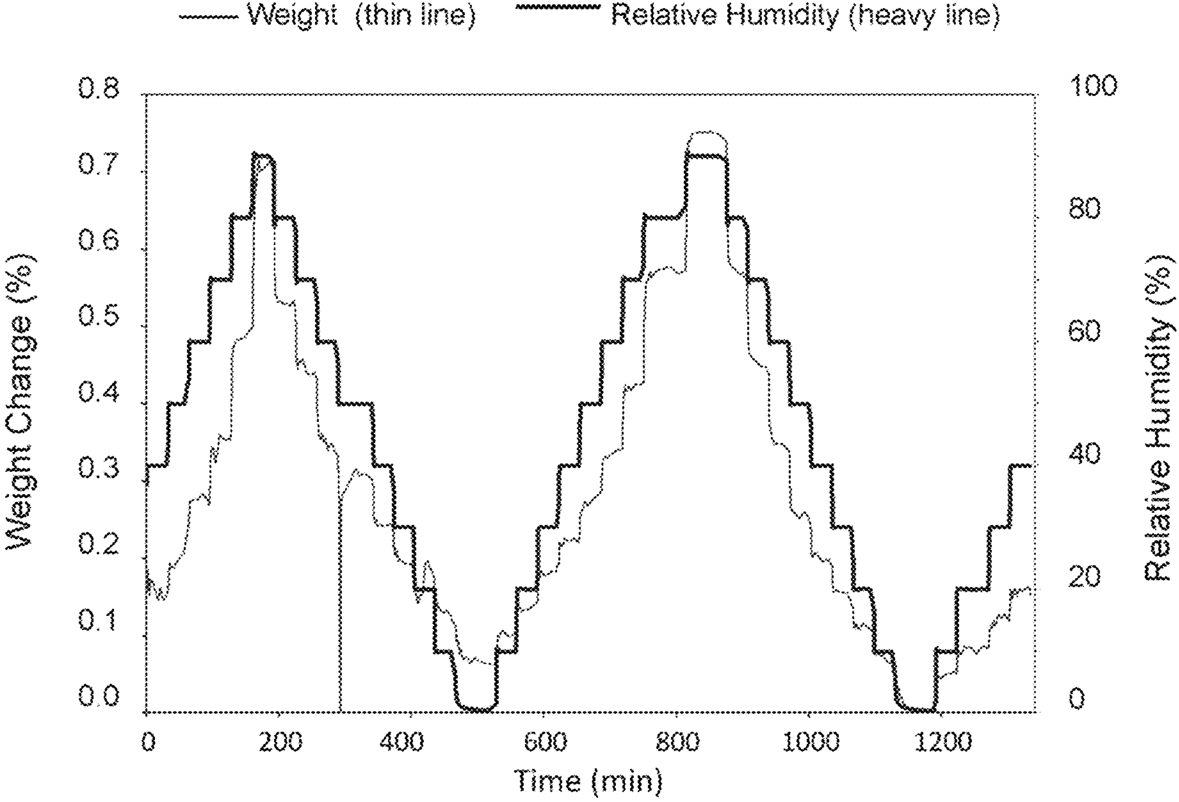
FIG. 32: GVS kinetic plot for Compound 1.

Approximately 10-20 mg of crystalline Form A of Compound 1 was placed into a mesh vapor sorption balance pan and loaded into an IGASorp Moisture Sorption Analyzer balance by Hiden Analytical. The sample was subjected to a ramping profile from 40-90% relative humidity (RH) at 10% increments, maintaining the sample at each step until a stable weight had been achieved (98% step completion, minimum step length 30 minutes, maximum step length 60 minutes) at 25° C. After completion of the sorption cycle, the sample was dried using the same procedure to 0% RH, and finally taken back to the starting point of 40% RH. Two cycles were performed. The weight change during the sorption/desorption cycles were plotted, allowing for the hygroscopic nature of the sample to be determined. FIG. 31 shows the GVS isotherm (double cycle) and FIG. 32 shows GVS kinetics. An approximate 0.7% mass increase up to 90% relative humidity suggests the material was slightly hygroscopic. The material displayed a Langmuir Type I isotherm. No evidence of re-crystallization or form change occurred. (Note, the artefact at around 300 min during the first desorption step is believed due to an experiment error.)

VIII Lyophilization

Figure 33:
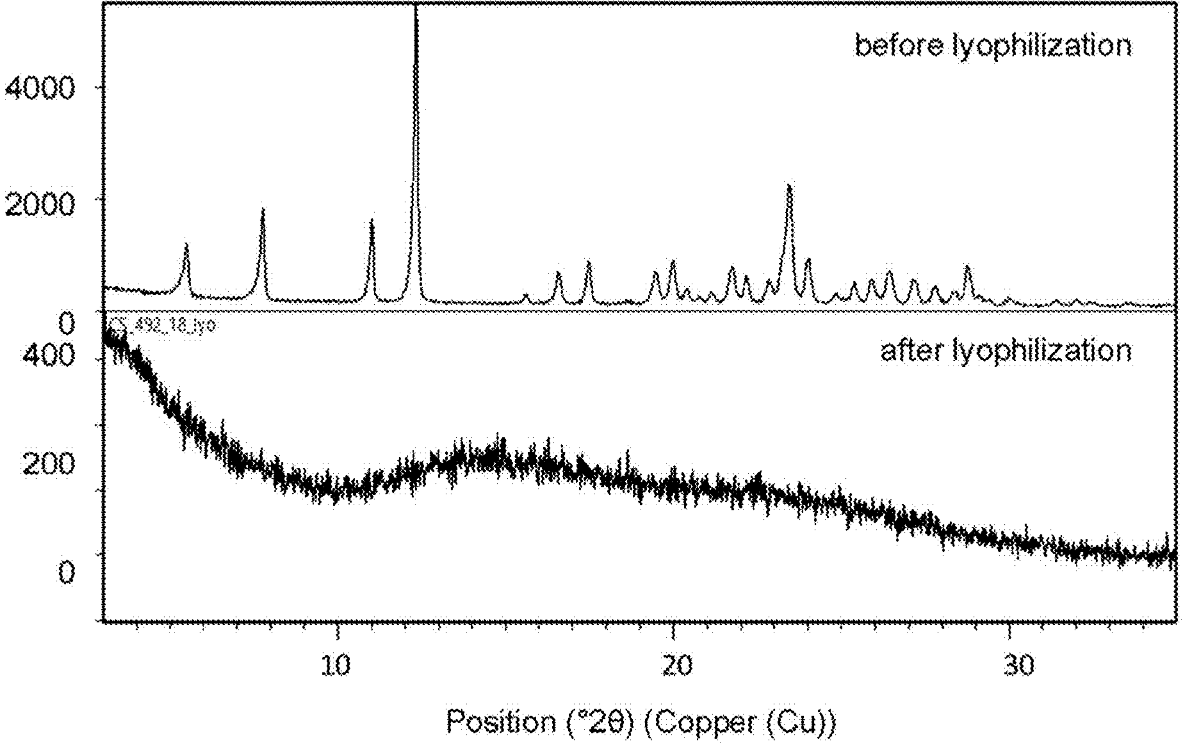
FIG. 33: XRPD 2θ Diffractogram of Compound 1, before (top) and after lyophilization (bottom).

Crystalline Form A of Compound 1 (180 mg) was dissolved in 1,4-dioxane (18 mL). 1 mL (10 mg) of the solution was transferred to a vial which was then frozen at −50° C., before being freeze dried overnight. The starting material and lyophilized product were analyzed by XRPD. The resulting XRPD 2Θ diffractograms are shown in FIG. 33 and demonstrate that lyophilization converts crystalline Form A of Compound 1 to an amorphous form.

IX Physical Stability

Crystalline Form A of Compound 1 (10 mg) was weighed into vials. Two vials each were then stored for 1 week under various conditions of temperature and relative humidity. HPLC analysis was performed to assess changes in purity and the results are presented in Table 19 showing no notable reduction in purity was observed under any of the conditions tested.

TABLE 19

HPLC Analyses

| Storage Conditions (1 week) | Purity (%) |
|---|---|
| Before storage | ~99.3 |
| 25° C./60% relative humidity (open vial) | ~99.1 |
| 40° C./75% relative humidity (open vial) | ~99.1 |
| 80° C. (closed vial) | ~99.0 |
| Ambient light/temperature (closed vial) | ~98.9 |

Figure 34:
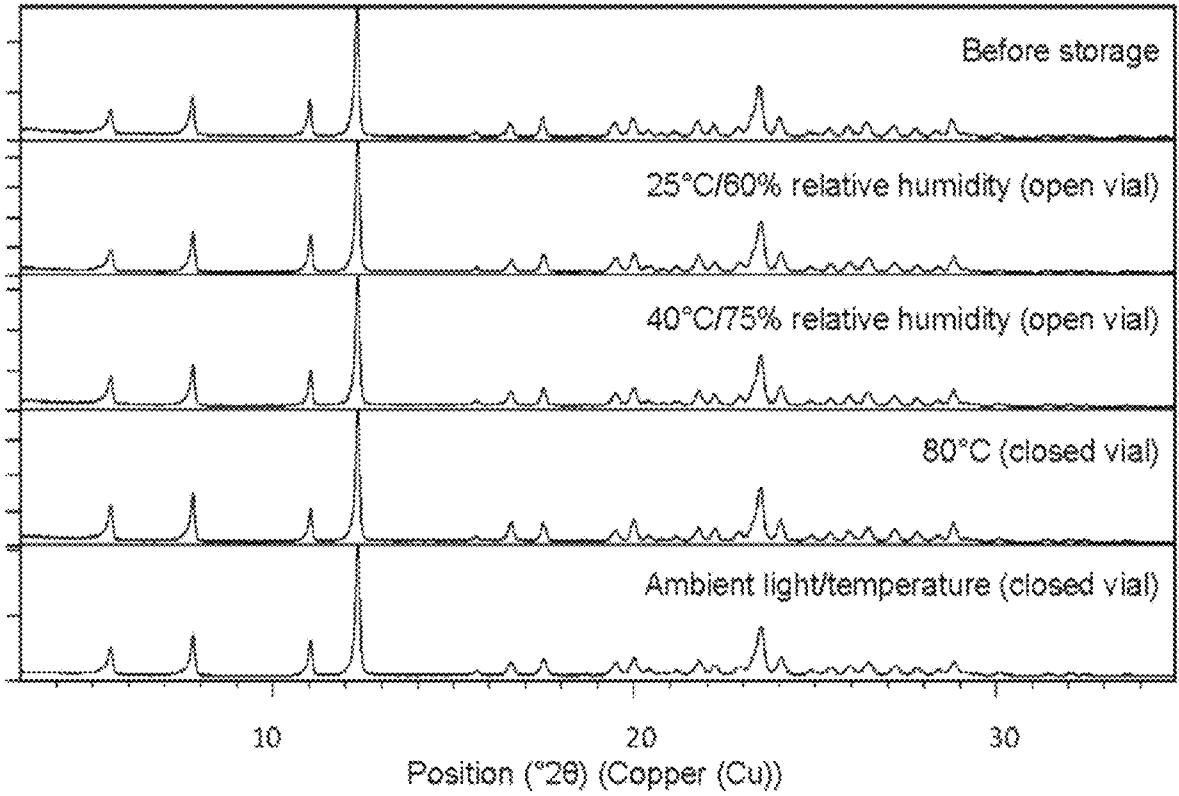
FIG. 34: XRPD diffractograms of Compound 1 after storage for one week under varying conditions of temperature (ambient, 25° C., 40° C., 80° C.) and relative humidity (ambient, 60%, 75%).

XRPD analysis was performed to detect changes in crystallinity. The XRPD diffractograms are shown in FIG. 34 and demonstrate crystalline Form A of Compound 1 was maintained (i.e. no conversation to amorphous form) under the conditions tested; namely, storage for one week under varying conditions of temperature (ambient, 25° C., 40° C., 80° C.) and relative humidity (ambient, 60%, 75%).

X Thermodynamic Solubility

Crystalline Form A of Compound 1 (10 mg) was weighed into vials and 1 mL of the following was added:

pH 3 buffer (0.2M sodium citrate and 0.2M citric acid);

pH 4.5 buffer (0.2M sodium acetate and 0.2M acetic acid);

pH 6.8 buffer (0.2M $KH_2PO_4$ and 0.2M NaOH); and deionized water.

The pH was measured after-buffer addition. The material was maintained at ambient temperature with agitation for ~24 h and the pH re-measured. pH values were as shown in Table 20 and show no significant changes were observed.

TABLE 20

| Crystalline Form A of Compound 1 Solubility in Buffer | | |
|---|---|---|
| Buffer | pH (Initial) | pH (24 h) |
| pH 3 | 2.96 | 2.94 |
| pH 4.5 | 4.55 | 4.55 |
| pH 6.8 | 6.83 | 6.79 |
| Water | 6.78 | 6.73 |

Figure 35:
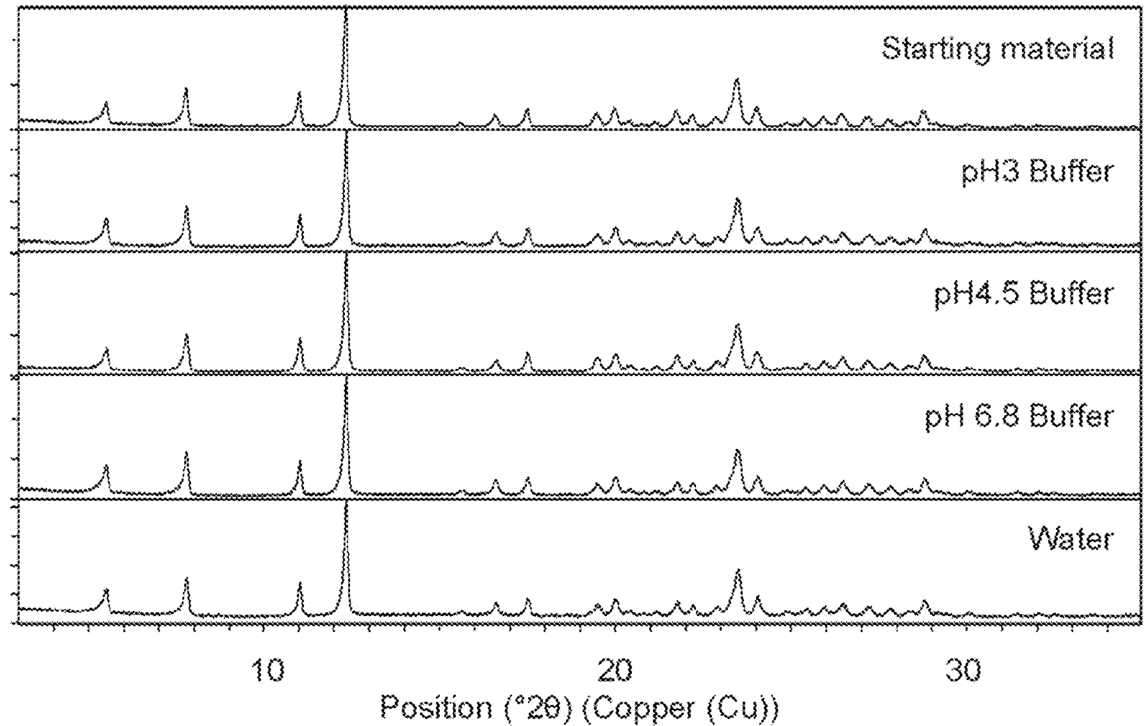
FIG. 35: XRPD diffractograms of Compound 1 before and after slurrying in various buffers.

The remaining solids were isolated by filtration and analyzed by XRPD. The XRPD diffractograms are shown in FIG. 35 and show Form A was isolated from all buffer systems and water. The filtered mother liquors were analyzed by HPLC which showed Compound 1 concentration was low in all buffers and water (<0.05 mg/mL).

Example 7

Single Crystal X-Ray Structure of Compound 1, Form B

Single crystal diffraction data collection was carried out using a Rigaku diffractometer with a MicroMax-007HF Microfocus rotating anode X-ray generator using Mo Kα radiation, equipped with a Pilatus 200K hybrid pixel array detector and an Oxford Cryosystems low temperature device Cryostream 700 plus (T=−173° C.). Full-sphere data collection was completed using $\overline{@}$ scans. Programs used: Data collection and reduction, CrysAlisPro 1.171.39.12b and absorption correction, Scale3 Abspack scaling algorithm. Crystal structure solution was achieved using thecomputer program SHELXT, and visualization was performed with the program SHELXle. Missing atoms were subsequently located from difference Fourier synthesis and added to the atom list. Least-squares refinement on $F^2$ using all measured intensities was carried outusing SHELXL 2018/3. All non-hydrogen atoms were refined including anisotropic displacement parameters.

Figure 36:
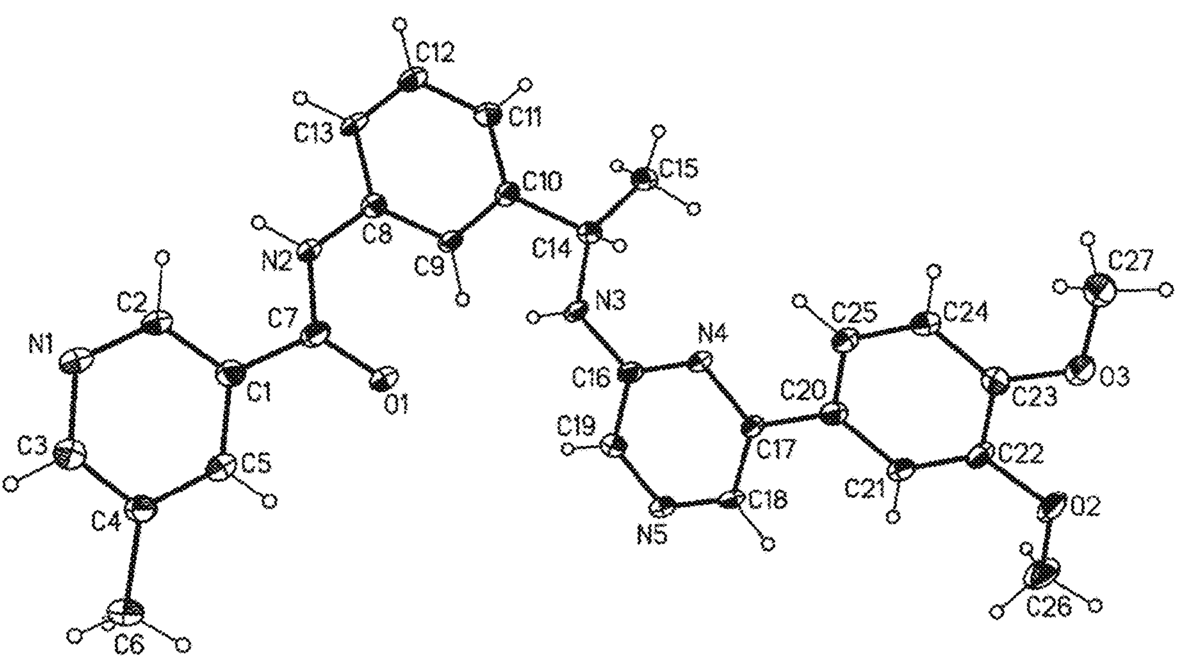
FIG. 36: ORTEP-plot representation (50%) of the structure of compound 1, Form B.

The obtained ORTEP plot (50%) with atom numbering is shown in FIG. 36. The absolute structure shown in the figure was selected randomly and has an R1 value of 6.7%. Form B of Compound 1 crystallizes in the chiral space group P $2_12_12_1$ with symmetry operations:

| | |
|---|---|
| 'x, y, z' | 1 |
| '−x+1/2, −y, z+1/2' | 2 |
| '−x, y+1/2, −z+1/2' | 3 |
| 'x+1/2, −y+1/2, −z' | 4 |

Figure 37:
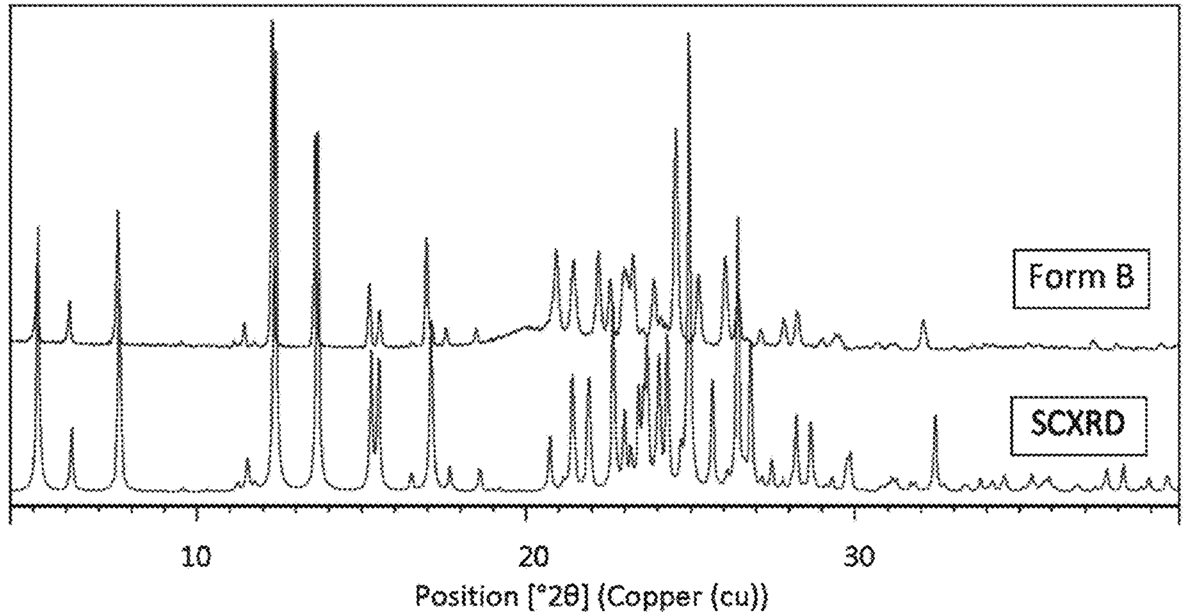
FIG. 37: PXRD comparison of the simulated pattern from the SCXRD (lower) with the reference form B pattern (upper).

FIG. 37 shows a comparative of an actual Form B pattern and the simulated pattern from the single crystal X-ray diffraction (SCXRD) data. Both correspond to the same crystalline phase. The small shifts observed are due to the different measurement temperatures.

Table 21 shows crystal data and structure refinement for crystalline Form B of Compound 1. Table 22 shows bond lengths [Å] for crystalline Form B of Compound 1. Table 22 shows bond angles [° ] for crystalline Form B of Compound 1. Table 23 shows torsion angles [° ] for crystalline Form B of Compound 1.

TABLE 21

| Crystal Data and Structure Refinement | | |
|---|---|---|
| Parameter | Value | |
| Temperature | 100(2)K | |
| Wavelength | 0.71073 Å | |
| Crystal system | orthorhombic | |
| Parameter | Value | |
| Space group | P 21 21 21 | |
| Unit cell dimensions | a = 4.3326(5) Å | α = 90° |
| | b = 15.7304(12) Å | β = 90° |
| | c = 34.251(3) Å | γ = 90° |
| Volume | 2334.3(4) $Å^3$ | |
| Z | 4 | |
| Density (calculated) | 1.336 $Mg/m^3$ | |
| Absorption coefficient | 0.090 $mm^{-1}$ | |
| F(000) | 992 | |
| Crystal size | 0.200 × 0.080 × 0.010 $mm^3$ | |
| Theta range for data collection | 2.379 to 29.270° | |
| Index ranges | −5 ≤ h ≤ 5, −18 ≤ k ≤ 21, −36 ≤ l ≤ 46 | |
| Reflections collected | 14567 | |
| Independent reflections | 5735[R(int) = 0.0998] | |
| Completeness to theta = 29.270° | 93.6% | |
| Absorption correction | Multi-scan | |
| Max. and min. transmission | 1.00 and 0.45 | |
| Refinement method | Full-matrix least-squares on $F^2$ | |
| Data/restraints/parameters | 5735/0/320 | |
| Goodness-of-fit on $F^2$ | 0.967 | |
| Final R indices [I > 2sigma(I)] | R1 = 0.0673, wR2 = 0.1412 | |
| R indices (all data) | R1 = 0.1353, wR2 = 0.1676 | |
| Flack parameter | x = 1.1(10) | |
| Largest diff. peak and hole | 0.328 and −0.371 e · $Å^{-3}$ | |

TABLE 22

| Bond lengths [Å] | | |
|---|---|---|
| C1 | C5 | 1.395(6) |
| C1 | C2 | 1.398(6) |
| C1 | C7 | 1.496(6) |
| N1 | C3 | 1.340(5) |
| N1 | C2 | 1.341(5) |
| O1 | C7 | 1.235(5) |
| C2 | H2 | 0.9500 |
| N2 | C7 | 1.377(5) |
| N2 | C8 | 1.416(5) |
| N2 | H2N | 0.8800 |
| O2 | C22 | 1.388(5) |
| O2 | C26 | 1.435(5) |
| C3 | C4 | 1.385(6) |
| C3 | H3 | 0.9500 |
| N3 | C16 | 1.363(5) |
| N3 | C14 | 1.473(5) |
| N3 | H3N | 0.8800 |
| O3 | C23 | 1.359(5) |
| O3 | C27 | 1.423(5) |
| C4 | C5 | 1.381(6) |
| C4 | C6 | 1.516(6) |
| N4 | C16 | 1.330(5) |
| N4 | C17 | 1.358(5) |

TABLE 22-continued

| Bond lengths [Å] | | |
|---|---|---|
| C5 | H5 | 0.9500 |
| N5 | C19 | 1.333(5) |
| N5 | C18 | 1.345(5) |
| C6 | H6A | 0.9800 |
| C6 | H6B | 0.9800 |
| C6 | H6C | 0.9800 |
| C8 | C9 | 1.390(5) |
| C8 | C13 | 1.406(5) |
| C9 | C10 | 1.384(6) |
| C9 | H9 | 0.9500 |
| C10 | C11 | 1.401(6) |
| C10 | C14 | 1.519(6) |
| C11 | C12 | 1.388(6) |
| C11 | H11 | 0.9500 |
| C12 | C13 | 1.388(6) |
| C12 | H12 | 0.9500 |
| C13 | H13 | 0.9500 |
| C14 | C15 | 1.514(6) |
| C14 | H14 | 1.0000 |
| C15 | H15A | 0.9800 |
| C15 | H15B | 0.9800 |
| C15 | H15C | 0.9800 |

TABLE 22-continued

| Bond lengths [Å] | | |
|---|---|---|
| C16 | C19 | 1.416(5) |
| C17 | C18 | 1.390(6) |
| C17 | C20 | 1.481(6) |
| C18 | H18 | 0.9500 |
| C19 | H19 | 0.9500 |
| C20 | C25 | 1.392(6) |
| C20 | C21 | 1.404(5) |
| C21 | C22 | 1.377(6) |
| C21 | H21 | 0.9500 |
| C22 | C23 | 1.412(6) |
| C23 | C24 | 1.387(6) |
| C24 | C25 | 1.386(6) |
| C24 | H24 | 0.9500 |
| C25 | H25 | 0.9500 |
| C26 | H26A | 0.9800 |
| C26 | H26B | 0.9800 |
| C26 | H26C | 0.9800 |
| C27 | H27A | 0.9800 |
| C27 | H27B | 0.9800 |
| C27 | H27C | 0.9800 |

TABLE 22

| Bond angles [°] | | | | | | | |
|---|---|---|---|---|---|---|---|
| C5 | C1 | C2 | 117.4(4) | C4 | C6 | H6C | 109.5 |
| C5 | C1 | C7 | 117.7(4) | H6A | C6 | H6C | 109.5 |
| C2 | C1 | C7 | 124.9(4) | H6B | C6 | H6C | 109.5 |
| C3 | N1 | C2 | 116.6(4) | O1 | C7 | N2 | 123.0(4) |
| N1 | C2 | C1 | 123.6(4) | O1 | C7 | C1 | 120.4(4) |
| N1 | C2 | H2 | 118.2 | N2 | C7 | C1 | 116.5(3) |
| C1 | C2 | H2 | 118.2 | C9 | C8 | C13 | 118.9(4) |
| C7 | N2 | C8 | 127.2(3) | C9 | C8 | N2 | 124.5(4) |
| C7 | N2 | H2N | 116.4 | C13 | C8 | N2 | 116.7(4) |
| C8 | N2 | H2N | 116.4 | C10 | C9 | C8 | 121.2(4) |
| C22 | O2 | C26 | 116.4(3) | C10 | C9 | H9 | 119.4 |
| N1 | C3 | C4 | 124.9(4) | C8 | C9 | H9 | 119.4 |
| N1 | C3 | H3 | 117.6 | C9 | C10 | C11 | 119.9(4) |
| C4 | C3 | H3 | 117.6 | C9 | C10 | C14 | 118.1(4) |
| C16 | N3 | C14 | 121.0(3) | C11 | C10 | C14 | 121.9(4) |
| C16 | N3 | H3N | 119.5 | C12 | C11 | C10 | 119.1(4) |
| C14 | N3 | H3N | 119.5 | C12 | C11 | H11 | 120.5 |
| C23 | O3 | C27 | 116.8(3) | C10 | C11 | H11 | 120.5 |
| C5 | C4 | C3 | 117.2(4) | C13 | C12 | C11 | 121.2(4) |
| C5 | C4 | C6 | 122.0(4) | C13 | C12 | H12 | 119.4 |
| C3 | C4 | C6 | 120.8(4) | C11 | C12 | H12 | 119.4 |
| C16 | N4 | C17 | 117.5(3) | C12 | C13 | C8 | 119.7(4) |
| C4 | C5 | C1 | 120.2(4) | C12 | C13 | H13 | 120.1 |
| C4 | C5 | H5 | 119.9 | C8 | C13 | H13 | 120.1 |
| C1 | C5 | H5 | 119.9 | N3 | C14 | C15 | 110.6(4) |
| C19 | N5 | C18 | 117.4(4) | N3 | C14 | C10 | 110.1(3) |
| C4 | C6 | H6A | 109.5 | C15 | C14 | C10 | 115.4(3) |
| C4 | C6 | H6B | 109.5 | N3 | C14 | H14 | 106.8 |
| H6A | C6 | H6B | 109.5 | C15 | C14 | H14 | 106.8 |
| C10 | C14 | H14 | 106.8 | C21 | C22 | 02 | 124.9(4) |
| C14 | C15 | H15A | 109.5 | C21 | C22 | C23 | 120.8(4) |
| C14 | C15 | H15B | 109.5 | O2 | C22 | C23 | 114.4(4) |
| H15A | C15 | H15B | 109.5 | O3 | C23 | C24 | 125.3(4) |
| C14 | C15 | H15C | 109.5 | O3 | C23 | C22 | 116.1(4) |
| H15A | C15 | H15C | 109.5 | C24 | C23 | C22 | 118.5(4) |
| H15B | C15 | H15C | 109.5 | C25 | C24 | C23 | 120.7(4) |
| N4 | C16 | N3 | 118.5(4) | C25 | C24 | H24 | 119.6 |
| N4 | C16 | C19 | 121.5(4) | C23 | C24 | H24 | 119.6 |
| N3 | C16 | C19 | 119.9(4) | C24 | C25 | C20 | 120.8(4) |
| N4 | C17 | C18 | 120.4(4) | C24 | C25 | H25 | 119.6 |
| N4 | C17 | C20 | 116.2(3) | C20 | C25 | H25 | 119.6 |
| C18 | C17 | C20 | 123.3(4) | O2 | C26 | H26A | 109.5 |
| N5 | C18 | C17 | 122.2(4) | H26A | C26 | H26B | 109.5 |
| N5 | C18 | H18 | 118.9 | O2 | C26 | H26C | 109.5 |
| C17 | C18 | H18 | 118.9 | H26A | C26 | H26C | 109.5 |
| NS | C19 | C16 | 120.8(4) | H26B | C26 | H26C | 109.5 |
| N5 | C19 | H19 | 119.6 | O3 | C27 | H27A | 109.5 |
| C16 | C19 | H19 | 119.6 | O3 | C27 | H27B | 109.5 |
| C25 | C20 | C21 | 118.8(4) | H27A | C27 | H27B | 109.5 |

TABLE 22-continued

| Bond angles [°] | | | | | | | |
|---|---|---|---|---|---|---|---|
| C25 | C20 | C17 | 119.7(4) | O3 | C27 | H27C | 109.5 |
| C21 | C20 | C17 | 121.5(4) | H27A | C27 | H27C | 109.5 |
| C22 | C21 | C20 | 120.3(4) | H27B | C27 | H27C | 109.5 |
| C22 | C21 | H21 | 119.8 | O2 | C26 | H26B | 109.5 |
| C20 | C21 | H21 | 119.8 | | | | |

TABLE 23

| Torsion angles [°] | | | | | | | | | |
|---|---|---|---|---|---|---|---|---|---|
| C3 | N1 | C2 | C1 | 1.6(7) | C7 | N2 | C8 | C9 | −5.3(7) |
| C5 | C1 | C2 | N1 | −0.1(7) | C7 | N2 | C8 | C13 | 175.4(4) |
| C7 | C1 | C2 | N1 | 180.0(4) | C13 | C8 | C9 | C10 | −3.9(6) |
| C2 | N1 | C3 | C4 | −1.2(7) | N2 | C8 | C9 | C10 | 176.8(4) |
| N1 | C3 | C4 | C5 | −0.9(7) | C8 | C9 | C10 | C11 | 3.6(6) |
| N1 | C3 | C4 | C6 | 178.1(5) | C8 | C9 | C10 | C14 | −173.2(4) |
| C3 | C4 | C5 | C1 | 2.5(7) | C9 | C10 | C11 | C12 | −1.6(7) |
| C6 | C4 | C5 | C1 | −176.4(4) | C14 | C10 | C11 | C12 | 175.2(4) |
| C2 | C1 | C5 | C4 | −2.1(7) | C10 | C11 | C12 | C13 | −0.2(7) |
| C7 | C1 | C5 | C4 | 177.9(4) | C11 | C12 | C13 | C8 | 0.0(7) |
| C8 | N2 | C7 | O1 | −3.8(7) | C9 | C8 | C13 | C12 | 2.0(6) |
| C8 | N2 | C7 | C1 | 174.4(4) | N2 | C8 | C13 | C12 | −178.6(4) |
| C5 | C1 | C7 | O1 | 24.0(6) | C16 | N3 | C14 | C15 | −82.6(5) |
| C2 | C1 | C7 | O1 | −156.0(4) | C16 | N3 | C14 | C10 | 148.7(4) |
| C5 | C1 | C7 | N2 | −154.3(4) | C9 | C10 | C14 | N3 | −54.4(5) |
| C2 | C1 | C7 | N2 | 25.7(6) | C11 | C10 | C14 | N3 | 128.8(4) |
| C9 | C10 | C14 | C15 | 179.6(4) | C25 | C20 | C21 | C22 | 0.9(6) |
| C11 | C10 | C14 | C15 | 2.8(6) | C17 | C20 | C21 | C22 | −177.9(4) |
| C17 | N4 | C16 | N3 | −177.1(4) | C20 | C21 | C22 | O2 | 179.4(4) |
| C17 | N4 | C16 | C19 | 2.1(6) | C20 | C21 | C22 | C23 | −0.9(6) |
| C14 | N3 | C16 | N4 | 3.2(6) | C26 | O2 | C22 | C21 | −7.4(6) |
| C14 | N3 | C16 | C19 | −176.0(4) | C26 | O2 | C22 | C23 | 172.9(4) |
| C16 | N4 | C17 | C18 | 1.4(6) | C27 | O3 | C23 | C24 | 0.9(6) |
| C16 | N4 | C17 | C20 | 179.5(4) | C27 | O3 | C23 | C22 | −178.7(4) |
| C19 | N5 | C18 | C17 | 1.2(6) | C21 | C22 | C23 | O3 | 179.5(4) |
| N4 | C17 | C18 | N5 | −3.2(6) | O2 | C22 | C23 | O3 | −0.8(6) |
| C20 | C17 | C18 | N5 | 178.9(4) | C21 | C22 | C23 | C24 | −0.1(7) |
| C18 | N5 | C19 | C16 | 2.3(6) | O2 | C22 | C23 | C24 | 179.6(4) |
| N4 | C16 | C19 | N5 | −4.1(7) | O3 | C23 | C24 | C25 | −178.4(4) |
| N3 | C16 | C19 | N5 | 175.0(4) | C22 | C23 | C24 | C25 | 1.1(7) |
| N4 | C17 | C20 | C25 | −11.1(6) | C23 | C24 | C25 | C20 | −1.2(7) |
| C18 | C17 | C20 | C25 | 166.9(4) | C21 | C20 | C25 | C24 | 0.2(6) |
| N4 | C17 | C20 | C21 | 167.7(4) | C17 | C20 | C25 | C24 | 179.0(4) |
| C18 | C17 | C20 | C21 | −14.3(7) | | | | | |

Example 8

Micronization of Crystalline Compound 1

For inhalation formulation purposes it was desirable to obtain Compound 1 with a small particle size, preferably having a Dv50 of 2-3 μm. To this end, various particle engineering technologies were evaluated to generate a stable micronized Compound 1 that retained its crystalline form and starting material purity. The processes evaluated included:

Jet milling—involving the feeding a powder into a milling chamber where compressed nitrogen, in a vortex motion, promotes particle-to-particle collisions, thereby reducing particle size;

Wet milling—involving the microfluidization of a suspension by high pressure homogenization (HPH); and Wet polishing—involving the combination of wet milling of a suspension followed by isolation via spray drying, i.e. the three step process of:

(i) preparing a feed suspension;

(ii) microfluidization of the suspension by high pressure homogenization (HPH); and (iii) spray drying the suspension to isolate the micronized particles.

The advantages of wet polishing, relative to jet milling, include precise control over the particle size distribution and a smoother final surface area, potentially enabling for high dosage/neat substance formulations.

I Particle Size Reduction—Jet Milling

Crystalline Compound 1 Form A was fed into a grinding chamber tangentially by vacuum created by the venturi system using pressurized nitrogen (venturi pressure, $P_{vent}$, above grind pressure, $P_{grind}$). Compressed nitrogen was also used for the jet nozzles in the walls of the chamber. The feed flow rate was set and controlled automatically (by a gravimetric feeder) or manually. Once inside the milling chamber particles were accelerated by a series of perimeter jets, in a spiral movement. The compressed fluid issuing from the nozzles expands from $P_{grind}$ and imparts very high rotational speeds in the chamber. The micronizing effect occurs when the slower incoming particles and the faster particles in the spiral path collide. While centrifugal force retains the larger particles at the periphery of the milling chamber, the smaller particles exit with the exhaust gas from the center of the chamber. Five 20 g trials were performed in a 1.5" jet mill, under varying feed rates ($F_{feed,JM}$,) and pressures; the optimal conditions were used for a sixth larger scale 50 g trial. The conditions for each run and analyses of the resulting micronized material, are presented in Table 24.

TABLE 24

Jet Mill & Product Characterization of Micronized Crystalline Compound 1 Form A

| | Run: | | | | | |
|---|---|---|---|---|---|---|
| | 1 | 2 | 3 | 4 | 5 | 6 |
| Charaterization | 1 | 2 | 3 | 4 | 5 | 6 |
| Water content KF (% w/w) | 1.4 | — | 0.5 | 0.6 | — | 0.7 |
| XRPD | P + A | — | P | P | — | P |
| Assay (% LC) | 97.70 | — | 99.30 | 98.20 | — | 98.20 |
| Impurities (% area) | 1.10 | — | 1.00 | 0.98 | — | 0.72 |
| Amorphous content by DSC (% w/w) | 46 | — | 19 | 13 | — | 19 |
| Specific Surface Area by BET | 10.35 | — | 11.54 | 14.51 | — | 10.7 |
| Dv10 (μm) | 0.4 | 0.5 | 0.6 | 0.7 | 0.6 | 0.5 |
| Dv50 (μm) | 1.2 | 1.4 | 1.9 | 2.4 | 2.2 | 1.6 |
| Dv90 (μm) | 2.8 | 3.3 | 13.3 | 23.4 | 19.9 | 3.9 |
| SPAN | 2.0 | 2.0 | 6.6 | 9.5 | 8.9 | 2.1 |

P = Crystalline Form
A = Amorphous

II Particle Size Reduction—Wet Polishing (Wet Milling+ Spray Drying)

Step 1—Wet Milling

Aqueous suspensions of crystalline Compound 1 Form A in water (5% w/w or 10% w/w) were processed via microfluidization with a HPH18 (M-110EH-30 Microfluidics Pilot) wet milling apparatus equipped with an auxiliary processing module (200 μm) and an interaction chamber (Z-shape, 100 μm). The unit was initiated at a given pressure for the first five cycles to perform a pre-milling of the suspension, using only the auxiliary processing module (200 μm). The interaction chamber (100 μm) was then introduced and the suspension processed at a defined pressure. The temperature was controlled, using a reactor jacket, and recorded. To address clogging of the micronization chambers (observed after ~25 cycles), the pressure was increased from 25 to 60 bar. Analyses of the resulting micronized material are presented in Tables 25 and 26.

TABLE 25

| Wet milling | | | |
|---|---|---|---|
| Parameter | Run 1A | RUN 2A | RUN 3A |
| Weight Compound 1 (g) | 25 | 50 | 350 |
| Weight water (g) | 475 | 950 | 3500 (+1000) |
| $C_{solids}$ (% w/w) | 5 | 5 | 10 |
| Yield (%) | | — | 85% |

TABLE 26

Wet Milling - Product Characterization

| Number of cycles/Pressure | Dv10 (μm) | Dv50 (μm) | Dv90 (μm) |
|---|---|---|---|
| Run 1A | | | |
| 30/P = 60 bar | 1.7 | 3.2 | 6 |
| Run 2A | | | |
| 45/P = 50 bar | 1.3 | 2.7 | 4.8 |
| Run 3A | | | |
| 30/P = 50 bar | 0.1 | 1.0 | 3.5 |

Step 2—Spray Drying

The wet-milled material was then spray dried using an SD48 BÜCHI model B-290 Advanced spray dryer, equipped with a two fluid nozzle and one high-performance cyclone to collect the dried product. The unit was operated in a closed cycle, with the aspirator blowing nitrogen at 100% capacity (flow rate of drying nitrogen, $F_{drying}$, at maximum capacity is approximately 20 kg/h). The flow rate of the atomization nitrogen was adjusted to a value in the rotameter of 40 mm. Before feeding the stock suspension, the spray dryer was stabilized with water and the flow rate adjusted. The inlet temperature was adjusted to achieve the target outlet temperature. Samples were subjected to varying process conditions to assess the impact of feed mixture flow rate, ($F_{feed,SD}$), drying gas temperature at the outlet of the spray drying chamber, Tout.

The material isolated from the first run 1A, was dived into three (1BI, 1BII and 1BIII); runs 2A and 3A were spray dried to produce samples 2B and 3B, respectively. The resulting materials were characterized for PSD, XRPD, amorphous content, water content and assay & related substances. Runs 2B and 3B were additionally characterized for specific surface area (SSA). See Table 27 (runs 1BI, 1BII and 1BIII) and Table 28 (runs 2B and 3B) for conditions and product characterization.

TABLE 27

Spray Drying Conditions and Product Characterization (Runs 1BI, 1BII and 1BIII)

| | 1BI | 1BII | 1BIII |
|---|---|---|---|
| Process parameters | | | |
| Theoretical mass (g) | 165 | 165 | 215* |
| Theoretical Cmpd 1 (g) | 8 | 8 | 8 |
| Tin (° C.) | 144-166 | 128-132 | 168-174 |
| Tout measured (° C.) | 74-78 | 64-66 | 74-75 |
| Output (g) | 4.0 | 2.8 | 4.0 |
| SD theoretical yield (%) | 50 | 35 | 50 |
| Product characterization | | | |
| Dv10 (μm) 1 | 1.8 | 1.7 | 1.7 |
| Dv50 (μm) 1 | 3.5 | 3.3 | 3.4 |
| Dv90 (μm) 1 | 6.6 | 6.3 | 6.6 |
| SPAN1 | 1.4 | 1.4 | 1.4 |
| Dv10 (μm) 2 | 1.5 | 1.3 | 1.4 |
| Dv50 (μm) 2 | 3.3 | 3 | 3.1 |
| Dv90 (μm) 2 | 6.7 | 6.1 | 6.6 |
| SPAN 2 | 1.6 | 1.6 | 1.7 |
| XRPD | Crystalline Form A | Crystalline Form A | Crystalline Form A |
| Amorphous content (% w/w) | <10 | <10 | <10 |
| KF (% w/w) | 0.5 | 0.2 | 0.1 |
| Assay (% LC) | 98.9 | 102.0 | 99.40 |
| Impurities (% area) | 1.1 | 0.9 | 1.10 |

*50 mL water added

TABLE 28

| Spray Drying Conditions and Product Characterization (Runs 2B and 3B) | | | |
|---|---|---|---|
| | 2B | 3B | 3B-2F |
| Process parameters | | | |
| Theoretical mass (g) | 1000 | 3828 (+500) | |
| Theoretical Cmpd 1 amount (g) | — | 298 | |
| Tin (° C.) | 144-182 | 161-185 | 187-193 |
| Tout measured (° C.) | 72-77 | 73-76 | 82 |
| Output (g) | 18.5 | 67.6 | 7.2 |
| SD theoretical yield (%) | — | 23 | 25 |
| Overall process yield (%) | 37 | 19 | — |
| Product characterization | | | |
| Dv10 (μm) 1 | 0.5 | — | — |
| Dv50 (μm) 1 | 1.3 | — | — |
| Dv90 (μm) 1 | 2.9 | — | — |
| SPAN1 | 1.8 | — | — |
| Dv10 (μm) 2 | 1.5 | 0.6 | 1.3 |
| Dv50 (μm) 2 | 3.7 | 2.6 | 3.7 |
| Dv90 (μm) 2 | 8.3 | 5.0 | 14.7 |
| SPAN 2 | 1.8 | 1.7 | 3.6 |
| XRPD | Crystalline | Crystalline | — |
| Amorphous content (% w/w) | <10% | <10% | — |
| KF (% w/w) | 0.4 | 0.5 | — |
| Assay (% LC) | 98.7 | 95.7 | — |
| Impurities (% area) | 1.0 | 1.0 | — |
| SSA ($m^2/g$) | 24.6045 | — | — |

III Capsule Filling

Micronized material, prepared by jet-milling or wet polishing, as described above in section I or II respectively, was filled into Transparent Hydroxypropyl Methylcellulose (HPMC) size #3 capsules. More specifically, Transparent HPMC size #3 capsules were filled using an auger-filling Quantos unit, with 100% net weight check and nominal throughput ~100 caps/h. The Quantos was placed inside a climatically controlled enclosure (CTS ClimateZone unit), set at 20-25° C. and 40±5% relative humidity (exact conditions recorded). Micronized crystalline Compound 1 Form A was sieved through a 250 μm mesh and then conditioned for at least 2 hours at 20-25° C. and 40±10% relative humidity. The conditioned material was charged to a Quantos dosator head. The capsules were filled with 10.0 and 20.0 mg with a rejection limit of +5% of the fill weight. The filled weight of each capsule was automatically recorded and categorized as PASS or FAIL. After each filling cycle, FAILED capsules were discarded, and PASS capsules were closed manually. The cycle was repeated until 60 capsules were filled. Notably, the wet polished powder appeared to have a lower density than the jet milled powder, based on the space the same amount of powder (20 mg) occupies in the capsule. A total of 8 batches were prepared using:

three jet milled powders from RUNS 1, 4 & 6;

wet polished powder 2B;

3 different HPMC size #3 capsules from 3 different suppliers Capsugel, Ravago and Qualicaps; and 2 fill weights (10 mg and 20 mg).

The materials used, manufacturing parameters and capsule characterization for each trial are summarized in Table 29.

TABLE 29

| Materials, Manufacturing Parameters and Capsule Characterization | | | | | | | | |
|---|---|---|---|---|---|---|---|---|
| | BATCH: | | | | | | | |
| Material | 1 | 2 | 3 | 4 | 5 | 6 | 7 | 8 |
| Process | JM | JM | JM | JM | JM | JM | WP | WP |
| RUN | 1 | 4 | 6 | 6 | 6 | 6 | 2B | 2B |
| AC (%) | 46% | 13% | 19% | 19% | 19% | 19% | <10% | <10% |
| Dv10 (μm) | 0.4 | 0.7 | 0.5 | 0.5 | 0.5 | 0.5 | 0.5 | 0.5 |
| Dv50 (μm) | 1.2 | 2.4 | 1.6 | 1.6 | 1.6 | 1.6 | 1.3 | 1.3 |
| Dv90 (μm) | 2.8 | 23.4 | 3.9 | 3.9 | 3.9 | 3.9 | 2.9 | 2.9 |
| Capsules | C | C | C | Q | C | R | C | C |
| T (° C.) | 23 | 23 | 17-19 | 17-23 | 23 | 22 | 23 | 23 |
| RH (%) | 35 | 35 | 39-41 | 42-35 | 35 | 37 | 34-35 | 35 |
| No. capsules | 50 | 50 | 53 | 60 | 50 | 41 | 60 | 49 |
| Fill weight (mg) | 19.9 ± 0.2 | 19.8 ± 0.2 | 19.6 ± 0.5 | 19.6 ± 0.4 | 10.0 ± 0.2 | 20.0 ± 0.2 | 19.4 ± 0.2 | 19.8 ± 0.4 |
| FPD (mg/caps) | 8.8 ± 0.3 | 4.3 ± 1.2 | 6.3 ± 0.6 | 6.9 ± 0.5 | 3.8 ± 0.5 | 7.0 ± 0.7 | 8.6 ± 1.4 | 7.7 ± 0.3 |
| $ED_{NGI}$ (mg/caps) | 16.5 ± 1.0 | 17.6 ± 1.5 | 15.9 ± 0.1 | 18.4 ± 0.5 | 9.0 ± 0.8 | 17.9 ± 0.7 | 15.9 ± 0.7 | 16.1 ± 0.2 |
| MMAD (μm) | 2.7 | 2.8 | 2.9 | 3.1 | 2.6 | 3.0 | 2.8 | 3.0 |
| GSD | 1.8 | 2.0 | 1.9 | 1.9 | 1.9 | 1.9 | 2.0 | 2.1 |
| ED (mg/caps) | 18.5 ± 0.7 | 19.5 ± 0.3 | 18.9 ± 0.8 | 19.2 ± 2.3 | 9.6 ± 0.4 | 19.3 ± 0.4 | 16.7 ± 0.7 | 18.3 ± 0.5 |
| $FPF_{ED}$ (%) | 47.6 ± 1.1 | 22.1 ± 4.9 | 33.4 ± 2.5 | 36.1 ± 2.0 | 39.3 ± 4.4 | 36.2 ± 3.0 | 51.8 ± 7.0 | 42.0 ± 1.2 |
| Recovery % ($ED_{NGI}/ED_{DUSA}$) | 89 | 90 | 84 | 96 | 94 | 93 | 96 | 88 |

JM = Jet milling;

WP = Wet polishing

Capsules: C = Capsugel; Q = Qualicaps; R = Ravago

AC = Amorphous content

Example 9

Effect of Adding a Force Control Agent (L-Leucine)

Step 1: Micronization

Crystalline Compound 1 Form A (100 g) suspended in water (1900 g) (5.0% w/w) was micronized by wet-milling, according to step I above. The suspension was pre-milled for five cycles, using only the auxiliary processing module (200 μm), followed by 40 cycles using the interaction chamber, both at 50 bar pressure. Conditions are presented in Table 30. PSD samples were taken after various cycles, with the results after 45 cycles shown in Table 31.

TABLE 30

| Micronization Conditions | |
|---|---|
| Parameter | Value |
| Weight compound 1 (g) | 100 |
| Weight water (g) | 1900 |
| Total mass (g) | 2000 |
| $C_{solids}$ (% w/w) | 5 |
| Output amount (g) | 1878 |
| Yield (%) | 94 |
| Suspension temperature (° C.) | 19-28 |
| Output chamber temperature (° C.) | 14-31 |

TABLE 31

| Particle Size Analyses | | | |
|---|---|---|---|
| Number of cycles/Pressure | Dv10 (μm) | Dv50 (μm) | Dv90 (μm) |
| 45/P = 50 bar | 0.1 | 1.0 | 3.5 |

Step 2: Spray Drying with L-Leucine

The above micronized material was divided into 3 approximately equal batches and coated with increasing leucine content by spay-drying using a BÜCHI SD41 spray dryer with a similar set up as described in Step 2—Spray Drying of Example 8, resulting in 3 batches with different leucine concentrations (2A, 2B and 2C). Materials were evaluated for PSD, SEM, assay and XRPD. The spray drying process parameters and product characterization are presented in Table 32. XRPD showed the characteristic peaks for the crystalline Compound 1 Form A, but not those for crystalline L-leucine suggesting the L-leucine is amorphous form in the spray dried material.

TABLE 32

| Spray Drying Conditions and Product Characterization | | | |
|---|---|---|---|
| | 2A | 2B | 2C |
| Parameter | | | |
| Theoretical Cmpd 1 (g) | 31.4 | 31.0 | 31.5 |
| Leucine added (g) | 0.628 | 1.861 | 3.152 |
| Total mass (g) | 628 | 620 | 630 |
| $T_{in}$ (° C.) | 153-172 | 156-161 | 163-164 |
| $T_{out}$ measured (° C.) | 73-75 | 73-77 | 74-75 |
| Output (g) | 17.4 | 18.2 | 5.9 |
| Characterization | | | |
| Dv10 (μm) | 0.2 | 0.4 | 0.5 |
| Dv50 (μm) | 1.7 | 2.3 | 2.3 |

TABLE 32-continued

| Spray Drying Conditions and Product Characterization | | | |
|---|---|---|---|
| | 2A | 2B | 2C |
| Dv90 (μm) | 4.3 | 5.1 | 5.0 |
| SPAN | 2.3 | 2.0 | 1.9 |
| Assay (% LC) | 98.6 ± 0.1 | 93.0 ± 0.7 | 76.5 ± 0.1 |
| Impurities (% area) | 0.97 | 0.93 | 0.95 |
| Leucine content % | ~2 | ~7 | ~24 |

Step 3: Capsule Filling

The micronized, spray dried material was filled into capsules according to STEP III above. Three capsule batches were prepared from the three spray dried products, using #3 HMPC Capsugel capsule shells. Capsules were filled with the following (the capsules had a rejection limit of ±5% of the fill weight):

20 mg 2A powder to 3A capsules;
15 mg 2B powder to 3B capsules; or
15 mg 2C powder to 3C capsules.

The filled capsules were analyzed for NGI (n=3) and DUSA (n=10) and the manufacturing data and capsule characterization presented in Table 33. Notably, the powder flow during the capsule filling process was noticeably worse with added L-leucine, as compared to compound 1 alone, in particular for the higher leucine content formulations. As a result, the fill-weight was decreased from 20 to 15 mg due to powder adherence to the capsule shell interior wall.

TABLE 33

| Manufacturing Parameters and Capsule Characterization for Capsules Containing Compound 1 Plus Leucine | | | |
|---|---|---|---|
| | 3A | 3B | 3C |
| Material used: | 2A | 2B | 2C |
| Manufacturing parameters | | | |
| Fill weight (mg) | 19.9 ± 0.3 | 15.0 ± 0.2 | 15.0 ± 0.2 |
| No. capsules | 55 | 58 | 55 |
| T (° C.) | 23 | 23 | 23 |
| RH (%) | 36 | 35-36 | 35-36 |
| Capsule characterization | | | |
| FPD (mg/caps) | 12.1 ± 0.9 | 8.4 ± 0.8 | 6.4 ± 0.1 |
| $ED_{NGI}$ (mg/caps) | 17.3 ± 0.5 | 12.1 ± 1.0 | 8.8 ± 0.3 |
| MMAD (μm) | 2.4 | 2.4 | 2.4 |
| GSD | 1.9 | 2.1 | 2.0 |
| ED (mg/capsule) | 18.5 ± 1.0 | 12.9 ± 0.7 | 10.2 ± 0.4 |
| ED (% of drug load) | 94 | 92 | 89 |
| $FPF_{ED, DUSA}$ (%) | 65.4 ± 3.9 | 65.0 ± 5.1 | 62.9 ± 1.1 |
| Recovery % ($ED_{NGI}/ED_{DUSA}$) | 94 | 94 | 86 |

FPD: Fine Particle Dose
ED: Emitted Dose (from inhaler)
NGI: Next Generation Impactor
DUSA: Dosage Unit Sampling Apparatus
MMAD: Mass Median Aerodynamic Diameter
$FPF_{ED, DUSA}$: Fine Particle Fraction (Fine Particle Dose over the Emitted Dose by DUSA)
$FPF_{ED, NGI}$: Fine Particle Fraction (Fine Particle Dose over the Emitted Dose by NGI)
GSD: Geometric Standard Deviation Example 10

Carrier Based Formulation

To investigate aerodynamic performance optimization, six carrier-based formulations were examined employing three blending mechanisms: two low shear mixing by Turbula, two high shear mixing by Diosna, and two milling with jet milling. The blending and capsule filling parameters are presented in Table 35 and the characterization of capsules filled with the mixtures as is presented in Table 36. L-Leucine or Lactose were used as carriers. Two grades of lactose were used:

Respitose SV003—sieved lactose crystals with smooth surface and mean particle size >50 μm (Dv10=19-43 μm/Dv50=53-66 μm/Dv90=75-106 μm); Bulk density=630 g/L; and Tablettose 80—granulated lactose with particle size 0-630 μm (<63 μm NMT 20%, <180 μm 40-75%, <400 μm NLT 85%, <63 μm NLT 97%; mean ~300 μm); bulk density=620 g/L.

High Shear Mixing

High shear mixing was performed using a Diosna high shear mixer with a 0.5 L bin. Lactose was sieved (Respitose SV003=500 μm sieve; Tablettose 80=850 μm sieve) and loaded. Crystalline Compound 1 Form A was sieved (same sieve as lactose) and loaded and the combined material mixed for 5 minutes at 450 RPM in the main impeller and 500 RPM in the chopper. Batch sizes were 20-30 g, comprising 60% micronized compound 1 and 40% lactose.

Low Shear Mixing

Low shear mixing was performed using a Glen Mills T2F Turbula with a 0.5 L flask. Lactose was sieved (Respitose SV003=500 μm sieve; Tablettose 80=850 μm sieve) and loaded. Crystalline Compound 1 Form A was sieved (same sieve as lactose) and loaded and the combined material mixed for 15 minutes at 96 RPM. Batch sizes were 15 g, comprising 60% micronized compound 1 and 40% lactose.

Co-Milling

Crystalline Compound 1 Form A and excipient (Lactose or leucine) were blended using the Turbula low shear mixer at 96 RPM for 15 minutes. The blended material was fed into a MZ0502 jet mill at 60 g/hour and micronized (grinding pressure=4-5.5 bar, venting pressure=6-7 bar). Compound 1 (60%) with lactose (7711.01) and Compound 1 (96%) with L-leucine (7603.02).

Capsule Filling

The six mixtures were filled into capsules, using the auger filler Quantos according to previously described procedure. Significant differences were not observed during capsule filling for the different formulations. The filled capsules were analyzed for NGI (n=3) and DUSA (n=10). The results are summarized in Tables 34 and 35.

TABLE 34

Materials and Parameters for Carrier-Based Formulations

| | RUN | | | | | |
|---|---|---|---|---|---|---|
| | 1 | 2 | 3 | 4 | 5 | 6 |
| Cmpd 1 Form A (g) | 18 | 12 | 9 | 9 | 21 | 21 |
| Cmpd 1 Form A (%) | 60 | 60 | 60 | 60 | 60 | 96 |
| Excipient | R | T | R | T | R | Leu |
| Excipient (g) | 12 | 8 | 6 | 6 | 14 | 1 |
| Total mass (g) | 30 | 20 | 15 | 15 | 35 | 22 |
| Yield (%) | 67 | 63 | 71 | 71 | 87 | 83 |
| Process | HS | HS | LS | LS | JM | JM |
| T (° C.) | 20 | 20 | 21 | 20 | 21 | 20 |
| RH (%) | 51 | 51 | 51 | 52 | 50 | 52 |
| No. capsules | 88 | 63 | 60 | 57 | 55 | 54 |
| Fill wt (target) | 30 | 30 | 30 | 30 | 30 | 20 |
| Fill wt (mg) | 29.9 ± 0.3 | 29.7 ± 0.4 | 29.8 ± 0.2 | 29.9 ± 0.3 | 29.8 ± 0.3 | 20.0 ± 0.3 |

R = Respitose SV003
T = Tablettose 80
HS = High Shear
LS = Low Shear
JM = Jet Miliing

TABLE 35

Capsule Characterization for Carrier-Based Formulations

| | 1 | 2 | 3 | 4 | 5 | 6 |
|---|---|---|---|---|---|---|
| Blend uniformity analysis (BUA) | | | | | | |
| Average (%) | 58.8 | 52.6 | 52.0 | 57.5 | 55.7 | 93.6 |
| RSD (%) | 2.1 | 8.8 | 3.9 | 6.1 | 0.7 | — |
| PSD of co-milled formulations | | | | | | |
| Dv10 (μm) 1 | — | — | — | — | 0.6 | 0.6 |
| Dv50 (μm) 1 | — | — | — | — | 1.9 | 2.2 |
| Dv90 (μm) 1 | — | — | — | — | 4.6 | 8.0 |
| SPAN | | | | | 2.1 | 3.4 |
| Capsule characterization | | | | | | |
| Assay (% LC) | 58.77 | 54.3 | 50.39 | 56.68 | 56.04 | 93.6 |
| Impurities (% area) | 0.89 | 0.89 | 0.95 | 0.95 | 0.97 | 0.23 |
| FPD (mg/caps) | 9.1 ± 0.8 | 7.4 ± 1.2 | 3.5 ± 10.8 | 7.3 ± 0.7 | 3.2 ± 0.6 | 4.6 ± 03.0 |
| EDNGI (mg/caps) | 14.7 ± 0.7 | 14.9 ± 1.4 | 15.3 ± 0.8 | 14.9 ± 1.2 | 16.9 ± 0.2 | 16.2 ± 1.1 |
| FPFED (%) | 62.1 ± 2.2 | 49.8 ± 3.1 | 22.6 ± 3.3 | 48.6 ± 3.8 | 20.7 ± 0.3 | 27.5 ± 16.7 |
| MMAD | 2.9 ± 0.1 | 2.9 ± 0.1 | 3.1 ± 0.5 | 2.8 ± 0.2 | 3.0 ± 0.2 | 2.8 ± 0.2 |
| GSD | 1.8 | 1.9 ± 0.1 | 2.1 ± 0.1 | 2.0 ± 0.1 | 2.0 ± 0.1 | 2.5 ± 0.1 |
| ED (mg/caps) | 16.6 ± 0.5 | 15.6 ± 2.0 | 14.5 ± 0.9 | 15.1 ± 1.0 | 16.1 ± 0.2 | 18.0 ± 0.6 |

TABLE 35-continued

| Capsule Characterization for Carrier-Based Formulations | | | | | | |
|---|---|---|---|---|---|---|
| | 1 | 2 | 3 | 4 | 5 | 6 |
| ED (% of drug load) | 94 | 96 | 96 | 89 | 96 | 96 |
| FPFED (%) | 55 ± 4 | 47 ± 6 | 24 ± 2 | 48 ± 4 | 20 ± 3 | 25 ± 10 |
| Recovery % (EDNGI/EDDUSA) | 88 | 96 | 106 | 99 | 105 | 90 |

Example 11

High-Dosage Crystalline Dry Powder Inhaler (Dpi) Formulation

I Wet Polishing—Compound 1 Alone

Two 250 g batches of crystalline Compound 1 Form A were each suspended in water (5 L) and wet polished in a wet milling HPH18 (M-110EH-30 Microfluidics Pilot) apparatus, equipped with an auxiliary processing module (200 μm) and an interaction chamber (Z-shape, 100 μm). The unit was initiated at 50 bar for the first five cycles to perform a pre-milling of the suspension, using only the auxiliary processing module (200 μm). The interaction chamber (100 μm) was then introduced and the suspension processed at 50 bar (increased to 60 or 70 bar if the system clogged). The temperature was maintained at 18-28° C. using a reactor jacket. The Reactor agitation speed was 280 RPM (batch 1) and 390 RPM (batch 2). The first batch was micronized for 25 cycles and particle size distribution analyzed after 5, 15 and 20 cycles; the second batch was micronized for 3525 cycles and particle size distribution analyzed after 15, 20, 25 and 35 cycles. The particle size distribution analyses are shown in Table 36.

TABLE 36

| PSD Analyses for Compound 1 Alone After Wet Milling | | | |
|---|---|---|---|
| Number of cycles/Pressure | Dv10 (μm) | Dv50 (μm) | Dv90 (μm) |
| BATCH 01 | | | |
| 20/P = 50 bar | 0.2 | 0.5 | 1.7 |
| BATCH 02 | | | |
| 35/P = 70 bar | 0.3 | 0.8 | 3.4 |

Both batches were then spray dried (separately) using a Büchi spray dryer, using an open loop system. The unit was equipped with a two-fluid nozzle: cap and orifice diameters of 1.5 and 0.7 mm, respectively operated with nitrogen. The aspirator, blowing nitrogen, was set at 100% capacity (~40 kg/h). The suspension feed flow was set to 8 ml/min, high and the drying outlet temperature to 75±1° C. The final blend of spray dried powder was characterized for particle size distribution (PSD), water content by KF, XRPD and amorphous content (DSC), details shown in Table 37. Total yield (both batches combined) was 267 g (53%).

TABLE 37

| Spray Drying Conditions for Compound 1 Alone | | |
|---|---|---|
| Parameter | BATCH 01 | BATCH 02 |
| Input amount (g) | 5000 | 5000 |
| Compound 1 (g) | 250 | 250 |

TABLE 37-continued

| Spray Drying Conditions for Compound 1 Alone | | |
|---|---|---|
| Parameter | BATCH 01 | BATCH 02 |
| $D_{drying}$ (kg/h) | 35 | 35 |
| $T_{in}$ (° C.) | 150-155 | 155-166 |
| $T_{out}$ measured (° C.) | 74-76 | 74-76 |
| Output cyclone 1 (g) | 124 | 126 |
| Output cyclone 2 (g) | 8 | 9 |

Both batches presented a particle size distribution 0.5<Dv50<3 μm, with little difference between the two batches, as shown in Table 38.

TABLE 38

| Particle Size Distribution | | | | |
|---|---|---|---|---|
| Individual batch Analyses | | | | |
| Cyclone | 1 | 2 | 1 | 2 |
| Dv10 (μm) | 0.1 | 0.1 | 0.3 | 0.3 |
| Dv50 (μm) | 0.4 | 0.4 | 0.5 | 0.5 |
| Dv90 (μm) | 3.1 | 2.9 | 1.5 | 1.4 |
| SPAN | 7.2 | 7.9 | 2.1 | 2.0 |

The final product showed a Dv50 of 0.6 μm, with the expected amorphous content, water content and XRPD peaks, as shown Table 39.

TABLE 39

| Final Product Analyses | |
|---|---|
| Final Product Analyses | |
| Dv10 (μm) | 0.3 |
| Dv50 (μm) | 0.6 |
| Dv90 (μm) | 3.3 |
| SPAN1 | 4.7 |
| Amorphous content by DSC (% w/w) | <10 |
| XRPD | Form A |
| Assay (% LC) | 101.1 |
| Impurities (% area) | 1.2 |
| KF (% w/w) | 0.3 |
| Bulk density (g/ml) 1 | 0.10 |

II Wet Polishing—Compound 1 Coated with L-Leucine

Two 250 g batches (250 g and 238 g; 488 g total) of crystalline Compound 1 Form A coated with ~2% L-leucine were each suspended in water (5 L) and wet polished in a wet milling HPH18 (M-110EH-30 Microfluidics Pilot) apparatus, under the same process as described in the previous example. The first batch was micronized for 25 cycles and the second for 30 cycles. Samples were taken before the milling process, and after 5, 10, 15, 20 and 25 cycles for the first batch and after 30 cycles for the second batch. Clogging of the micronization chambers was minimized by using a 50 bar pressure for the first 5 cycles (200 μm chamber) and 70 bar for the remaining cycles (200 μm and 100 μm chamber). The suspension was weighed at the start and at the end of the process to determine the process yield. Yields were 99 and 97% for the first and second batches, respectively. The conditions are summarized in Table 40 and PSD analyses in Table 41.

TABLE 40

| Micronization Conditions for L-Leucine Coated Compound 1 Wet Polishing | | |
|---|---|---|
| Parameter | BATCH 01 | BATCH 02 |
| Total Input amount (g) | 5000 | 5000 |
| Total Output amount (g) | 4974 | 4828 |
| Yield (%) | 99 | 97 |
| Compound 1 Input (g) | 250 | 238 |
| Theoretical output (g) | 249 | 230 |
| Suspension temperature (° C.) | 19-21 | 21-30 |
| Output chamber temperature (° C.) | 16-36 | 19-46 |
| Reactor agitation speed (RPM) | 320 | 320-390 |

TABLE 41

| PSD Analyses for L-Leucine Coated Compound 1 After Wet Polishing | | | |
|---|---|---|---|
| Number of cycles/Pressure | Dv10 (μm) | Dv50 (μm) | Dv90 (μm) |
| BATCH 1 | | | |
| 25/P = 70 bar | 0.3 | 1.0 | 4.5 |
| BATCH 2 | | | |
| 30/P = 70 bar | 0.3 | 0.8 | 3.6 |

Both batches were then spray dried as described in the previous example and summarized in Table 42. The final spray dried product was characterized for assay and related substances, PSD, water content by KF and XRPD and the results shown in Table 43. The two sub-batches were blended to obtain the final product, with a total final yield was 137 g (68%), see Table 44.

TABLE 42

| Spray Drying Conditions for L-Leucine Coated Compound 1 | | |
|---|---|---|
| Parameter | BATCH 01 | BATCH 02 |
| Input amount (g) | 4974 | 4828 |
| Compound 1 (g) | 249 | 230 |
| Added leucine (g) | 5.0 | 4.9 |
| Nozzle | 2.2/1.5 | 2.2/1.5 |
| $D_{drying}$ (kg/h) | 35 | 35 |
| $T_{in}$ (° C.) | 123-161 | 143-166 |
| $T_{out}$ measured (° C.) | 64-83 | 73-76 |
| Output cyclone 1 (g) | 142 | 171 |
| Output cyclone 2 (g) | 8 | 5 |
| SD theoretical yield (%) | 60 | 77 |

TABLE 43

| Individual Batch Analysis Individual batch Analyses | | | | | | |
|---|---|---|---|---|---|---|
| Cyclone | 1 | 1 | 1 | 2 | 1 | 2 |
| Dv10 (μm) | 0.3 | 0.3 | 0.3 | 0.4 | 0.3 | 0.3 |
| Dv50 (μm) | 0.8 | 0.7 | 0.6 | 0.9 | 0.6 | 0.8 |
| Dv90 (μm) | 3.6 | 3.2 | 2.0 | — | 2.3 | — |
| SPAN | 4.1 | 4.1 | 2.9 | — | 3.1 | — |

Final product showed a Dv50 of 0.6 μm, with the expected amorphous content, water content and XRPD peaks, see Table 44.

TABLE 44

| Final Product Analyses Final Product Analyses | |
|---|---|
| Dv10 (μm) | 0.3 |
| Dv50 (μm) | 0.6 |
| Dv90 (μm) | 2.0 |
| SPAN | 2.8 |
| XRPD | Expected |
| Assay (% LC) | 96.3 |
| Impurities (% area) | 1.2 |
| KF (% w/w) | 0.3 |
| Bulk density (g/ml) | 0.12 |

III Capsule Filling

The micronized material prepared in Steps I and II (crystalline Compound 1 Form A alone and with added L-Leucine) was used to perform capsule filling trials. HPMC size #3 capsules (Capsugel) were filled using an MG2 FlexaLab unit (500-3000 caps/hour), a fully automatic dosator-nozzle filling apparatus, where the powder was filled into a rotary product container, creating a powder bed where the dosator moves into and collects the desired volume of powder. In this process the dosator creates a powder plug by applying compaction to the powder bed. The dosed powder volume and compaction is adjusted by varying the powder bed layer depth in the rotary container, the dosing chamber height, and the dosator diameter. The capsule filling process included the following steps:

Charging of blend to the powder hopper and formation of the powder bed in the rotary container: by a vibrational system, the powder was dispensed from the hopper into the rotary container until a uniform bed of powder was formed. The rotary container was equipped with levelers which during filling prevent the formation of powder holes due to the immersion of the dosator. The machine ran for at least 30 minutes to allow the product to settle in the rotary container.

Adjustment of the dosator: the machine ran without using the MultiNETT (MG2) system and the fill weight was checked by weight difference on emptying. Successive adjustments were performed to the height of the dosator until the target fill weight was reached.

After batch initiation, filled capsules were collected and fill weight IPC carried out approximately every 100 capsules by weight difference on emptying 5 capsules.

A summary of the capsule filling parameters is presented in Table 45 (runs 1-5) and Table 46 (runs 6-9).

TABLE 45

| Parameters for Five Capsule Filling Trials - Compound 1 Alone | | | | | |
|---|---|---|---|---|---|
| Trial # | 1 | 2 | 3 | 4 * | 5 |
| Relative Humidity (%) | 27-43 | 26-51 | 31-49 | 19-42 | 40-50 |
| Temp (° C.) | 20-22 | 18-21 | 19-21 | 22-24 | 20-25 |

TABLE 45-continued

| Parameters for Five Capsule Filling Trials - Compound 1 Alone | | | | | |
|---|---|---|---|---|---|
| Trial # | 1 | 2 | 3 | 4 * | 5 |
| Dosator filling | | | | | |
| Bed depth (mm) | 12 | 12 | 12 | 12 | — |
| No capsules collected | 500 | 1500 | 500 | 500 | — |
| Av weight (manual IPC) (mg) | 12.2 ± 0.3 | 12.2 ± 0.7 | 11.7 ± 0.8 | 11.5 ± 0.4 | — |
| RSD (%) | 2.3 | 5.6 | 6.7 | 3.2 | — |
| Drum filling | | | | | |
| Product vacuum (mbar) | — | — | — | — | −600.0 |
| No capsules collected | | | | | 720 |
| No. single dosages/fill weight | — | — | — | — | 3 |
| Average weight (mg) | — | — | — | — | 18.2 ± 0.5 |
| RSD (%) | — | — | — | — | 2.8 |

* Product sieved (metallic sieve mesh 30) prior to capsule filling

TABLE 46

| Parameters for Four Capsule Filling Trials - Compound 1 + L-leucine | | | | |
|---|---|---|---|---|
| Trial # | 6 | 7 | 8 | 9 |
| HR % | 20-46 | 27-40 | 27-52 | 40-50 |
| Temperature | 21-25 | 21-24 | 18-23 | 20-25 |
| Dosator filling | | | | |
| Bed depth (mm) | 12 | 12 | 12 | — |
| No capsules collected | 500 | 1500 | 500 | — |
| Av weight (manual IPC) (mg) | 11.4 ± 1.1 | 11.4 ± 0.6 | 11.8 ± 0.7 | — |
| Max/min value from IPC | 10.1/14.1 | 9.9/12.5 | 9.0/13.0 | — |
| RSD (%) | 10.0 | 5.6 | 6.1 | — |
| Drum filling | | | | |
| Product vacuum (mbar) | — | — | — | −600.0 |
| No capsules collected | | | | 720 |
| No single dosages/filling weight | — | — | — | 4 |
| Average weight (mg) | — | — | — | 27.6 ± 0.8 |
| RSD (%) | — | — | — | 3.0 |

Batches were analyzed and the results summarized in Tables 47 and 48.

TABLE 47

| Capsule Characterization for Compound 1 Alone | | | | | |
|---|---|---|---|---|---|
| Trial # | 1 | 2 | 3 | 4 | 5 |
| Assay | | | | | |
| Label Claim (mg) | 12.2 | 12.2 | 11.7 | 11.7 | 18.2 |
| Assay (% LC) | — | 95.4 | — | — | 102.2 |
| Related substances (% area) | — | 1.3 | — | — | 1.2 |
| Content Uniformity | | | | | |
| Average (% LC) | 99.4 | 95.0 | 91.9 | 90.1 | 97.7 |
| RSD (%) | 4.9 | 4.1 | 11.5 | 10.6 | 3.9 |
| Water content by KF | | | | | |
| Water (% w/w) | — | 0.4 | — | — | 0.3 |
| DUSA | | | | | |
| ED (%) Average | 74.4 | 74.4 | 72.8 | 69.7 | 77.2 |
| ED (%) RSD | 5.8 | 7.2 | 5.3 | 10.2 | 7.7 |
| ED (% of average) Min | 110 | 113 | 107 | 112 | 109 |
| ED (% of average) Max | 91 | 87 | 88 | 84 | 82 |
| NGI | | | | | |
| ED (μg/capsule) Average | 8.5 | 8.9 | 9.7 | 7.4 | 14.0 |
| ED (μg/capsule) RSD | 0.8 | 0.7 | 0.7 | 1.1 | 0.5 |
| FPD (μg/capsule) Average | 5.0 | 4.9 | 5.4 | 4.5 | 8.7 |
| FPD (μg/capsule) RSD | 0.7 | 0.3 | 0.5 | 0.7 | 0.6 |
| ED (%) Average | 69.8 | 72.9 | 83.1 | 64.2 | 76.7 |
| ED (%) RSD | 6.9 | 5.9 | 6.1 | 9.3 | 2.5 |
| $FPF_{ED}$ (%) Average | 58.0 | 54.7 | 56.0 | 61.0 | 62.0 |
| $FPF_{ED}$ (%) RSD | 2.1 | 1.3 | 1.7 | 1.1 | 2.9 |
| MMAD (μm) Average | 2.8 | 3.0 | 2.9 | 2.8 | 2.8 |
| MMAD (μm) RSD | 0.0 | 0.1 | 0.1 | 0.0 | 0.1 |
| GSD Average | 1.9 | 1.9 | 1.9 | 1.9 | 1.8 |
| GSD RSD | 0.0 | 0.0 | 0.0 | 0.0 | 0.0 |

TABLE 47-continued

| Capsule Characterization for Compound 1 Alone | | | | | |
|---|---|---|---|---|---|
| Trial # | 1 | 2 | 3 | 4 | 5 |
| Mass balance (% LC) | Run 1: 78<br>Run 2: 98<br>Run 3: 84 | Run 1: 97<br>Run 2: 80<br>Run 3: 92 | Run 1: 92<br>Run 2: 101<br>Run 3: 111 | Run 1: 75<br>Run 2: 78<br>Run 3: 99 | Run 1: 98<br>Run 2: 100<br>Run 3: 104 |

LC = Label Claim
DUSA = Dosage Unit Sampling Apparatus
ED = Emitted Dose (from the inhaler device)
FPD = Fine Particle Dose
$FPF_{ED}$, Fine Particle Fraction (Fine Particle Dose over the Emitted Dose by NGI)
MMAD = Mass Median Aerodynamic Diameter
NGI = Next Generation Impactor
RSD = Relative Standard Deviation
GSD = Geometric Standard Deviation

TABLE 48

| Capsule Characterization for Compound 1 Plus L-leucine | | | | |
|---|---|---|---|---|
| Trial # | 6 | 7 | 8 | 9 |
| Assay | | | | |
| LC (mg) | 11.2 | 11.6 | 11.6 | 27.1 |
| Assay (% LC) | — | 92.0 | — | 100.3 |
| Related substances (% area) | — | 1.3 | — | 1.3 |
| Content Uniformity | | | | |
| Average (% LC) | 89.0 | 94.0 | 91.5 | 100.7 |
| RSD (%) | 11.2 | 8.9 | 9.7 | 2.2 |
| Water content by KF | | | | |
| Water (% w/w) | | 0.3 | | 0.3 |
| DUSA | | | | |
| ED (%) Average | 74.5 | 74.7 | 72.0 | 74.9 |
| ED (%) RSD | 10.2 | 12.5 | 15.2 | 6.7 |
| ED (% of average) Min | 120.5 | 118.2 | 126.0 | 107.9 |
| ED (% of average) Max | 87.2 | 84.7 | 82.6 | 85.7 |
| NGI | | | | |
| ED (μg/capsule) Average | 8.0 | 8.1 | 9.4 | 21.6 |
| ED (μg/capsule) RSD | 0.6 | 0.6 | 0.6 | 0.4 |
| FPD (μg/capsule) Average | 6.1 | 5.8 | 6.8 | 13.5 |
| FPD (μg/capsule) RSD | 0.8 | 0.4 | 0.4 | 0.5 |
| ED (%) Average | 71.3 | 72.1 | 81.3 | 79.8 |
| ED (%) RSD | 5.4 | 5.7 | 5.2 | 1.4 |
| FPFED (%) Average | 76.5 | 71.9 | 72.0 | 62.5 |
| FPFED (%) RSD | 3.8 | 2.6 | 1.2 | 1.3 |
| MMAD (μm) Average | 2.0 | 2.4 | 2.3 | 2.8 |
| MMAD (μm) RSD | 0.4 | 0.1 | 0.0 | 0.1 |
| GSD Average | 2.0 | 1.9 | 1.9 | 2.0 |
| GSD RSD | 0.1 | 0.0 | 0.0 | 0.0 |
| Mass balance (% LC) | Run 1: 87<br>Run 2: 87<br>Run 3: 100 | Run 1: 85<br>Run 2: 85<br>Run 3: 100 | Run 1: 109<br>Run 2: 103<br>Run 3: 92 | Run 1: 94<br>Run 2: 96<br>Run 3: 97 |

Example 12

Scale-Up of High-Dosage Crystalline Dry Powder Inhaler (Dpi) Formulation

Ninety percent of the purified water was added to the mixing vessel. 1.86 Kg of crystalline Compound 1 Form B was added to the mixing vessel followed by the remaining portion of purified water to achieve a 5% w/w suspension. The mixture was stirred between 200 and 600 rpm for at least 2 hours until a homogenous suspension was observed. The suspension was pre-micronized using a high pressure homogenizer equipped with a 400 μm micronization chamber at a pressure of 70 bar. The temperature of the suspension was maintained between 15 and 25° C. and the particle size distribution of Compound 1 was monitored by laser diffraction. The suspension was further micronized using a 100 μm micronization chamber at a pressure of 70 bar until the particle size Dv50 of Compound 1 in suspension was below 1 μm. 0.14 Kg of L-leucine was added to the micronized Compound 1 in suspension while mixing. The L-leucine was allowed to dissolve for at least 30 minutes until the suspension was homogenous.

A PSD-1 spray dryer was assembled and configured with appropriate cyclone(s) and collection containers for Compound 1 spray-dried powder. Following start-up procedures, the micronized suspension was spray-dried with nitrogen drying gas using the following target (set point) conditions:

| | |
|---|---|
| Process Gas Inlet Temperature: | 125° C. |
| Process Gas Outlet Temperature: | 75° C. |
| Process Gas Flow rate: | 100 Kg/hr |
| Liquid Feed Flow rate: | 1.2 Kg/hr |
| Atomization Gas Flow: | 3.3 Kg/hr |

Process parameters were recorded approximately every 30 minutes and cyclone collection containers were replaced approximately every 4 hours.

Capsules were hand-filled and tested for aerosol performance, as summarized in Table 49 below.

TABLE 49

| Aerosol Performance | |
|---|---|
| Assay (HPLC) | 98.8% LC |
| Characterization (XRPD) | Presence of characteristics peaks of crystalline Form B |
| Fill Weight | 43.5 mg |
| ED (mg/cap) | 26.9 |
| FPD (mg/cap) | 17.3 |
| FPF (%) | 64.4 |
| MMAD (mm) | 3.3 |
| GSD | 1.7 |

Example 13

High-Dosage Amorphous Dry Powder Inhaler (DPI) Formulation 3.25 Kg of crystalline Compound 1 Form A and 3.25 Kg of L-leucine were dispensed. Enough water and ethanol were dispensed to have a 1.26% w/w solution. L-leucine was added to the water in a stainless-steel process tank while mixing. The L-leucine was allowed to dissolve in the water for a minimum of one hour until a visually clear solution was obtained. The process tank was purged with nitrogen and dehydrated alcohol was added to the L-leucine solution. Compound 1 was added and the contents were mixed for a minimum of one hour until a visually clear to slightly-hazy solution was obtained.

A PSD-1 spray dryer was assembled and configured with appropriate cyclone(s) and collection containers for Compound 1 spray-dried powder. Two 0.2-μm filters were installed in series in the feedline between the solution tank and the spray dryer nozzles. Filter integrity (i.e., bubble point) was determined after the process was completed. Following startup procedures, the solution was spray-dried with nitrogen drying gas using the following target (set point) conditions:

| | |
|---|---|
| Process Gas Inlet Temperature | 160° C. |
| Process Gas Outlet Temperature | 60° C. |
| Process Gas Flow rate | 2870 g/min |
| Liquid Feed Flow rate | 110 g/min |
| Atomization Gas Pressure | 22 psig |

Process parameters are recorded approximately every 10 minutes and cyclone collection containers are replaced approximately every 16 hours.

A Harro Hoflinger Modu-C encapsulator, capsule polisher, and metal detector were assembled and staged along with all process consumables. The hopper was loaded with the Compound 1 spray-dried powder and stirred with an angled, two-blade stirrer. Encapsulation was performed utilizing automatic mass verification (AMV) sorting limits of +/−7.5% of the target fill weight. Capsule fill weight and closed length were measured throughout the encapsulation process to verify mean capsule weights are within 0.5 mg of the AMV system and to verify that the capsules are adequately closed. Capsules were tested for aerosol performance, as summarized in Table 50 below.

TABLE 50

| Aerosol Performance | |
|---|---|
| Assay (HPLC) | 98.3% LC |
| Water content (Coulometric Titration) | 1.23% |
| Characterization (XRPD) | Amorphous Compound 1 with spray dried crystalline leucine character |
| Fill Weight | 30 mg |
| ED (mg/cap) | 13.6 |
| FPD (mg/cap) | 8.4 |
| FPF (%) | 61.8 |
| MMAD (mm) | 2.6 |
| GSD | 1.83 |

Example 14

Solubility of Various Forms of Compound 1

The solubilities of crystalline Compound 1 Form A, amorphous Compound 1, L-leucine and Compound 1/L-leucine spray dried powder (SDP) mixtures in phosphate buffer and ethanol/water mixtures were examined.

Sample Preparation

Samples of crystalline Compound 1 Form A, amorphous Compound 1, Compound 1/L-leucine SPD (70:30), Compound 1/L-leucine SPD (50:50) and L-Leucine were examined in the test solutions below and the results presented in Tables 51 and 52.

Phosphate Buffer contained $NaH_2PO_4 \cdot H_2O$ (0.345 g), sodium hydroxide aqueous solution (0.2M, 10.001 mL), sodium chloride (0.576 g) and water (qs ad 100.0 mL);

- Ethanol/Water (30/70) contained Ethanol (30.0 g) and Water (70.0 g);
- Ethanol/Water (40/60) contained Ethanol (40.0 g) and Water (60.0 g);
- Ethanol/Water (50/50) contained Ethanol (50.0 g) and Water (50.0 g); and
- Ethanol/Water (45/55) contained Ethanol (4.50 g) and Water (5.51 g).

TABLE 51

Solubility Results in 25 mM Phosphate Buffer pH 7.4

| Sample | Equil time (hrs) | μg/mL |
|---|---|---|
| Crystalline | 1 | 3.46 |
| | 4 | 3.16 |
| | 24 | 3.05 |
| Amorphous | 1 | 6.95 |
| | 4 | 5.58 |
| | 24 | 3.97 |
| SDP (70:30) | 1 | 5.81 |
| | 4 | 5.73 |
| | 24 | 4.57 |
| SDP (50:50) | 1 | 7.11 |
| | 4 | 5.01 |
| | 24 | 4.19 |

The solubility results in ethanol/water at 22° C. are shown in Table 52.

TABLE 52

| Solubility in Ethanol/Water | | | | |
|---|---|---|---|---|
| Sample | EtOH/$H_2O$ (w:w) | 4 Hours (mg/mL) | 24 Hours (mg/mL) | Average (mg/mL) |
| Amorphous | 30:70 | 2.92 | 2.92 | 2.92 |
| | 40:60 | 25.8 | 24.3 | 25.0 |
| | 50:50 | >70 | >67 | >70 |
| Crystalline | 30:70 | 2.15 | 2.11 | 2.13 |
| | 40:60 | 18.9 | 18.3 | 18.6 |
| | 45:55 | 53.3 | 43.3 | 48.3 |
| | 50:50[T] | 125 | 177 | — |
| | 50:50[B] | 222 | 362* | — |
| L-Leucine | 30:70 | 7.47 | 7.26 | 7.36 |
| | 40:60 | 6.04 | 5.71 | 5.88 |
| | 50:50 | 4.72 | 5.41 | 5.07 |

[T]Top layer after centrifugation
[B]Bottom layer after centrifugation
*Result outside calibration curve

Example 15

In Vivo Studies

Three in vivo PKPD studies were used to evaluate the pharmacology of Test Formulation (i.e., the capsules containing crystalline Compound 1 Form B of Example 12) vs Reference Formulation (i.e., the capsules containing amorphous Compound 1 of Example 13). These head-to-head studies showed that, the passive inhalation delivery of the Test Formulation (qd dosing for 3 days) yielded significantly higher lung exposure compared to the Reference Formulation. Overall, the Test Formulation lung exposures were roughly 2× over the Reference Formulation. The Test Formulation inhibits PDGFB and SCF induced phosphorylation of PDGFR and cKIT. The Test Formulation displayed more potent inhibition of phosphorylation of PDGFR and cKIT immediately post dosing. This target engagement was sustained at 8 hours post dosing for the Test Formulation, whereas there was reversal of inhibition for the Reference Formulation which corresponds to lung levels. The results of these studies is presented in Table 53.

TABLE 53

| PKPD Summary for Test Formulation vs Reference Formulation | | | | |
|---|---|---|---|---|
| | Reference Formulation (15 mg/kg) | | Test Formulation (15 mg/kg) | |
| Plasma $C_{max}$ (ng/ml) | 259 | | 270 | |
| Plasma $AUC_{last}$ (hr*ng/mL) | 822 | | 643 | |
| Lung $C_{max}$ (ng/g) | 11900 | | 27100 | |
| Lung $AUC_{last}$ (hr*ng/mL) | 39900 | | 72400 | |
| Lung tissue levels and target engagement | | | | |
| Time point | at 2.25 h | at 8 h | at 2.25 h | at 8 h |
| Lung conc. (ng/g) (Mean ± SD) | 8930 ± 4650 | 235 ± 126 | 24800 ± 5000 | 1180 ± 674 |
| % pPDGFR inhibition | 54 | 0 | 83 | 47 |
| % pcKIT inhibition | 42 | 9 | 74 | 14 |

Example 16

Clinical Trial Results

A Phase 1 study to evaluate the bioavailability of the Test Formulation (crystalline Compound 1 Form B) compared to the Reference Formulation (amorphous Compound 1) as identified in Example 15 was conducted in a crossover study. The study design is described below. Briefly, it was a 2-part, 2-treatment, 2-period, randomized, open-label, crossover design. Participants were required to participate in both Parts 1 and 2 and received single oral inhalation doses of the two formulations.

Period 1

On day 1, enrolled subjects were administered either a single oral inhalation dose of the Test Formulation of crystalline Compound 1 (1×40 mg capsule of the 93% w/w formulation) or a single oral inhalation dose the Reference Formulation of an amorphous form of Compound 1 (3×15 mg capsules of the 50% w/w formulation) under fasting conditions. This was followed by a 3-day washout.

Period 2

Subjects were crossed over on day 4. Subjects that received Test Formulation in Period 1 received Reference Formulation in Period 2, and subjects that received Reference Formulation in Period 1 received Test Formulation in Period 2. Administration was again carried out under the same fasting conditions. A 72-hour pharmacokinetic (PK) assessment followed each of the administrations. Following drug administration in Period 2, subjects were confined through Day 7 for safety and PK assessments.

Results 22 subjects were enrolled and 21 completed Periods 1 and 2. Both formulations were well tolerated, and no significant abnormalities were noted in vital signs, ECG, and laboratory results.

Amounts Dosed

The amount of Compound 1 dosed per capsule was determined to confirm actual dose dispersed by gravimetric analysis of the amount of powder that was dispensed from the device (device weighed before and after dosing). The dosed weight was multiplied by the content of Compound 1 for each formulation to determine the amount emitted for each subject.

PK Analyses

Figure 38A:
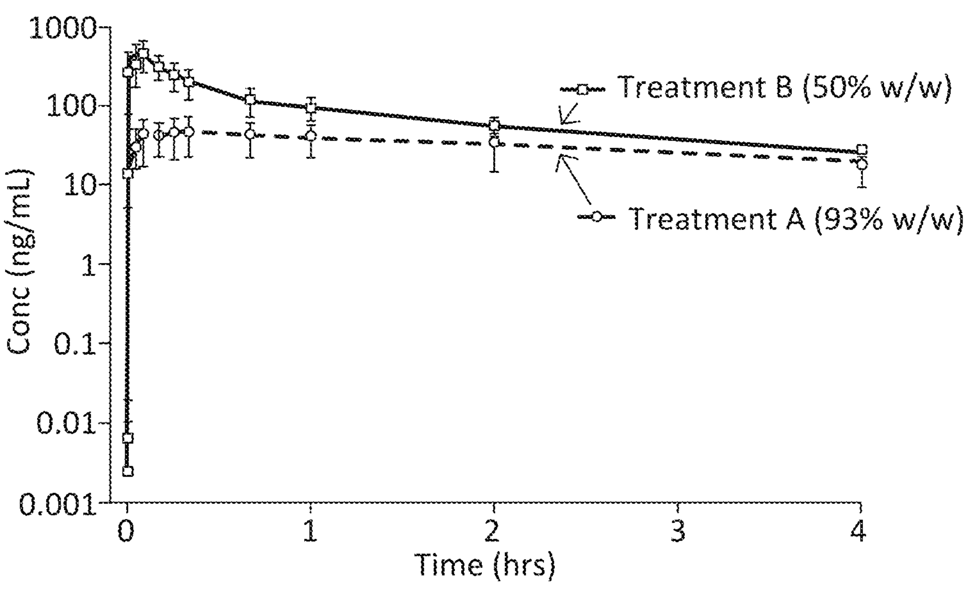
FIGS. 38A and 38B: Mean concentration-time profiles of Compound 1 (±SD) over 4 hours and 72 hours, respectively. (Treatment A—Test Formulation, Treatment B—Reference Formulation).
Figure 38B:
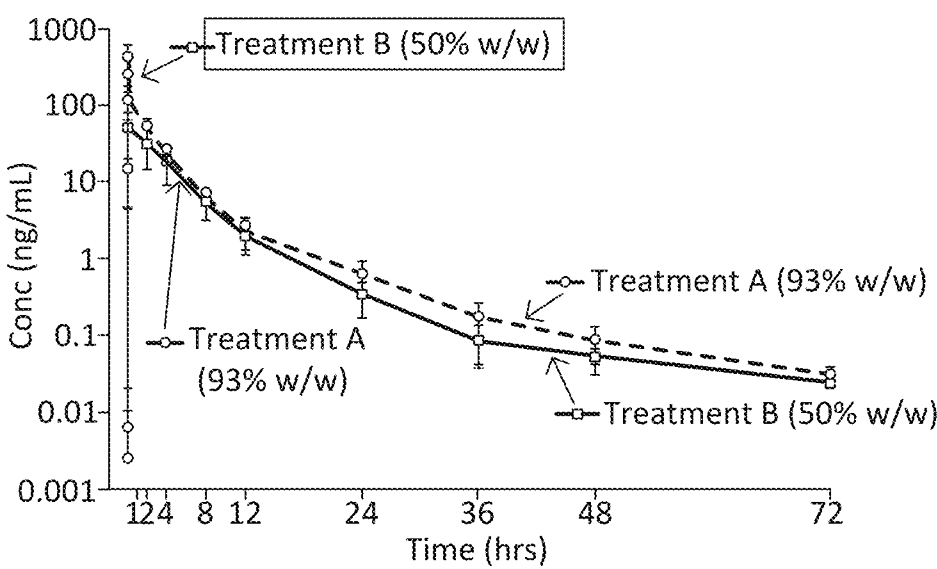

FIGS. 38A and 38B present the mean concentration-time profiles of Compound 1 (±SD) over 4 hours and 72 hours, respectively (Treatment A=Test Formulation, Treatment B=Reference Formulation).

As shown in FIGS. 38A and 38B, the concentration-time profile of the Test Formulation was found to be distinct from the Reference Formulation. The rate and extent of Compound 1 availability in systemic circulation was altered; namely, $C_{max}$ was approximately 10-fold reduced. When the amount of Compound 1 is normalized to the fine particle dose, the AUC of the Test Formulation was 82% of the Reference Formulation. The Test Formulation was found to prolong lung exposure, resulting in a more favorable PK profile where the $C_{max}$ is lower and AUC is extended when matching systemic exposure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

All publications, patents, and patent applications mentioned in this specification are herein incorporated by reference to the same extent as if each individual publication, patent, or patent application was specifically and individually indicated to be incorporated by reference.

The invention claimed is:

1. A solid crystalline form of N-{3-[(1S)-1-{[6-(3,4-dimethoxyphenyl) pyrazin-2-yl]amino}ethyl]phenyl}-5-methylpyridine-3-carboxamide, wherein the crystalline form is Form A characterized by an XRPD pattern having peaks at 5.5, 7.8, 11.0, 12.3 and 15.6±0.2 degrees 2-theta, or wherein the crystalline form is Form B characterized by an XRPD pattern having peaks at 5.2, 6.1, 7.6, 11.5 and 12.3±0.2 degrees 2-theta or a mixture thereof.

2. The solid crystalline form of claim 1, wherein the crystalline form is Form A characterized by an XRPD pattern having peaks at 5.5, 7.8, 11.0, 12.3 and 15.6±0.2 degrees 2-theta.

3. The crystalline form of claim 2, further characterized by an XRPD pattern substantially as shown in FIG. 9.

4. The solid crystalline form of claim 2, comprising at least 80% Form A.

5. The solid crystalline form of claim 4, comprising at least 90% Form A.

6. The solid crystalline form of claim 1, wherein the crystalline form is Form B characterized by an XRPD pattern having peaks at 5.2, 6.1, 7.6, 11.5 and 12.3±0.2 degrees 2-theta.

7. The solid crystalline form of claim 6, further characterized by an XRPD pattern substantially as shown in FIG. 10.

8. The solid crystalline form of claim 6, comprising at least 80% Form B.

9. The solid crystalline form of claim 8, comprising at least 90% Form B.

10. The solid crystalline form of claim 2, wherein the crystalline form is substantially pure Form A.

11. The solid crystalline form of claim 6, wherein the crystalline form is substantially pure Form B.

12. The solid crystalline form of claim 1, wherein the crystalline form is a mixture of Form A and Form B.

13. A pharmaceutical composition comprising the solid crystalline form of claim 1 in combination with one or more pharmaceutically acceptable carriers.

14. The pharmaceutical composition of claim 13 comprising an additional therapeutically active compound.

15. The pharmaceutical composition of claim 13, wherein the composition is formulated for administration to the respiratory track.

16. The pharmaceutical composition of claim 13, wherein the composition is in the form of an inhalable powder.

17. The pharmaceutical composition of claim 13, wherein the composition is in the form of a dry powder.

18. The pharmaceutical composition of claim 16, wherein the inhalable powder comprises particles having a Dv50 of 2-3 um.

19. The pharmaceutical composition of claim 16, wherein the inhalable powder has a mass median aerodynamic diameter of 0.9 to 4.0 um.

20. The pharmaceutical composition of claim 16, wherein the inhalable powder is obtained by wet-milling micronization in an aqueous solution.

21. The pharmaceutical composition of claim 16, wherein the inhalable powder is obtained by jet milling micronization.

22. The pharmaceutical composition of claim 16, wherein the inhalable powder has greater than 90% of the starting crystalline form.

23. The pharmaceutical composition of claim 16, wherein the inhalable powder has greater than 75% % of the starting crystalline form.

24. The pharmaceutical composition of claim 13, wherein the one or more pharmaceutically acceptable carriers comprises lactose.

25. The pharmaceutical composition of claim 13, further comprising leucine.

26. The pharmaceutical composition of claim 25, wherein leucine coats the solid crystalline form.

27. The pharmaceutical composition of claim 26, wherein the leucine coated solid crystalline form is obtained by addition of leucine to a wet-milled crystalline form suspension prior to spray drying.

28. A pharmaceutical dosage form comprising the pharmaceutical composition of claim 13.

29. The pharmaceutical dosage form of claim 28, wherein the dosage form is a capsule for administration with a dry powder inhaler.

30. The pharmaceutical dosage form of claim 28, wherein the dosage form is a blister for administration with a dry powder inhaler.

31. The pharmaceutical dosage form of claim 28, wherein the dosage form is a powder for administration with a dry powder inhaler.

32. A solid unit dosage form comprising the solid crystalline form of claim 1.

33. The solid unit dosage form of claim 32, wherein the dosage form is formulated for administration to the respiratory track.

34. The solid unit dosage form of claim 32, wherein the dosage form is in the form of an inhalable powder.

35. The solid unit dosage form of claim 32, wherein the dosage form is in the form of a dry powder.

36. The solid unit dosage form of claim 34, wherein the inhalable powder comprises particles having a Dv50 of 2-3 um.

37. The solid unit dosage form of claim 34, wherein the inhalable powder has a mass median aerodynamic diameter of 0.9 to 4.0 um.

38. The solid unit dosage form of claim 34, wherein the inhalable powder is obtained by wet-milling micronization in an aqueous solution.

39. The solid unit dosage form of claim 34, wherein the inhalable powder is obtained by jet milling micronization.

40. The solid unit dosage form of claim 34, wherein the inhalable powder has greater than 90% of the starting crystalline form.

41. The solid unit dosage form of claim 34, wherein the inhalable powder has greater than 75% % of the starting crystalline form.

42. The solid unit dosage form of claim 32, further comprising leucine.

43. The solid unit dosage form of claim 42, wherein leucine coats the solid crystalline form.

44. The solid unit dosage form of claim 43, wherein the leucine coated solid crystalline form is obtained by addition of leucine to a wet-milled crystalline form suspension prior to spray drying.

45. The solid unit dosage form of claim 32, wherein the dosage form is a capsule for administration with a dry powder inhaler.

46. The solid unit dosage form of claim 32, wherein the dosage form is a blister for administration with a dry powder inhaler.

47. The solid unit dosage form of claim 32, wherein the dosage form is a powder for administration with a dry powder inhaler.

48. A method for treating a disease or condition comprising administering to a subject in need thereof an effective amount of the solid crystalline form of claim 1, wherein the disease or condition is PAH, primary PAH, idiopathic PAH, heritable PAH, refractory PAH, drug-induced PAH, toxin-induced PAH, or PAH with secondary diseases.

49. The method of claim 48, wherein the disease or condition is PAH.

50. A process for preparing the solid crystalline form of claim 1 by crystallization from a solvent comprising ethyl acetate.

51. The process of claim 50, wherein the solvent further comprises n-heptane.

52. The process of claim 50, wherein the crystalline form is Form A.

53. The process of claim 50, wherein the crystalline form is Form B.

54. A process for preparing the solid crystalline form of claim 1 by crystallization from a solvent comprising ethanol.

55. The process of claim 54, wherein the crystalline form is Form B.

56. The process of claim 50, wherein the solvent further comprises water.

57. A method for preparing Form B of N-{3-[(1S)-1-{[6-(3,4-dimethoxyphenyl) pyrazin-2-yl] amino}ethyl] phenyl}-5-methylpyridine-3-carboxamide comprising slurrying Form A of N-{3-[(1S)-1-{[6-(3,4-dimethoxyphenyl) pyrazin-2-yl]amino} ethyl]phenyl}-5-methylpyridine-3-carboxamide in ethyl acetate and holding its temperature from about 10° C. to about 45° C. for a period of time from about 1 minute to 90 hours, wherein Form A is characterized by an XRPD pattern having peaks at 5.5, 7.8, 11.0, 12.3 and 15.6±0.2 degrees 2-theta, and Form B is characterized by an XRPD pattern having peaks at 5.2, 6.1, 7.6, 11.5 and 12.3±0.2 degrees 2-theta.

* * * * *